US012649740B2

United States Patent

(12) United States Patent
Cohen et al.

(10) Patent No.: US 12,649,740 B2
(45) Date of Patent: Jun. 9, 2026

(54) ADENOSINE ANALOGS FOR THE TREATMENT OF DISEASE

(71) Applicant: BIOINTERVENE, INC., Brisbane, CA (US)

(72) Inventors: Charles J. Cohen, Los Angeles, CA (US); Arthur F. Kluge, Gainesville, FL (US); Soumya S. Ray, Quincy, MA (US); John H. Hutchinson, San Diego, CA (US)

(73) Assignee: BIOINTERVENE, INC., Atherton, CA (US)

(*) Notice: Subject to any disclaimer, the term of this patent is extended or adjusted under 35 U.S.C. 154(b) by 654 days.

(21) Appl. No.: 18/169,321

(22) Filed: Feb. 15, 2023

(65) Prior Publication Data

US 2023/0416245 A1 Dec. 28, 2023

Related U.S. Application Data

(63) Continuation of application No. PCT/US2021/046385, filed on Aug. 17, 2021.

(60) Provisional application No. 63/066,757, filed on Aug. 17, 2020, provisional application No. 63/171,949, filed on Apr. 7, 2021, provisional application No. 63/172,570, filed on Apr. 8, 2021.

(51) Int. Cl.

| | |
|---|---|
| ***C07D 471/04*** | (2006.01) |
| ***A61K 31/437*** | (2006.01) |
| ***A61P 25/02*** | (2006.01) |
| ***A61P 29/00*** | (2006.01) |

(52) U.S. Cl.

CPC ............ *C07D 471/04* (2013.01); *A61P 25/02* (2018.01); *A61P 29/00* (2018.01)

(58) Field of Classification Search

CPC .. C07D 471/04; C07D 487/04; A61K 31/437; A61P 25/02; A61P 35/00

USPC .......................... 546/118; 514/303; 544/256

See application file for complete search history.

(56) References Cited

U.S. PATENT DOCUMENTS

| | | | |
|---|---|---|---|
| 8,735,407 | B2 | 5/2014 | Jacobson et al. |
| 8,796,291 | B2 | 8/2014 | Jacobson et al. |
| 8,916,570 | B2 | 12/2014 | Jacobson et al. |
| 9,181,253 | B2 | 11/2015 | Jacobson et al. |
| 9,963,450 | B2 | 5/2018 | Jacobson et al. |
| 10,577,368 | B2 | 3/2020 | Jacobson et al. |
| 2012/0252823 | A1 | 10/2012 | Jacobson et al. |
| 2019/0343860 | A1 | 11/2019 | Salvemini |
| 2020/0117985 | A1 | 4/2020 | Burr |
| 2022/0218712 | A1 | 7/2022 | Salvemini et al. |

FOREIGN PATENT DOCUMENTS

| | | | |
|---|---|---|---|
| CN | 105934433 | A | 9/2016 |
| CN | 110003212 | A | 7/2019 |
| WO | WO-0151490 | A1 | 7/2001 |
| WO | WO-03061670 | A1 | 7/2003 |
| WO | WO-2004022573 | A2 | 3/2004 |
| WO | WO-2008156513 | A2 | 12/2008 |
| WO | WO-2009123881 | A1 | 10/2009 |
| WO | WO-2010014921 | A2 | 2/2010 |
| WO | WO-2015080940 | A1 | 6/2015 |
| WO | WO-2017189504 | A1 | 11/2017 |
| WO | WO-2019232554 | A2 | 12/2019 |
| WO | WO-2020061211 | A1 | 3/2020 |
| WO | WO-2020106773 | A1 | 5/2020 |
| WO | WO-2020168274 | A1 | 8/2020 |
| WO | WO-2020176544 | A1 | 9/2020 |
| WO | WO-2022040241 | A1 | 2/2022 |
| WO | WO-2024064701 | A3 | 5/2024 |

OTHER PUBLICATIONS

Tosh, D.K. et al.: Truncated (N)-methanocarba nucleosides as partial agonists at mouse and human A3 adenosine receptors: Affinity enhancement by N6-(2-phenylethyl) substitution. J. Med. Chem., vol. 63, pp. 4334-4348, 2020.*

Nayak, A et al., Synthesis and Anti-Renal Fibrosis Activity of Conformationally Locked Truncated 2-Hexynyl-N6 -Substituted-(N)-Methanocarbanucleosides as A3 Adenosine Receptor Antagonists and Partial Agonists. Journal of Medicinal Chemistry, vol. 57, No. 4, Feb. 27, 2014, 1344-1354.

PCT/US2021/046385 International Search Report and Written Opinion dated Jan. 3, 2022.

Tosh, D. K. et al., Direct Comparison of (N)-Methanocarba and Ribose-Containing 2-Arylalkynyladenosine Derivatives as A3 Receptor Agonists. ACS Medicinal Chemistry Letters, vol. 11, No. 10, Oct. 8, 2020, pp. 1935-1941.

Tosh, D. K. et al., Truncated (N)-Methanocarba Nucleosides as A1 Adenosine Receptor Agonists and Partial Agonists: Overcoming Lack of a Recognition Element, ACS Med. Chem. Lett. Aug. 11, 2011, 2(8), 626-631.

Tosh, et al., Truncated Nucleosides as A3 Adenosine Receptor Ligands: Combined 2-Arylethynyl and Bicyclohexane Substitutions. ACS Med. Chem. Lett. 2012, 3, 596-601.

PCT/US2023/074613 International Search Report and Written Opinion dated Mar. 27, 2024.

Petrelli, Riccardo, et al. 5'-C-Ethyl-tetrazolyl-N(6)-substituted adenosine and 2-chloro-adenosine derivatives as highly potent dual acting A1 adenosine receptor agonists and A3 adenosine receptor antagonists. Journal of medicinal chemistry. 58, 5:2560-2566 (2015).

Tosh, Dilip, et al. Rigidified A3 Adenosine Receptor Agonists: 1-Deazaadenine Modification Maintains High in Vivo Efficacy. ACS medicinal chemistry letters. 6, 7:804-808 (2015).

* cited by examiner

*Primary Examiner* — Charanjit Aulakh

(74) *Attorney, Agent, or Firm* — WILSON SONSINI GOODRICH & ROSATI

(57) ABSTRACT

The disclosure provides adenosine analogs for the treatment of disease such as pain and inflammatory conditions.

16 Claims, No Drawings

ADENOSINE ANALOGS FOR THE TREATMENT OF DISEASE

CROSS-REFERENCE

This application is a continuation of International Patent Application No. PCT/US2021/046385, filed on Aug. 17, 2021, which claims the benefit of U.S. Provisional Patent Application No. 63/066,757 filed on Aug. 17, 2020; U.S. Provisional Patent Application No. 63/171,949 filed on Apr. 7, 2021; and U.S. Provisional Patent Application No. 63/172,570 filed on Apr. 8, 2021; each of which is incorporated herein by reference in its entirety.

BACKGROUND OF THE INVENTION

Extracellular concentrations of adenosine, a purine nucleoside, increase dramatically when cells are stressed or injured, or when neurotransmitters are released from neurons. This occurs in most, if not all, organs, including the nervous system. Cellular responses to adenosine are mediated via four G-protein-coupled receptors, which are designated $A_1$, $A_{2A}$, $A_{2B}$, and $A_3$. These adenosine receptor subtypes are found on many different cell types in most, if not all, tissues, and in at least some cases their expression is known to be increased in the presence of pathologies or diseases. While adenosine activates all four receptor subtypes, various compounds and drugs have different abilities to activate one subtype over the others. Therapeutically, the use of a selective adenosine receptor agonist may have the advantage of avoiding potentially deleterious effects due to activation of one or more of the other subtypes.

Working through adenosine receptors, increased extracellular adenosine concentrations can modulate responses from the innate immune system, inappropriate activation of which has been implicated in many diseases and conditions. Adenosine receptor activation can also alter the properties of astrocytes, microglia and neurons in the nervous system. Via one mechanism, activation of the $A_3$ adenosine receptor ($A_3AR$) can inhibit the formation of the NLRP3 (NOD-like receptor family pyrin domain-containing 3) inflammasome, an intracellular multiprotein complex that causes the generation of interleukin-1 beta (IL-1β). IL-1β is a key mediator of acute and chronic inflammatory responses. Activation of $A_3ARs$ with agonists has been shown to inhibit inflammasome activity and thereby reduce the inflammation and pain that are caused by IL-1β and other pro-inflammatory cytokines. Moreover, inflammasome-mediated chronic inflammation is often associated with cellular degeneration, for example, the loss of central nervous system cells in neurodegenerative conditions such as Alzheimer's disease and Parkinson's disease.

Chronic inflammatory diseases that affect various tissue types are also known to involve dysfunction of the cell's mitochondria, which provide the energy needed to drive all cellular processes. Energy deficit potentiates cellular stress and when severe causes cellular degeneration. Mitochondrial dysfunction may cause inflammation and inflammation may cause mitochondrial dysfunction. A3 adenosine receptor (AR) agonists are known to protect against mitochondrial insult and to inhibit cell degeneration.

Activation of A3ARs is known to promote multiple cell signaling pathways. A3ARs inhibit adenylyl cyclase activity through $G_i$ G-proteins, and stimulate phospholipase C/inositol trisphosphate/diacylglycerol pathway via Gβγ G-proteins. These receptors also couple to mitogen-activated protein kinases (MAPKs) including ERK 1 and 2. Gβγ proteins also mediate modulation of voltage-gated calcium channels and G-protein gated inward rectifying potassium channels (GIRK and Kir6) so as to inhibit hyperexcitability. In addition, activation of A3AR is coupled to translocation of beta-arrestin. Previous studies have shown that some A3AR agonists with a methanocarba motif in place of a ribose ring show biased agonism, meaning that compounds show differing potencies and efficacies for the pathways triggered by ligand binding (Baltos et al., Mol. Pharmacol. 90:12 (2016)). The utility and safety of A3AR agonists is dependent upon the spectrum of activity and the profile needed for anti-inflammatory or analgesic activity and previous studies with structurally dissimilar A3AR agonists did not enable one to predict the spectrum of activity for the novel compounds described in this application. As noted, biased agonism is observed with compounds with the methanocarba motif and the compounds in this report contain modifications in the methanocarba substituent that result in divergent patterns of biased agonist activity.

Tissue inflammation is often accompanied by pain. Pain due to damage to the peripheral nerves and certain regions of the central nervous system is called neuropathic pain. Multiple lines of evidence indicate that some chronic inflammatory pain conditions, including, but not limited to, chronic neuropathic pain and chronic mixed-pain conditions (which combine ordinary inflammatory pain and neuropathic pain), involve inflammasome activity. Selective $A_3AR$ agonists are analgesics in chronic inflammatory, neuropathic and mixed-pain conditions. $A_3AR$-mediated analgesia is accompanied by mitochondrial protection and by a decrease in the levels of IL-1β and other pro-inflammatory cytokines.

In the central nervous system, chronic inflammasome activity leading to increased levels of IL-1β and other pro-inflammatory cytokines induces a generalized impairment of cognitive function. For example, patients exposed to certain chemotherapeutic drugs develop a persistent (months to years) condition known as chemotherapy-induced cognitive impairment ("chemo-brain"; "chemo-fog"). Patients recovering from head trauma develop a similar syndrome (traumatic brain injury-induced cognitive dysfunction, or "post-concussion syndrome"). A cognitive impairment syndrome is also seen after surgery, especially after cardiopulmonary bypass surgery and especially in the elderly (post-operative cognitive dysfunction). Selective $A_3AR$ agonists may treat and prevent cognitive impairment syndromes.

The innate immune system responds to various toxins, including certain plant alkaloids such as morphine and also its synthetic congeners (generically known as opioids). Exposure to analgesic levels of an opioid leads to inflammasome formation, increased levels of IL-1β and the pro-inflammatory cascade which contribute to many of the unwanted side-effects of opioids, including but not limited to physiological dependence (a contributor to addiction), and analgesic tolerance (the phenomenon whereby repeated doses of an opioid produce progressively less analgesia, thus requiring dose escalation to maintain adequate analgesia). Selective $A_3AR$ agonists may attenuate opioid-induced inflammasome activation, dependence/addiction and tolerance.

Inhibition of voltage gated calcium channels in nociceptors is a clinically proven means of treating neuropathic pain, as evidenced by clinical studies with gabapentin and the peptide Prialt. Activation of adenosine receptors in nociceptors inhibits the activation of CaV2.1 and CaV2.2 channels, mimicking the effect of direct inhibitors of the channels and thereby inhibiting painful nociception. In some studies, the effects of adenosine on voltage gated calcium channels can be recapitulated by selective activation of A3AR, indicating the importance of this pathway for analgesic activity.

Generally, disease, trauma or other pathologies may lead to an upregulation of $A_3ARs$ on cells, affording the opportunity for selective $A_3AR$ agonists to treat or manage a wide variety of diseases and conditions suffered by humans and other animals.

There remains a need for adenosine receptor agonists for the treatment of disease.

SUMMARY OF THE INVENTION

In some aspects, the present disclosure provides a compound represented by Formula (I):

(I)

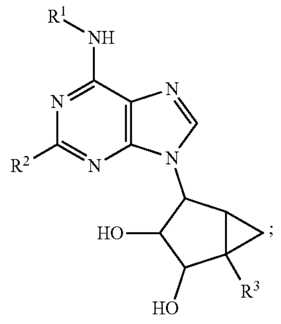

or a pharmaceutically acceptable salt thereof, wherein:

$R^1$ is selected from —$CD_3$, $C_2$ fluoroalkyl, $C_4$-$C_6$ fluoroalkyl, and $C_2$-$C_6$ alkyl substituted with phenyl, wherein the phenyl is substituted with one or more fluorine atoms;

$R^2$ is selected from hydrogen, halogen, $C_3$-$C_6$ cycloalkyl, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted with one or more substituents independently selected from R*; and $R^3$ is selected from hydrogen, $C_1$-$C_6$ alkyl, and $C_1$-$C_6$ haloalkyl; and each R* is independently selected from fluorine —$OR^{20}$, —$N(R^{20})_2$, —$N(R^{20})_2$, —$C(O)R^{20}$, —$C(O)OR^{20}$, —$OC(O)R^{20}$, —$NO_2$, and —CN; and $C_{3-6}$ carbocycle and 3- to 6-membered heterocycle each of which is optionally substituted with one or more substituents independently selected from halogen, —$OR^{20}$, —$N(R^{20})_2$, —$NO_2$, —CN, and $C_{1-3}$ alkyl; and $R^{20}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle and 3- to 6-membered heterocycle.

In certain aspects, the disclosure provides a compound represented by Formula (II'):

(II')

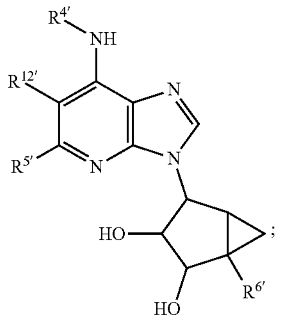

or a pharmaceutically acceptable salt thereof, wherein:

$R^{4'}$ is selected from hydrogen, optionally substituted $C_1$-$C_6$ alkyl, optionally substituted $C_3$-$C_8$ carbocycle and optionally substituted 3 to 8-membered heterocycle, wherein optional substituents on $C_1$-$C_6$ alkyl are independently selected from $R^7$ and optional substituents on $C_3$-$C_8$ carbocycle and 3 to 8-membered heterocycle are independently selected from $R^8$;

$R^{2'}$ is selected from hydrogen, —$NO_2$, —CN, —$NH_2$, halogen, $C_3$-$C_6$ cycloalkyl, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted with one or more substituents independently selected from $R^1$;

$R^{6'}$ is selected from hydrogen, —$C(O)(NR^{50}{}_2)$, and optionally substituted $C_1$-$C_3$ alkyl, wherein optional substituents on $C_1$-$C_3$ alkyl are independently selected from $R^{10}$;

each $R^7$, $R^9$, and $R^{10}$ is independently selected at each occurrence from:

fluorine —$OR^{30}$, —$N(R^{30})_2$, —$N(R^{30})_2$, —$C(O)R^{30}$, —$C(O)OR^{30}$, —$OC(O)R^{30}$, —$NO_2$, and —CN; $C_3$-6 carbocycle and 3- to 6-membered heterocycle each of which is optionally substituted with one or more substituents independently selected from halogen, —$OR^{31}$, —$N(R^{31})_2$, —$NO_2$, —CN, and $C_1$-3 alkyl;

and when $R^{6'}$ is —C(O)(NHMe) and $R^9$ is an optionally substituted 3- to 6-membered heterocycle, $R^9$ is optionally substituted with one or more substituents selected from one or more substituents independently selected from fluorine, bromine, —$OR^{30}$, —$N(R^{30})_2$, —$NO_2$, —CN, and $C_{1-3}$ alkyl;

each $R^8$ is independently selected at each occurrence from:

halogen, —$OR^{30}$, —$N(R^{30})_2$, —$N(R^{30})_2$, —$C(O)R^{30}$, —$C(O)OR^{30}$, —$OC(O)R^{30}$, —$NO_2$, and —CN; $C_{1-3}$ alkyl optionally substituted with one or more substituents independently selected from halogen, —$OR^{30}$, —$N(R^{30})_2$, —$NO_2$, —CN, $C_{3-6}$ carbocycle and 3- to 6-membered heterocycle;

each $R^{30}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, and 3- to 6-membered heterocycle; each $R^{50}$ is independently selected at each occurrence from hydrogen, and $C_{1-6}$ alkyl; and each $R^{31}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, 3- to 6-membered heterocycle, wherein the $C_{3-6}$ carbocycle and 3- to 6-membered heterocycle are optionally substituted with one or more substituents independently selected from halogen, —OH, —CN, —$NO_2$, —$NH_2$, —O—$C_{1-6}$ alkyl, and —$C_{1-6}$ alkyl; and $R^{12'}$ is selected from hydrogen, halogen, hydroxy, —$NO_2$, —CN, —$NH_2$, —O—$C_{1-6}$ alkyl, and $C_{1-6}$ alkyl, wherein the alkyl portion of —O—$C_{1-6}$ alkyl, and $C_{1-6}$ alkyl are optionally substituted with one or more substituents selected from halogen, —OH, —$NH_2$, —$NO_2$, —CN, —O—$C_{1-6}$ alkyl, $C_{3-6}$ carbocycle, 3- to 6-membered heterocycle; wherein the $C_{3-6}$ carbocycle, 3- to 6-membered heterocycle are each optionally substituted with one or more substituents selected from halogen, hydroxy, —$NO_2$, —CN, —$NH_2$, —O—$C_{1-6}$ alkyl, and $C_{1-6}$ alkyl.

In certain aspects, the disclosure provides a compound represented by Formula (III):

(III)

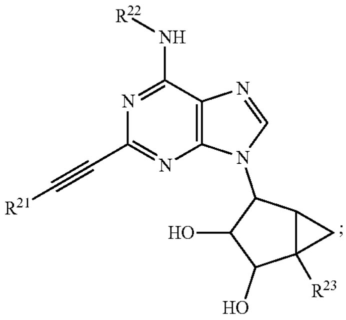

or a pharmaceutically acceptable salt thereof, wherein:

$R^{21}$ is selected from $C_3$-$C_6$ cycloalkyl and 3-6-membered heterocycloalkyl, wherein $C_3$-$C_6$ cycloalkyl and 3-6-membered heterocycloalkyl are optionally substituted with one or more substituents independently selected from $R^{29}$;

$R^{22}$ is selected from optionally substituted $C_1$-$C_6$ alkyl, optionally substituted $C_3$-$C_8$ carbocycle and optionally substituted 3 to 8-membered heterocycle, wherein optional substituents on $C_1$-$C_6$ alkyl are independently selected at each occurrence from $R^{27}$ and optional substituents on $C_3$-$C_8$ carbocycle and 3 to 8-membered heterocycle are independently selected from $R^2$;

$R^{23}$ is selected from hydrogen and optionally substituted $C_1$-$C_3$ alkyl, wherein optional substituents on $C_1$-$C_3$ alkyl are independently selected from $R^{40}$;

each $R^{27}$, $R^{29}$, and $R^{40}$ is independently selected at each occurrence from:

fluorine —$OR^{50}$, —$N(R^0)_2$, —$N(R^0)_2$, —$C(O)R^{50}$, —$C(O)OR^{50}$, —$OC(O)R^{50}$, —$NO_2$, and —CN; $C_{3-6}$ carbocycle and 3- to 6-membered heterocycle each of which is optionally substituted with one or more substituents independently selected from halogen, —$OR^{50}$, —$N(R^{50})_2$, —$NO_2$, —CN, and $C_{1-3}$ alkyl;

each $R^{28}$ is independently selected at each occurrence from:

halogen, —$OR^{50}$, —$N(R^{50})_2$, —$N(R^{50})_2$, —$C(O)R^{50}$, —$C(O)OR^{50}$, —$OC(O)R^{50}$, —$NO_2$, and —CN; $C_{1-3}$ alkyl optionally substituted with one or more substituents independently selected from halogen, —$OR^{50}$, —$N(R^{50})_2$, —$NO_2$, —CN, $C_{3-6}$ carbocycle and 3- to 6-membered heterocycle; and $R^{50}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle and 3- to 6-membered heterocycle.

In certain aspects, the disclosure provides a compound represented by Formula (IV):

(IV)

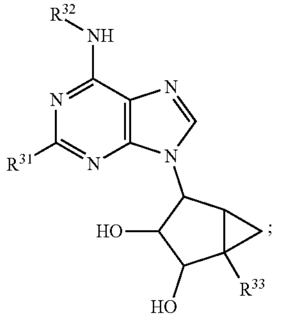

or a pharmaceutically acceptable salt thereof, wherein:

$R^{31}$ is selected from hydrogen, halogen, $C_3$-$C_6$ cycloalkyl, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted with one or more substituents independently selected from $R^{39}$.

$R^{32}$ is selected from $C_1$-$C_6$ alkyl;

$R^{33}$ is selected from $C_1$-$C_3$ haloalkyl;

each $R^{39}$ is independently selected at each occurrence from:

fluorine, —$OR^{60}$, —$N(R^{60})_2$, —$N(R^{60})_2$, —$C(O)R^{60}$, —$C(O)OR^{60}$, —$OC(O)R^{60}$, —$NO_2$, and —CN; $C_{3-6}$ carbocycle and 3- to 6-membered heterocycle each of which is optionally substituted with one or more substituents independently selected from halogen, —$OR^{60}$, —$N(R^{60})_2$, —$NO_2$, —CN, and $C_{1-3}$ alkyl;

each $R^{60}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle and 3- to 6-membered heterocycle.

In certain aspects, the disclosure provides a pharmaceutical composition comprising a compound or salt of any one of the compound described herein and a pharmaceutically acceptable excipient.

In certain aspects, the disclosure provides a method for agonizing the $A_3$ adenosine receptor comprising administering to a subject with a condition in need thereof a compound or salt described herein. In certain embodiments, the compound or salt agonizes the $A_3$ adenosine receptor by ten-fold or greater relative to agonism of the $A_1$, $A_{2A}$, and $A_{2B}$ receptors.

In certain embodiments, the disclosure provides a method of treating a condition selected from vascular inflammation, arthritis, allergies, asthma, wound healing, stroke, cardiac failure, acute spinal cord injury, acute head injury or trauma, seizure, neonatal hypoxia, cerebral palsy, chronic hypoxia due to arteriovenous malformations and occlusive cerebral artery disease, ischemia and reperfusion injury in skeletal muscle, severe neurological disorders related to excitotoxicity, Parkinson's disease, Huntington's chorea, diseases of the CNS, cardiac disease, kidney disease, glaucoma, cancer, neuropathic pain, transient ischemic attacks, myeloprotection, dry eye syndrome, osteoarthritis, rheumatoid arthritis, loss of skin pigmentation, inflammatory bowel disease, pulmonary inflammation, uveitis, and septic shock.

In certain embodiments, the disclosure provides a method of treating a condition selected from chemotherapy-induced peripheral neuropathy, diabetic peripheral neuropathy, neurodegeneration, drug-induced ototoxicity, spinocerebellar degeneration, symptoms associated with traumatic brain injury, chemotherapy-induced cognitive impairment, pain and discomfort of irritable bowel syndrome, and neuropathic pain.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

A. Definitions

Unless defined otherwise, all technical and scientific terms used herein have the same meaning as is commonly understood by one of skill in the art to which this invention belongs. All patents and publications referred to herein are incorporated by reference.

"Alkyl" refers to a straight or branched hydrocarbon chain radical consisting solely of carbon and hydrogen atoms, containing no unsaturation, and preferably having from one to fifteen carbon atoms (i.e., $C_1$-$C_{15}$ alkyl). In certain embodiments, an alkyl comprises one to thirteen carbon atoms (i.e., $C_1$-$C_{13}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond.

The term "$C_{x-y}$" when used in conjunction with a chemical moiety, such as alkyl, alkenyl, or alkynyl is meant to include groups that contain from x to y carbons in the chain. For example, the term "$C_{1-6}$alkyl" refers to substituted or unsubstituted saturated hydrocarbon groups, including straight-chain alkyl and branched-chain alkyl groups that contain from 1 to 6 carbons. The term —$C_{x-y}$alkylene- refers to a substituted or unsubstituted alkylene chain with from x to y carbons in the alkylene chain. For example —$C_{1-6}$alkylene- may be selected from methylene, ethylene, propylene, butylene, pentylene, and hexylene, any one of which is optionally substituted.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively. The term —$C_{x-y}$alkenylene-refers to a substituted or unsubstituted alkenylene chain with from x to y carbons in the alkenylene chain. For example, —$C_{2-6}$alkenylene- may be selected from ethenylene, propenylene, butenylene, pentenylene, and hexenylene, any one of which is optionally substituted. An alkenylene chain may have one double bond or more than one double bond in the alkenylene chain. The term —$C_{x-y}$alkynylene- refers to a substituted or unsubstituted alkynylene chain with from x to y carbons in the alkenylene chain. For example, —$C_{2-6}$alkenylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_8$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene).

"Aryl" refers to a radical derived from an aromatic monocyclic or aromatic multicyclic hydrocarbon ring system by removing a hydrogen atom from a ring carbon atom. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized $(4n+2)$ $\pi$-electron system in accordance with the Hückel theory. The ring system from which aryl groups are derived include, but are not limited to, groups such as benzene, fluorene, indane, indene, tetralin and naphthalene.

"Aralkyl" refers to a radical of the formula —Rc-aryl where Rc is an alkylene chain as defined above, for example, methylene, ethylene, and the like.

"Aralkenyl" refers to a radical of the formula —Rd-aryl where Rd is an alkenylene chain as defined above. "Aralkynyl" refers to a radical of the formula —Re-aryl, where Re is an alkynylene chain as defined above.

"Carbocycle" refers to a saturated, unsaturated or aromatic rings in which each atom of the ring is carbon. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. An aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl.

"Cycloalkyl" refers to a fully saturated monocyclic or polycyclic hydrocarbon radical consisting solely of carbon and hydrogen atoms, which includes fused or bridged ring systems, and preferably having from three to twelve carbon atoms. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like.

"Cycloalkenyl" refers to an unsaturated non-aromatic monocyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls includes, e.g., cyclopentenyl, cyclohexenyl, cycloheptenyl, and cyclooctenyl.

"Cycloalkylalkyl" refers to a radical of the formula —Rc-cycloalkyl where Rc is an alkylene chain as described above.

"Cycloalkylalkoxy" refers to a radical bonded through an oxygen atom of the formula —O-Rc-cycloalkyl where Rc is an alkylene chain as described above.

"Halo" or "halogen" refers to halogen substituents such as bromo, chloro, fluoro and iodo substituents.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen may be independently selected e.g., 1-chloro,2-fluoroethane.

"Fluoroalkyl" refers to an alkyl radical, as defined above, that is substituted by one or more fluoro radicals, for example, trifluoromethyl, difluoromethyl, fluoromethyl, 2,2,2-trifluoroethyl, 1-fluoromethyl-2-fluoroethyl, and the like.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. "Heterocyclene" refers to a divalent heterocycle linking the rest of the molecule to a radical group.

"Heteroaryl" or "aromatic heterocycle" refers to a radical derived from a heteroaromatic ring radical that comprises one to eleven carbon atoms and at least one heteroatom wherein each heteroatom may be selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, pyridine, pyrimidine, oxazole, furan, thiophene, benzthiazole, and imdazopyridine. An "X-membered heteroaryl" refers to the number of endocylic atoms, i.e., X, in the ring. For example, a 5-membered heteroaryl ring or 5-membered aromatic heterocycle has 5 endocyclic atoms, e.g., triazole, oxazole, thiophene, etc.

"Heterocycloalkyl" refers to a 3- to 12-membered non-aromatic ring radical that comprises two to twelve carbon atoms and at least one heteroatom wherein each heteroatom may be selected from N, O, Si, P, B, and S atoms. The heterocycloalkyl may be selected from monocyclic or bicyclic, and fused or bridged ring systems. The heteroatoms in the heterocycloalkyl radical are optionally oxidized. One or more nitrogen atoms, if present, are optionally quaternized. The heterocycloalkyl radical is partially or fully saturated. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

In some embodiments, substituents may include any substituents described herein, for example: halogen, hydroxy, oxo (=O), thioxo (=S), cyano (—CN), nitro ($—NO_2$), imino (=N—H), oximo (=N—OH), hydrazino ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2), and $—R^b—S(O)_tN(R^a)_2$ (where t is 1 or 2); and alkyl, alkenyl, alkynyl, aryl, aralkyl, aralkenyl, aralkynyl, cycloalkyl, cycloalkylalkyl, and heterocycle, any of which may be optionally substituted by alkyl, alkenyl, alkynyl, halogen, haloalkyl, haloalkenyl, haloalkynyl, oxo (=O), thioxo (=S), cyano (—CN), nitro ($—NO_2$), imino (=N—H), oximo (=N—OH), hydrazine ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)R^a$ (where t is 1 or 2), $—R^b—S(O)_tOR^a$ (where t is 1 or 2) and $—R^b—S(O)_tN(R^a)_2$ (where t is 1 or 2); wherein each $R^a$ is independently selected from hydrogen, alkyl, cycloalkyl, cycloalkylalkyl, aryl, aralkyl, and heterocycle, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro ($—NO_2$), imino (=N—H), oximo (=N—OH), hydrazine ($=N—NH_2$), $—R^b—OR^a$, $—R^b—OC(O)—R^a$, $—R^b—OC(O)—OR^a$, $—R^b—OC(O)—N(R^a)_2$, $—R^bN(R^a)_2$, $—R^b—C(O)R^a$, $—R^b—C(O)OR^a$, $—R^b—C(O)N(R^a)_2$, $—R^b—O—$ $R^a$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain.

As used in the specification and claims, the singular form "a", "an" and "the" includes plural references unless the context clearly dictates otherwise.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

B. Compounds of the Disclosure

In certain embodiments, the disclosure provides a compound represented by Formula (I):

(I)

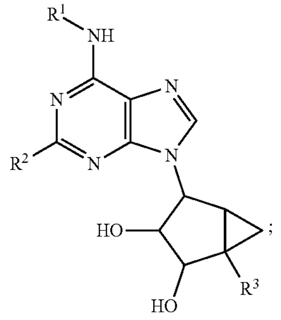

or a pharmaceutically acceptable salt thereof, wherein:

$R^1$ is selected from —$CD_3$, $C_2$ fluoroalkyl, $C_4$-$C_6$ fluoroalkyl, and $C_2$-$C_6$ alkyl substituted with phenyl, wherein the phenyl is substituted with one or more fluorine atoms;

$R^2$ is selected from hydrogen, halogen, $C_3$-$C_6$ cycloalkyl, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted with one or more substituents independently selected from R*; and $R^3$ is selected from hydrogen, $C_1$-$C_6$ alkyl, and $C_1$-$C_6$ haloalkyl; and each R* is independently selected from fluorine —O$R^{20}$, —N($R^{20}$)$_2$, —N($R^{20}$)$_2$, —C(O)$R^{20}$, —C(O)O$R^{20}$, —OC(O)$R^{20}$, —$NO_2$, and —CN; and $C_{3-6}$ carbocycle and 3- to 6-membered heterocycle each of which is optionally substituted with one or more substituents independently selected from halogen, —$OR^{20}$, —$N(R^{20})_2$, —$NO_2$, —CN, and $C_{1-3}$ alkyl; and $R^{20}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle and 3- to 6-membered heterocycle.

In some embodiments, the compound of Formula (I) is represented by Formula (IA):

(IA)

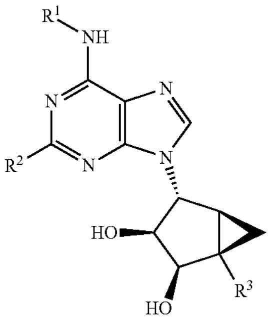

or a pharmaceutically acceptable salt thereof.

In some embodiments, for a compound or salt of Formula (I) or Formula (IA), R1 is selected from $C_2$ fluoroalkyl, $C_4$-$C_6$ fluoroalkyl, and $C_2$-$C_6$ alkyl substituted with phenyl, wherein the phenyl is substituted with one or more fluorine atoms;

In some embodiments, for a compound or salt of Formula (I) or Formula (IA), R1 is selected from $C_1$-$C_6$ alkyl, wherein the alkyl is substituted with at least one deuterium atom. In some cases, R1 is —CD3.

In some embodiments, for a compound or salt of Formula (I) or Formula (IA), $R^1$ is selected from $CH_2CFH_2$, $CH_2CF_2H$, and $CH_2CF_3$. In some cases, $R^1$ is $CH_2CF_2H$.

In some embodiments, for a compound or salt of Formula (I) or Formula (IA), when $R^2$ is selected from hydrogen, fluorine, bromine, iodine, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl wherein $C_1$-$C_6$ alkyl, $C_2$-$C_6$ alkenyl, and $C_2$-$C_6$ alkynyl are optionally substituted with one or more substituents independently selected from R*, $R^1$ is further selected from $C_3$ fluoroalkyl and $C_1$ alkyl substituted with phenyl, wherein the phenyl is substituted with one or more fluorine atoms. In some cases, when $R^2$ is not $C_1$, $R^1$ is further selected from $C_3$ fluoroalkyl and $C_1$ alkyl substituted with phenyl, wherein the phenyl is substituted with one or more fluorine atoms. In some embodiments, when $R^2$ is not $C_1$, $R^1$ is fluorobenzyl. In some embodiments, when $R^2$ is not Cl, $R^1$ is $C_3$ fluoroalkyl.

In some embodiments, for a compound or salt of Formula (I) or Formula (IA), R2 is selected from C3-C6 cycloalkyl. In some embodiments, R2 is

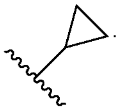 [SMILES: *C1CC1]

In some embodiments, for a compound or salt of Formula (I) or Formula (IA), $R^2$ is selected from hydrogen, $CH_3$, $CH_2CH_3$, and $C_1$. In some cases, $R^2$ is selected from $C_1$, $CH_3$,

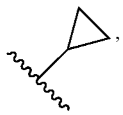

, and

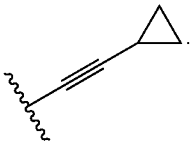

In some cases, $R^2$ is Cl. In some cases, $R^2$ is

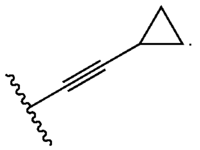 [SMILES: *C#CC1CC1]

In some cases, $R^2$ is selected from Cl, $CH_3$. In some cases, $R^2$ is selected from Cl, $CH_3$, and

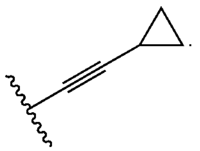 [SMILES: *C#CC1CC1]

In some embodiments, for a compound or salt of Formula (I) or Formula (IA), R3 is selected from hydrogen, CH3, CH2F, CHF2, and CF3. In some cases, R3 is hydrogen.

In another aspect, the present disclosure provides a compound represented by Formula (II'):

(II')

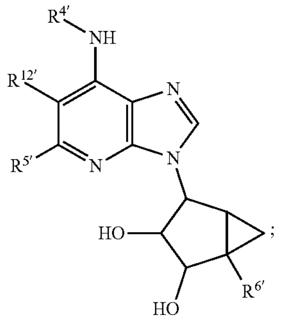

or a pharmaceutically acceptable salt thereof, wherein:

$R^{4'}$ is selected from hydrogen, optionally substituted $C_1$-$C_6$ alkyl, optionally substituted $C_3$-$C_8$ carbocycle and optionally substituted 3 to 8-membered heterocycle, wherein optional substituents on $C_1$-$C_6$ alkyl are independently selected from $R^7$ and optional substituents on $C_3$-$C_8$ carbocycle and 3 to 8-membered heterocycle are independently selected from $R^8$;

$R^{5'}$ is selected from hydrogen, —$NO_2$, —CN, —$NH_2$, halogen, $C_3$-$C_6$ cycloalkyl, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted with one or more substituents independently selected from $R^9$; $R^{6'}$ is selected from hydrogen, —C(O)($NR^{5U}2$), and optionally substituted $C_1$-$C_3$ alkyl, wherein optional substituents on $C_1$-$C_3$ alkyl are independently selected from $R^{10}$;

each $R^7$, $R^9$, and $R^{10}$ is independently selected at each occurrence from:

fluorine —$OR^{30}$, —$N(R^{30})_2$, —$N(R^{30})_2$, —$C(O)R^{30}$, —$C(O)OR^{30}$, —$OC(O)R^{30}$, —$NO_2$, and —CN; $C_{3-6}$ carbocycle and 3- to 6-membered heterocycle each of which is optionally substituted with one or more substituents independently selected from halogen, —$OR^{31}$, —$N(R^{31})_2$, —$NO_2$, —CN, and $C_1$-3 alkyl;

and when $R^{6'}$ is —C(O)(NHMe) and $R^9$ is an optionally substituted 3- to 6-membered heterocycle, $R^9$ is optionally substituted with one or more substituents selected from one or more substituents independently selected from fluorine, bromine, —$OR^{30}$, —$N(R^{30})_2$, —$NO_2$, —CN, and $C_{1-3}$ alkyl;

each $R^8$ is independently selected at each occurrence from:

halogen, —$OR^{30}$, —$N(R^{30})_2$, —$N(R^{30})_2$, —$C(O)R^{30}$, —$C(O)OR^{30}$, —$OC(O)R^{30}$, —$NO_2$, and —CN; $C_{1-3}$ alkyl optionally substituted with one or more substituents independently selected from halogen, —$OR^{30}$, —$N(R^{30})_2$, —$NO_2$, —CN, $C_{3-6}$ carbocycle and 3- to 6-membered heterocycle;

each $R^{30}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_3$-6 carbocycle, and 3- to 6-membered heterocycle;

each $R^{50}$ is independently selected at each occurrence from hydrogen, and $C_{1-6}$ alkyl; and each $R^{31}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, 3- to 6-membered heterocycle, wherein the $C_{3-6}$ carbocycle and 3- to 6-membered heterocycle are optionally substituted with one or more substituents independently selected from halogen, —OH, —CN, —$NO_2$, —$NH_2$, —O—$C_{1-6}$ alkyl, and —$C_{1-6}$ alkyl;

$R^{12'}$ is selected from hydrogen, halogen, hydroxy, —$NO_2$, —CN, —$NH_2$, —O—$C_{1-6}$ alkyl, and $C_{1-6}$ alkyl, wherein the alkyl portion of —O—$C_{1-6}$ alkyl, and $C_{1-6}$ alkyl are optionally substituted with one or more substituents selected from halogen, —OH, —$NH_2$, —$NO_2$, —CN, —O—$C_{1-6}$ alkyl, $C_{3-6}$ carbocycle, 3- to 6-membered heterocycle; wherein the $C_{3-6}$ carbocycle, 3- to 6-membered heterocycle are each optionally substituted with one or more substituents selected from halogen, hydroxy, —$NO_2$, —CN, —$NH_2$, —O—$C_{1-6}$ alkyl, and $C_{1-6}$ alkyl.

In some embodiments, the compound or salt of Formula (II') is represented by Formula (IIA'):

(IIA')

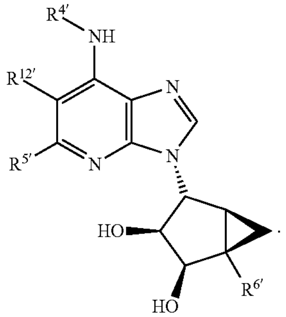

In some embodiments, for a compound or salt of Formula (II') or Formula (IIA'), $R^{4'}$ is selected from optionally substituted $C_1$-$C_6$ alkyl, optionally substituted $C_3$-$C_8$ carbocycle and optionally substituted 3 to 8-membered heterocycle, wherein optional substituents on $C_1$-$C_6$ alkyl are independently selected at each occurrence from $R^7$ and optional substituents on $C_3$-$C_8$ carbocycle and 3 to 8-membered heterocycle are independently selected from $R^8$.

In some embodiments, for a compound or salt of Formula (II') or Formula (IIA'), $R^{4'}$ is selected from optionally substituted $C_1$-$C_6$ alkyl, wherein the $C_1$-$C_6$ alkyl is optionally substituted with one or more substituents independently selected at each occurrence from fluorine; $C_3$-6 carbocycle and 3- to 6-membered heterocycle each of which is optionally substituted with one or more substituents independently selected from halogen, —OR31, —N(R31)2, —NO2, —CN, and C1-3 alkyl.

In some embodiments, for a compound or salt of Formula (II') or Formula (IIA'), $R^{4'}$ is selected from optionally substituted $C_1$-$C_6$ alkyl, wherein the $C_1$-$C_6$ alkyl is optionally substituted with one or more substituents independently selected at each occurrence from fluorine; $C_{3-6}$ carbocycle which is optionally substituted with one or more substituents independently selected from halogen, —$OR^{31}$, —$N(R^{31})_2$, —$NO_2$, —CN, and $C_{1-3}$ alkyl. In some cases, the $C_{3-6}$ carbocycle is optionally substituted with one or more substituents independently selected from halogen, —$OR^{31}$, —$N(R^{31})_2$, —$NO_2$, —CN, and $C_{1-3}$ alkyl. In some cases, the $C_{3-6}$ carbocycle is optionally substituted with one or more substituents independently selected from halogen, —$OR^{31}$, —$N(R^{31})_2$, and $C_{1-3}$ alkyl. In some cases, the $C_{3-6}$ carbocycle is optionally substituted with one or more substituents independently selected from halogen, —$OR^{31}$, and —$N(R^{31})_2$. In some cases, each $R^{31}$ is independently selected at each occurrence from $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, 3- to 6-membered heterocycle, wherein the $C_{3-6}$ carbocycle and 3- to 6-membered heterocycle are optionally substituted with one or more substituents independently selected from halogen, —OH, —CN, —$NO_2$, —$NH_2$, —O—$C_{1-6}$ alkyl, and —$C_{1-6}$ alkyl. In some cases, each $R^{31}$ is independently selected at each occurrence from $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, 3- to 6-membered heterocycle, wherein the $C_{3-6}$ carbocycle and 3- to 6-membered heterocycle are optionally substituted with one or more substituents independently selected from halogen, —OH, —CN, —$NO_2$, —$NH_2$, —O—$C_{1-6}$ alkyl, and —$C_{1-6}$ alkyl. In some cases, each $R^{31}$ is independently selected at each occurrence from $C_{1-6}$ alkyl optionally substituted with one or more substituents independently selected from 3- to 6-membered heterocycle, wherein the 3- to 6-membered heterocycle is optionally substituted with one or more substituents independently selected from —O—$C_{1-6}$ alkyl, and —$C_{1-6}$ alkyl. In some cases, each $R^{31}$ is independently selected at each occurrence from $C_{1-6}$ alkyl optionally substituted with one or more substituents independently selected from 5-membered heterocycle, wherein the 5-membered heterocycle is optionally substituted with one or more substituents independently selected from —$C_{1-6}$ alkyl.

In some embodiments, for a compound or salt of Formula (II') or Formula (IIA'), $R^{4'}$ is selected from $C_1$-$C_6$ alkyl substituted with one or more fluorine. In some cases, $R^{4'}$ is selected from $C_1$-$C_6$ alkyl substituted with one or more hydroxy. In some cases, $R^{4'}$ is selected from $C_1$-$C_6$ alkyl substituted with unsubstituted $C_{3-6}$ carbocycle. In some cases, $R^{4'}$ is selected from $C_1$-$C_6$ alkyl substituted with phenyl substituted with one or more halogen. In some cases, $R^{4'}$ is selected from $C_1$-$C_6$ alkyl substituted with phenyl substituted with one or more halogens selected from fluorine and chlorine. In some cases, $R^{4'}$ is selected from $C_1$-$C_6$ alkyl substituted with phenyl substituted with at least one or two chlorines. In some cases, $R^{4'}$ is selected from $C_1$-$C_6$ alkyl substituted with phenyl substituted with at least one or two fluorine. In some cases, $R^{4'}$ is selected from $C_1$-$C_6$ alkyl substituted with phenyl substituted with two chlorines. In some cases, $R^{4'}$ is selected from $C_1$-$C_6$ alkyl substituted with phenyl substituted with two fluorine. In some cases, $R^{4'}$ is selected from $C_1$-$C_6$ alkyl substituted with phenyl substituted with one chlorine and —$OR^{31}$. In some cases, $R^{31}$ of —$OR^1$ is $C_{1-6}$ alkyl substituted with one 5-membered heterocycle, wherein the 5-membered heterocycle is optionally substituted with one or more substituents independently selected from —$C_{1-6}$ alkyl. In some cases, the 5-membered heterocycle has at least two heteroatoms. In some cases, the 5-membered heterocycle has at most two heteroatoms. In some cases, the 5-membered heterocycle has two heteroatoms. In some cases, the heteroatoms of the 5-membered heterocycle are different.

In some embodiments, for a compound or salt of Formula (II') or Formula (IIA'), $R^{4'}$ is selected from

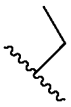
,
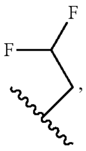
,
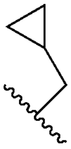
,
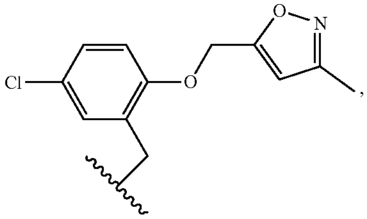
, and

-continued

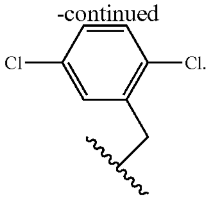

In some cases, $R^{4'}$ is

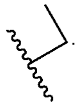

In some cases, $R^{4'}$ is

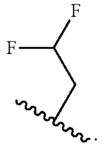

In some cases, $R^{4'}$ is

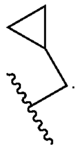

In some cases, $R^{4'}$ is

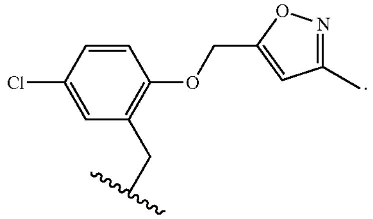 [SMILES: *Cc1cc(Cl)ccc1OCc1cc(C)no1]

In some cases, $R^{4'}$ is

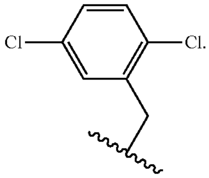 [SMILES: *Cc1cc(Cl)ccc1Cl]

In some embodiments, for a compound or salt of Formula (II') or Formula (IIA'), $R^{6'}$ is selected from hydrogen and —C(O)($NR^{50}{}_2$); $R^{5'}$ is selected from hydrogen, —$NO_2$, —CN, —$NH_2$, halogen, $C_3$-$C_6$ cycloalkyl, $C_1$-$C_6$ alkyl; $R^{12'}$ is selected from —$NO_2$, —CN, —$NH_2$, and —O—$C_{1-6}$ alkyl; and $R^{4'}$ is selected from optionally substituted $C_1$-$C_6$ alkyl, wherein the $C_1$-$C_6$ alkyl is optionally substituted with one or more substituents independently selected at each occurrence from fluorine; $C_{3-6}$ carbocycle which is optionally substituted with one or more substituents independently selected from halogen, —$OR^{31}$, —$N(R^{31})_2$, —$NO_2$, —CN, and $C_{1-3}$ alkyl. In some cases, $R^{6'}$ is —C(O)($NR^{50}{}_2$). In some cases, $R^{6'}$ is hydrogen.

In some embodiments, for a compound or salt of Formula (II') or Formula (IIA'), R4' is selected from unsubstituted C1-C6 alkyl.

In some embodiments, for a compound or salt of Formula (II') or Formula (IIA'), when R6' is —C(O)(NHMe) and R9 is an optionally substituted 3- to 6-membered heterocycle, R9 is optionally substituted with one or more substituents selected from one or more substituents independently selected from fluorine, bromine, —OR30, —N(R30)2, —NO2, —CN, and C1-3 alkyl. In some cases, when R6' is —C(O)(NHMe), R9 is not an optionally substituted 3- to 6-membered heterocycle. In some cases, when R6' is —C(O)(NHMe), R9 is not an optionally substituted 5-membered heterocycle.

In some embodiments, for a compound or salt of Formula (II') or Formula (IIA'), R4' is hydrogen.

In some embodiments, for a compound or salt of Formula (II') or Formula (IIA'), $R^{5'}$ is selected from hydrogen, —$NO_2$, —CN, —$NH_2$, halogen, $C_3$-$C_6$ cycloalkyl, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted with one or more substituents independently selected from $R^9$. In some cases, $R^{5'}$ is selected from hydrogen, $C_1$-$C_6$ alkyl, $C_3$-$C_6$ cycloalkyl, —$NO_2$, —CN, —$NH_2$, and halogen. In some cases, $R^{5'}$ is selected from $C_1$-$C_6$ alkyl, —$NO_2$, —CN, —$NH_2$, and halogen. In some cases, $R^{5'}$ is selected from —CN, and halogen.

In some embodiments, for a compound of Formula (II') or Formula (IIA'), $R^{6'}$ is selected from hydrogen and optionally substituted $C_1$-$C_3$ alkyl, wherein optional substituents on $C_1$-$C_3$ alkyl of $R^{6'}$ are independently selected from $R^{10}$.

In some embodiments, for a compound of or salt Formula (II') or Formula (IIA'), R6' is selected from hydrogen, CH3, CH2F, CHF2, and CF3. In some cases, R6' is hydrogen.

In some embodiments, for a compound of Formula (II') or Formula (IIA'), R6' is selected from —C(O)(NR502) and hydrogen. In some cases, R6' is —C(O)(NR502). In some cases, R50 is selected from hydrogen, and C1-3 alkyl. In some cases, R50 is selected from C1-3 alkyl. In some cases, R6' is —C(O)(NHMe).

In some embodiments, for a compound of or salt Formula (II') or Formula (IIA'), when R6' is —C(O)(NHMe) and R9 is an optionally substituted 3- to 6-membered heterocycle, R9 is optionally substituted with one or more substituents selected from one or more substituents independently selected from —OR30, —N(R30)2, —NO2, —CN, and C1-3 alkyl.

In some embodiments, for a compound of or salt Formula (II') or Formula (IIA'), when R6' is —C(O)(NHMe) and R9 is an optionally substituted 5-6-membered heterocycle, R9 is optionally substituted with one or more substituents selected from one or more substituents independently selected from halogen, —OR30, —N(R30)$_2$, —NO2, —CN, and C1-3 alkyl.

In some embodiments, for a compound or salt of Formula (I') or Formula (IIA'), R12' is selected from hydrogen, halogen, and unsubstituted C1-6 alkyl. In some cases, R12' is selected from fluorine and chlorine. In some cases, R12' is fluorine. In some cases, R12' is hydrogen. In some cases, R12' is selected unsubstituted C1-3 alkyl. In some cases, R12' is methyl. In some cases, R12' is selected from —NO2, —CN, —NH2, and —O—C1-6 alkyl. In some cases, R12' is selected from —NO2, —CN, and —NH2. In some cases, R12' is —CN. In some cases, R12' is selected from hydrogen, —CN, unsubstituted C1-3 alkyl.

In some embodiments, for a compound or salt of Formula (II') or Formula (IIA'), $R^{12'}$ is selected from hydrogen, halogen, hydroxy, —$NO_2$, —CN, —$NH_2$, —O—$C_{1-6}$ alkyl, and $C_{1-6}$ alkyl, wherein the alkyl portion of —O—$C_{1-6}$ alkyl, and $C_{1-6}$ alkyl are optionally substituted with one or more substituents selected from halogen, —OH, —$NH_2$, —$NO_2$, —CN, —O—$C_{1-6}$ alkyl, $C_{3-6}$ carbocycle, 3- to 6-membered heterocycle; wherein the $C_{3-6}$ carbocycle, 3- to 6-membered heterocycle are each optionally substituted with one or more substituents selected from halogen, hydroxy, —$NO_2$, —CN, —$NH_2$, —O—$C_{1-6}$ alkyl, and $C_{1-6}$ alkyl. In some cases, $R^{17'}$ is selected from hydrogen, halogen, hydroxy, —CN, —O—$C_{1-6}$ alkyl, and $C_{1-6}$ alkyl, wherein the alkyl portion of —O—$C_{1-6}$ alkyl, and $C_{1-6}$ alkyl are optionally substituted with one or more substituents selected from halogen, —OH, —CN, —O—$C_{1-6}$ alkyl, $C_{3-6}$ carbocycle, 3- to 6-membered heterocycle; wherein the $C_{3-6}$ carbocycle, 3- to 6-membered heterocycle are each optionally substituted with one or more substituents selected from halogen, hydroxy, —$NO_2$, —CN, —$NH_2$, —O—$C_{1-6}$ alkyl, and $C_{1-6}$ alkyl. In some cases, $R^{12'}$ is

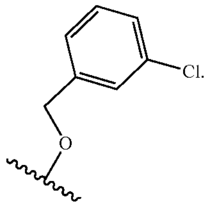 [SMILES: *OCc1cccc(Cl)c1]

In some embodiments, for a compound of Formula (II') or Formula (IIA'), $R^{6'}$ is selected from hydrogen, and optionally substituted $C_1$-$C_3$ alkyl, wherein optional substituents on $C_1$-$C_3$ alkyl are independently selected from $R^{10}$.

In some embodiments, for a compound or salt of Formula (II') or Formula (IIA'), each $R^7$, $R^9$, and $R^{10}$ is independently selected at each occurrence from:

fluorine, —$OR^{30}$, —$N(R^{30})_2$, —$N(R^{30})_2$, —$C(O)R^{30}$, —$C(O)OR^{30}$, —$OC(O)R^{30}$, —$NO_2$, and —CN; and $C_{3-6}$ carbocycle and 3- to 6-membered heterocycle each of which is optionally substituted with one or more substituents independently selected from halogen, —$OR^{30}$, —$N(R^{30})_2$, —$NO_2$, —CN, and $C_{1-3}$ alkyl.

In some embodiments, for a compound or salt of Formula (II') or Formula (IIA'), each $R^7$, $R^9$, and $R^{10}$ is independently selected at each occurrence from: fluorine, —$OR^{30}$, —$N(R^{30})_2$, —$NO_2$, and —CN; and $C_{3-6}$ carbocycle and 3- to 6-membered heterocycle each of which is optionally substituted with one or more substituents independently selected from halogen, —$OR^{30}$, —$N(R^{30})_2$, —$NO_2$, —CN, and $C_{1-3}$ alkyl.

In some embodiments, Formula (II') is represented by Formula (II):

(II)

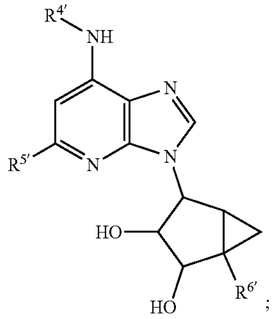

or a pharmaceutically acceptable salt thereof, wherein:

$R^{4'}$ is selected from optionally substituted $C_1$-$C_6$ alkyl, optionally substituted $C_3$-$C_8$ carbocycle and optionally substituted 3 to 8-membered heterocycle, wherein optional substituents on $C_1$-$C_6$ alkyl are independently selected from $R^7$ and optional substituents on $C_3$-$C_8$ carbocycle and 3 to 8-membered heterocycle are independently selected from $R^8$;

$R^{5'}$ is selected from hydrogen, halogen, $C_3$-$C_6$ cycloalkyl, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted with one or more substituents independently selected from $R^9$;

$R^{6'}$ is selected from hydrogen and optionally substituted $C_1$-$C_3$ alkyl, wherein optional substituents on $C_1$-$C_3$ alkyl are independently selected from $R^{10}$;

each $R^7$, $R^9$, and $R^{10}$ is independently selected at each occurrence from:

fluorine —$OR^{30}$, —$N(R^{30})_2$, —$N(R^{30})_2$, —$C(O)R^{30}$, —$C(O)OR^{30}$, —$OC(O)R^{30}$, —$NO_2$, and —CN; $C_{3-6}$ carbocycle and 3- to 6-membered heterocycle each of which is optionally substituted with one or more substituents independently selected from halogen, —$OR^{30}$, —$N(R^{30})_2$, —$NO_2$, —CN, and $C_{1-3}$ alkyl;

each $R^8$ is independently selected at each occurrence from:

halogen, —$OR^{30}$, —$N(R^{30})_2$, —$N(R^{30})_2$, —$C(O)R^{30}$, —$C(O)OR^{30}$, —$OC(O)R^{30}$, —$NO_2$, and —CN; $C_{1-3}$ alkyl optionally substituted with one or more substituents independently selected from halogen, —$OR^{30}$, —$N(R^{30})_2$, —$NO_2$, —CN, $C_{3-6}$ carbocycle and 3- to 6-membered heterocycle; and each $R^{30}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle and 3- to 6-membered heterocycle.

In some embodiments, for a compound or salt of Formula (II'), Formula (II), Formula (IIA'), or Formula (IIA), $R^{4'}$ is selected from $C_3$-$C_6$ carbocycle and optionally substituted $C_1$-$C_6$ alkyl wherein optional substituents on $C_1$-$C_6$ alkyl are independently selected at each occurrence from R7.

In some embodiments, for a compound or salt of Formula (H') or Formula (IIA), R7 is selected from fluorine, —$NO_2$, and —CN; and $C_{3-6}$ carbocycle, wherein the $C_{3-6}$ carbocycle is optionally substituted with one or more substituents independently selected from halogen, —$NO_2$, —CN, and $C_{1-3}$ alkyl.

In some embodiments, the compound or salt of Formula (II') is represented by Formula (IIA):

(IIA)

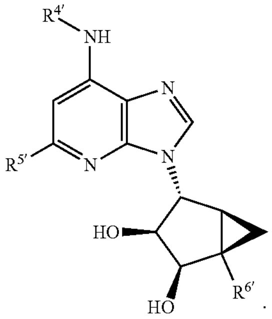

In some embodiments, for a compound or salt of Formula (II'), Formula (II), Formula (IIA'), or Formula (IIA), $R^{4'}$ is selected from optionally substituted $C_{1-2}$ alkyl and optionally substituted $C_3$-$C_6$ carbocycle. In some cases, $R^{4'}$ is an optionally substituted $C_1$ alkyl. In some cases, $R^{4'}$ is an optionally substituted $C_2$ alkyl. In some cases, $R^{4'}$ is ethyl. In some cases, the optional substituents of the $C_{1-2}$ alkyl are independently selected at each occurrence from $R^7$.

In some embodiments, for a compound or salt of Formula (II'), Formula (II), Formula (IIA'), or Formula (IIA), $R^7$ is independently selected at each occurrence from fluorine —$OR^{30}$, —$N(R^{30})_2$, —$N(R^{30})_2$, —$NO_2$, —CN; and $C_{3-6}$ carbocycle each of which is optionally substituted with one or more substituents independently selected from halogen, —$OR^{30}$, —$N(R^{30})_2$, —$NO_2$, —CN, $C_{1-3}$ alkyl. In some cases, $R^7$ is selected from fluorine and optionally substituted phenyl. In some cases, $R^{4'}$ is selected from $C_1$ alkyl substituted with one $R^7$, wherein $R^7$ is optionally substituted phenyl; and $C_2$ alkyl substituted with one or more $R^7$, wherein $R^7$ is fluorine. In some cases, $R^{4'}$ is $C_2$ alkyl substituted with one or more $R^7$, wherein $R^7$ is fluorine. In some cases, $R^{4'}$ is $C_2$ alkyl substituted with at most three $R^7$, wherein $R^7$ is fluorine. In some cases, $R^{4'}$ is $C_1$ alkyl substituted with one $R^7$, wherein $R^7$ is optionally substituted phenyl. In some cases, the optional substituents of the phenyl of $R^7$ are independently selected at each occurrence from halogen, —$OR^{30}$, —$N(R^{30})_2$, —$NO_2$, —CN, $C_{1-3}$ alkyl. In some cases, $R^7$ is substituted phenyl. In some cases, the phenyl of $R^7$ is substituted with one or more fluorine atoms. In some cases, the phenyl of $R^1$ is substituted with two fluorine atoms. In some cases, $R^{4'}$ is selected from $CH_2CH_3$, $CH_2CFH_2$, $CH_2CF_2H$, $CH_2CF_3$,

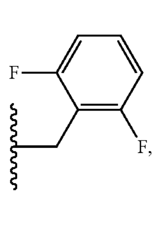, 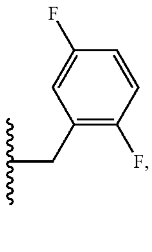, and 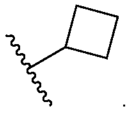.

In some embodiments, for a compound or salt of Formula (II'), Formula (II), Formula (IIA'), or Formula (IIA), $R^{5'}$ is selected from hydrogen, $CH_3$, $CH_2CH_3$,

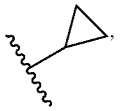 [SMILES: *C1CC1]

and Cl. In some embodiments, $R^{5'}$ is selected from hydrogen, $CH_3$, $CH_2CH_3$, and $C_1$. In some cases, $R^{5'}$ is selected from hydrogen, $CH_3$, and Cl. In some cases, $R^{5'}$ is Cl. In some cases, $R^{5'}$ is

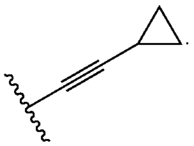 [SMILES: *C#CC1CC1]

In some embodiments, for a compound of Formula (II'), Formula (II), Formula (IIA'), or Formula (IIA), $R^{6'}$ is selected from hydrogen, $CH_3$, $CH_2F$, $CHF_2$, and $CF_3$. In some cases, $R^{6'}$ is hydrogen.

In some embodiments, for a compound or salt of Formula (II') or Formula (IIA'), $R^{4'}$ is selected from hydrogen, and optionally substituted $C_1$-$C_6$ alkyl, wherein optional substituents on $C_1$-$C_6$ alkyl are independently selected from $R^7$;

$R^{5'}$ is selected from —CN, halogen, $C_3$-$C_6$ cycloalkyl, and $C_1$-$C_6$ alkyl, wherein $C_1$-$C_6$ alkyl, are optionally substituted with one or more substituents independently selected from $R^9$;

$R^{6'}$ is selected from hydrogen, and —C(O)($NR^{50}{}_2$;

each $R^7$ is independently selected at each occurrence from:

fluorine, —$OR^{30}$; and $C_{3-6}$ carbocycle which is optionally substituted with one or more substituents independently selected from halogen, —$OR^{31}$, —$N(R^{31})_2$, —$NO_2$, —CN, and $C_{1-3}$ alkyl;

each $R^9$ is independently selected at each occurrence from:

fluorine, —$OR^{30}$, —$N(R^{30})_2$, —$NO_2$, and —CN; and $C_{3-6}$ carbocycle which is optionally substituted with one or more substituents independently selected from halogen, —$OR^{31}$, —$N(R^{31})_2$, —$NO_2$, —CN, and $C_{1-3}$ alkyl;

each $R^{30}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, and 3- to 6-membered heterocycle;

each $R^{50}$ is independently selected at each occurrence from hydrogen, and $C_{1-6}$ alkyl;

each $R^{31}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, 3- to 6-membered heterocycle, wherein the $C_{3-6}$ carbocycle and 3- to 6-membered heterocycle are optionally substituted with one or more substituents independently selected from halogen, —OH, —CN, —$NO_2$, —$NH_2$, —O—$C_{1-6}$ alkyl, and —$C_{1-6}$ alkyl; and $R^{12'}$ is selected from hydrogen, halogen, hydroxy, —$NO_2$, —CN, —$NH_2$, —O—$C_{1-6}$ alkyl, and $C_{1-6}$ alkyl, wherein the alkyl portion of —O—$C_{1-6}$ alkyl, and $C_{1-6}$ alkyl are optionally substituted with one or more substituents selected from halogen, —OH, —$NH_2$, —$NO_2$, —CN, $C_{3-6}$ carbocycle, 3- to 6-membered heterocycle; wherein the $C_{3-6}$ carbocycle, and 3- to 6-membered heterocycle are each optionally substituted with one or more substituents selected from halogen, hydroxy, —$NO_2$, —CN, —$NH_2$, —O—$C_{1-6}$ alkyl, and $C_{1-6}$ alkyl.

In another aspect, the present disclosure provides a compound represented by Formula (III)

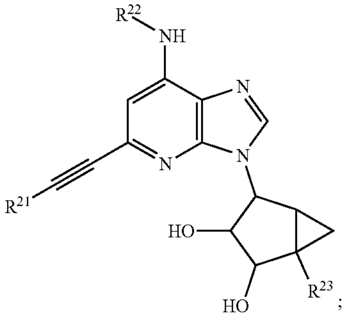

or a pharmaceutically acceptable salt thereof, wherein:

$R^{21}$ is selected from $C_3$-$C_6$ cycloalkyl and 3-6-membered heterocycloalkyl, wherein $C_3$-$C_6$ cycloalkyl and 3-6-membered heterocycloalkyl are optionally substituted with one or more substituents independently selected from $R^{29}$;

$R^{22}$ is selected from optionally substituted $C_1$-$C_6$ alkyl, optionally substituted $C_3$-$C_8$ carbocycle and optionally substituted 3 to 8-membered heterocycle, wherein optional substituents on $C_1$-$C_6$ alkyl are independently selected at each occurrence from $R^{27}$ and optional substituents on $C_3$-$C_8$ carbocycle and 3 to 8-membered heterocycle are independently selected from $R^{28}$;

$R^{23}$ is selected from hydrogen and optionally substituted $C_1$-$C_3$ alkyl, wherein optional substituents on $C_1$-$C_3$ alkyl are independently selected from $R^{40}$;

each $R^{27}$, $R^{29}$, and 4 is independently selected at each occurrence from:

fluorine —$OR^{50}$, —$N(R^{50})_2$, —$N(R^{50})_2$, —$C(O)R^{50}$, —$C(O)OR^{50}$, —$OC(O)R^{50}$, —$NO_2$, and —CN; $C_{3-6}$ carbocycle and 3- to 6-membered heterocycle each of which is optionally substituted with one or more substituents independently selected from halogen, —$OR^{50}$, —$N(R^{50})_2$, —$NO_2$, —CN, and $C_{1-3}$ alkyl;

each $R^{28}$ is independently selected at each occurrence from:

halogen, —$OR^{50}$, —$N(R^{50})_2$, —$N(R^{50})_2$, —$C(O)R^{50}$, —$C(O)OR^{50}$, —$OC(O)R^{50}$, —$NO_2$, and —CN; $C_{1-3}$ alkyl optionally substituted with one or more substituents independently selected from halogen, —$OR^{50}$, —$N(R^{50})_2$, —$NO_2$, —CN, $C_{3-6}$ carbocycle and 3- to 6-membered heterocycle; and $R^{50}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle and 3- to 6-membered heterocycle.

In some embodiments, the compound of Formula (III) is represented by Formula (IIIA):

(IIIA)

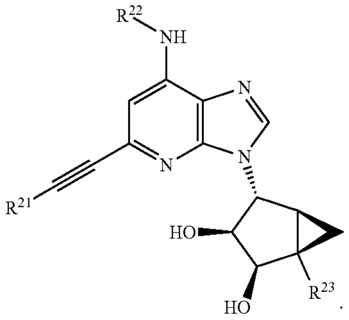

In some embodiments, $R^{21}$ is selected from $C_3$-$C_6$ cycloalkyl. In some cases, $R^{21}$ is selected from $C_3$ cycloalkyl.

In some embodiments, $R^{22}$ is selected from optionally substituted $C_1$-$C_6$ alkyl. In some cases, $R^{22}$ is selected from unsubstituted $C_1$-$C_6$ alkyl.

In some embodiments, each $R^{27}$ is independently selected from selected from —$OR^0$, —$N(R^{50})_2$, —$N(R^{50})_2$, —$C(O)R^{50}$, —$C(O)OR^{50}$, —$OC(O)R^{50}$, —$NO_2$, and —CN; $C_{3-6}$ carbocycle and 3- to 6-membered heterocycle each of which is optionally substituted with one or more substituents independently selected from —$OR^{50}$, —$N(R^{50})_2$, —$NO_2$, —CN, and $C_{1-3}$ alkyl. In some cases, each $R^{50}$ is independently selected at each occurrence from hydrogen and $C_{1-6}$ alkyl.

In some cases, $R^{23}$ is selected from hydrogen, CH3, CH2F, CHF2, and CF3.

In another aspect, the present disclosure provides a compound represented by Formula (IV):

(IV)

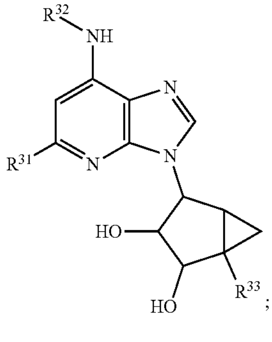

or a pharmaceutically acceptable salt thereof, wherein:

$R^{31}$ is selected from hydrogen, halogen, $C_3$-$C_6$ cycloalkyl, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted with one or more substituents independently selected from $R^{39}$;

$R^{32}$ is selected from $C_1$-$C_6$ alkyl;

$R^{33}$ is selected from $C_1$-$C_3$ haloalkyl;

each $R^{39}$ is independently selected at each occurrence from:

fluorine, —$OR^{60}$, —$N(R^{60})_2$, —$N(R^{60})_2$, —$C(O)R^{60}$, —$C(O)OR^{60}$, —$OC(O)R^{60}$, —$NO_2$, and —CN; $C_{3-6}$ carbocycle and 3- to 6-membered heterocycle each of which is optionally substituted with one or more substituents independently selected from halogen, —$OR^{60}$, —$N(R^{60})_2$, —$NO_2$, —CN, and $C_{1-3}$ alkyl;

each $R^0$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle and 3- to 6-membered heterocycle.

In some embodiments, the compound of Formula (IV) is represented by Formula (IVA):

(IVA)

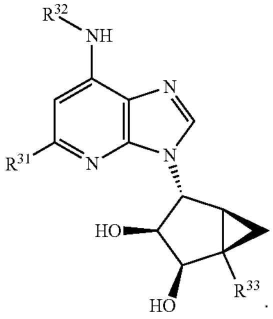

In some embodiments, for a compound of Formula (IV) or Formula (IVA), $R^{31}$ is selected from hydrogen, $CH_3$, $CH_2CH_3$, Cl,

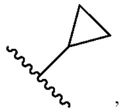

, and

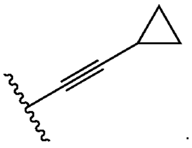

.

In some embodiments, $R^{31}$ is selected from hydrogen, $CH_3$, $CH_2CH_3$, Cl, and

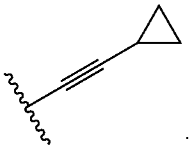 [SMILES: *C#CC1CC1]

.

In some cases, $R^{31}$ is selected from Cl.

In some embodiments, for a compound of Formula (IV) or Formula (IVA), R32 is ethyl.

In some embodiments, for a compound of Formula (IV) or Formula (IVA), $R^{33}$ is selected from $C_1$-$C_3$ fluoroalkyl. In some cases, $R^{33}$ is

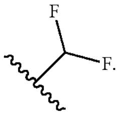 [SMILES: *C(F)F]

Included in the present disclosure are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

example, deuterium ($^{2}H$), tritium (3H), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

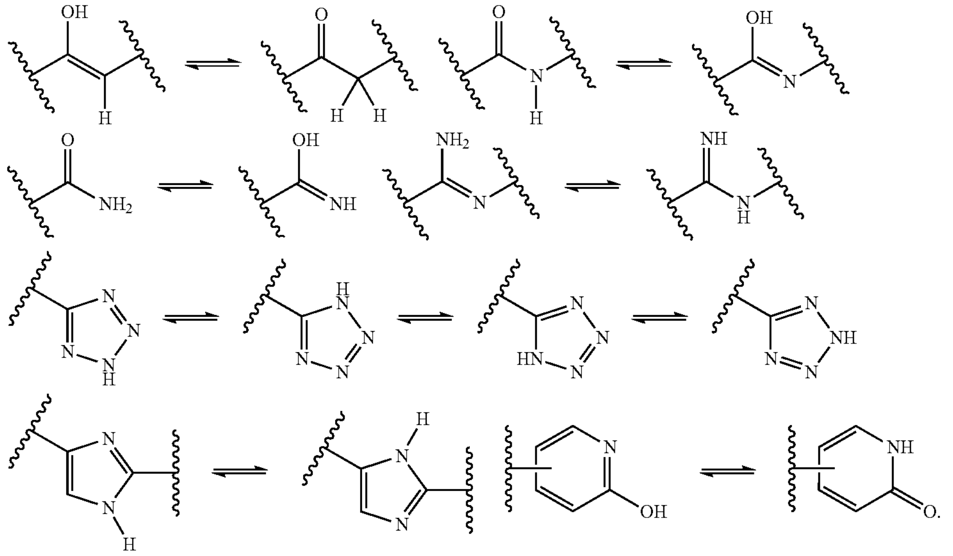

The compounds disclosed herein, in some embodiments, are used in different enriched isotopic forms, e.g., enriched in the content of $^{2}H$, $^{3}H$, $^{13}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may in some cases exist as diastereomers, enantiomers, or other stereoisomeric forms. Where absolute stereochemistry is not specified, the compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.,* 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

C. Pharmaceutical Compositions

Provided herein, in certain embodiments, are compositions comprising a therapeutically effective amount of any compound or salt of any one of Formulas (I) and (II) (also referred to herein as "a pharmaceutical agent").

Pharmaceutical compositions may be formulated using one or more physiologically acceptable carriers including excipients and auxiliaries which facilitate processing of the pharmaceutical agent into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

The compositions and methods of the present disclosure may be utilized to treat an individual in need thereof. In certain embodiments, the individual is a mammal such as a human, or a non-human mammal. When administered to an animal, such as a human, the composition or the pharmaceutical agent, is preferably administered as a pharmaceutical composition comprising, for example, a pharmaceutical agent and a pharmaceutically acceptable carrier or excipient. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration, e.g., routes, such as injection or implantation, that circumvent transport or diffusion through an epithelial barrier, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule, granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable excipient can contain physiologically acceptable agents that act, for example, to stabilize, increase solubility or to increase the absorption of a compound such as a pharmaceutical agent. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable excipient, including a physiologically acceptable agent, depends, for example, on the route of administration of the composition. The preparation or pharmaceutical composition can be a self emulsifying drug delivery system or a self microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally, for example, drenches as in aqueous or non-aqueous solutions or suspensions, tablets, capsules, including sprinkle capsules and gelatin capsules, boluses, powders, granules, pastes for application to the tongue; absorption through the oral mucosa, e.g., sublingually; anally, rectally or vaginally, for example, as a pessary, cream or foam; parenterally, including intramuscularly, intravenously, subcutaneously or intrathecally as, for example, a sterile solution or suspension; nasally; intraperitoneally; subcutaneously; transdermally, for example, as a patch applied to the skin; and topically, for example, as a cream, ointment or spray applied to the skin, or as an eye drop. The compound may also be formulated for inhalation. In certain embodiments, a compound may be simply dissolved or suspended in sterile water.

A pharmaceutical composition may be a sterile aqueous or non-aqueous solution, suspension or emulsion, e.g., a microemulsion. The excipients described herein are examples and are in no way limiting. An effective amount or therapeutically effective amount refers to an amount of the one or more pharmaceutical agents administered to a subject, either as a single dose or as part of a series of doses, which is effective to produce a desired therapeutic effect.

Subjects may generally be monitored for therapeutic effectiveness using assays and methods suitable for the condition being treated, which assays will be familiar to those having ordinary skill in the art and are described herein. Pharmacokinetics of a pharmaceutical agent, or one or more metabolites thereof, that is administered to a subject may be monitored by determining the level of the pharmaceutical agent or metabolite in a biological fluid, for example, in the blood, blood fraction, e.g., serum, and/or in the urine, and/or other biological sample or biological tissue from the subject. Any method practiced in the art and described herein to detect the agent may be used to measure the level of the pharmaceutical agent or metabolite during a treatment course.

The dose of a pharmaceutical agent described herein for treating a disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of pharmaceutical agent for treating a disease or disorder, suitable duration and frequency of administration of the pharmaceutical agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a pharmaceutical agent, including when administered for prophylactic benefit, described herein are well within the skill of a person skilled in the relevant art. When two or more pharmaceutical agents are administered to treat a disease or disorder, the optimal dose of each pharmaceutical agent may be different, such as less than when either agent is administered alone as a single agent therapy. In certain particular embodiments, two pharmaceutical agents in combination may act synergistically or additively, and either agent may be used in a lesser amount than if administered alone. An amount of a pharmaceutical agent that may be administered per day may be, for example, between about 0.01 mg/kg and 100 mg/kg, e.g., between about 0.1 to 1 mg/kg, between about 1 to 10 mg/kg, between about 10-50 mg/kg, between about 50-100 mg/kg body weight. In other embodiments, the amount of a pharmaceutical agent that may be administered per day is between about 0.01 mg/kg and 1000 mg/kg, between about 100-500 mg/kg, or between about 500-1000 mg/kg body weight. The optimal dose, per day or per course of treatment, may be different for the disease or disorder to be treated and may also vary with the administrative route and therapeutic regimen.

Pharmaceutical compositions comprising a pharmaceutical agent can be formulated in a manner appropriate for the delivery method by using techniques routinely practiced in the art. The composition may be in the form of a solid, e.g., tablet, capsule, semi-solid, e.g., gel, liquid, or gas, e.g., aerosol. In other embodiments, the pharmaceutical composition is administered as a bolus infusion.

Pharmaceutical acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the pharmaceutical agent(s) of the composition upon administration. In other embodiments, the pharmaceutical agent may be encapsulated within liposomes using technology known and practiced in the art. In certain particular embodiments, a pharmaceutical agent is not formulated within liposomes for application to a stent that is used for treating highly, though not totally, occluded arteries. Pharmaceutical compositions may be formulated for any appropriate manner of administration described herein and in the art.

A pharmaceutical composition, e.g., for oral administration or for injection, infusion, subcutaneous delivery, intramuscular delivery, intraperitoneal delivery or other method, may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the pharmaceutical agents described herein can be used alone or in combination with appropriate additives to make tablets, powders, granules or capsules, and if desired, with diluents, buffering agents, moistening agents, preservatives, coloring agents, and flavoring agents. The pharmaceutical agents may be formulated with a buffering agent to provide for protection of the compound from low pH of the gastric environment and/or an enteric coating. A pharmaceutical agent included in a pharmaceutical composition may be formulated for oral delivery with a flavoring agent, e.g., in a liquid, solid or semi-solid formulation and/or with an enteric coating.

A pharmaceutical composition comprising any one of the pharmaceutical agents described herein may be formulated for sustained or slow release, also called timed release or controlled release. Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of pharmaceutical agent contained within a sustained release formulation depends upon the site of implantation, the rate and expected duration of release, and the nature of the condition, disease or disorder to be treated or prevented.

In certain embodiments, the pharmaceutical compositions comprising a pharmaceutical agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated, e.g., intradermally or subcutaneously. The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a pharmaceutical agent can be formulated as emulsions for topical application. An emulsion contains one liquid distributed in the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the pharmaceutical agent described herein can be formulated as in inhalant. Inhaled methods can deliver medication directly to the airway. The pharmaceutical agent can be formulated as aerosols, microspheres, liposomes, or nanoparticles. The pharmaceutical agent can be formulated with solvents, gases, nitrates, or any combinations thereof. Compositions described herein are optionally formulated for delivery as a liquid aerosol or inhalable dry powder. Liquid aerosol formulations are optionally nebulized predominantly into particle sizes that can be delivered to the terminal and respiratory bronchioles. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of aerosol particles having with a mass medium average diameter predominantly between 1 to 5μ. Further, the formulation preferably has balanced osmolarity ionic strength and chloride concentration, and the smallest aerosolizable volume able to deliver effective dose of the pharmaceutical agent. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5 g. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, California), Sidestream® nebulizers (Medic-Aid Ltd., West Sussex, England), Pari LC® and Pari LC Star® jet nebulizers (Pari Respiratory Equipment, Inc., Richmond, Virginia), and Aerosonic™ (DeVilbiss Medizinische Produkte (Deutschland) GmbH, Heiden, Germany) and UltraAire® (Omron Healthcare, Inc., Vernon Hills, Illinois) ultrasonic nebulizers.

In some embodiments, the pharmaceutical agent(s) can be formulated with oleaginous bases or ointments to form a semisolid composition with a desired shape. In addition to the pharmaceutical agent, these semisolid compositions can contain dissolved and/or suspended bactericidal agents, preservatives and/or a buffer system. A petrolatum component that may be included may be any paraffin ranging in viscosity from mineral oil that incorporates isobutylene, colloidal silica, or stearate salts to paraffin waxes. Absorption bases can be used with an oleaginous system. Additives may include cholesterol, lanolin (lanolin derivatives, beeswax, fatty alcohols, wool wax alcohols, low HLB (hydrophobel-lipophobe balance) emulsifiers, and assorted ionic and nonionic surfactants, singularly or in combination.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the pharmaceutical agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) may also comprise a water insoluble polymer. Rate controlling polymers may be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the pharmaceutical agent. The matrices can be formed by solvent evaporation, spray drying, solvent extraction and other methods known to those skilled in the art.

Kits with unit doses of one or more of the agents described herein, usually in oral or injectable doses, are provided. Such kits may include a container containing the unit dose, an informational package insert describing the use and attendant benefits of the drugs in treating disease, and optionally an appliance or device for delivery of the composition.

D. Methods of Treatment

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated.

In general, however, doses employed for adult human treatment will typically be in the range of about 0.02—about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

In certain embodiments, the invention provides a method of treating or preventing a disease, state or condition in a patient in need thereof comprising administering to the patient an effective amount of a compound of any one of embodiments of the invention or a pharmaceutically acceptable salt thereof. The disease, state or condition may be selected from the group consisting of neuropathic pain, vascular inflammation, arthritis, allergies, asthma, wound healing, stroke, cardiac failure, acute spinal cord injury, acute head injury or trauma, seizure, neonatal hypoxia, cerebral palsy, chronic hypoxia due to arteriovenous malformations and occlusive cerebral artery disease, ischemia and reperfusion injury in skeletal muscle, severe neurological disorders related to excitotoxicity, Parkinson's disease, Huntington's chorea, diseases of the CNS, cardiac disease, kidney disease, glaucoma, cancer, neuropathic pain, neuropathic pain associated with diabetes, transient ischemic attacks, myeloprotection, dry eye syndrome, osteoarthritis, rheumatoid arthritis, loss of skin pigmentation, inflammatory bowel disease, pulmonary inflammation, uveitis, and septic shock. In a preferred embodiment, the invention provides a method of treating or preventing neuropathic pain in a patient in need thereof. In another preferred embodiment, the invention provides a method of treating or preventing post-operative pain in a patient in need thereof.

In certain embodiments, the disclosure provides a method of treating a condition selected from chronic inflammatory conditions, chronic neuropathic pain and mixed-pain conditions, neurodegenerative conditions, cognitive impairment conditions, the unwanted side-effects of opioid analgesic therapy, congestive heart failure, myocarditis, giant cell arteritis, temporal arteritis, aortic (Takayasu's) arteritis, vasculitis, atherosclerotic vascular lesions, chronic bronchitis, chronic pancreatitis, hepatic steatohepatitis (including alcoholic and non-alcoholic types), inflammatory bowel disease (including Crohn's disease and ulcerative colitis), inflammatory bowel syndrome, cholangitis, cholecystitis, interstitial cystitis, duodenitis, lymphadenitis, prostatitis, salpingitis, arthritis (including osteoarthritis and rheumatoid arthritis), temporomandibular joint dysfunction, myositis (including polymyositis and dermatomyositis), osteitis (including periostitis and osteomyelitis), macular degeneration (wet and dry types), glaucoma, uveitis, iritis, dry eye syndrome, and ototoxicity (deafness, hyperacusia and vestibular dysfunction) induced by drugs (including, but not limited to, platinum-containing chemotherapeutics, aminoglycoside antibiotics and loop diuretics) and noise, trigeminal neuralgia, post-traumatic painful neuropathy (causalgia and complex regional pain syndrome), post-herpetic neuralgia, diabetic neuropathy, small fiber neuropathy, burning mouth syndrome (glossodynia), vulvodynia (including vulvovestibulitis), chemotherapy-induced peripheral neuropathy (including but not limited to neuropathy caused by chemotherapeutics in the *vinca* alkaloid, taxane, platinum-containing, and proteasome-inhibitor classes), spinal cord injury pain, chronic low-back pain, chronic neck pain, sciatica, discogenic pain, fibromyalgia, Alzheimer's disease, Parkinson's disease, Huntington's disease, amyotrophic lateral sclerosis, Leber's optic neuropathy, frontotemporal dementia, dementia with Lewy bodies (DLB), spinocerebellar degeneration, multiple sclerosis, diabetic neuropathy, small fiber neuropathy, chemotherapy-induced neuropathy, traumatic brain injury (including concussions), post-operative cognitive dysfunction, chemotherapy-induced or radiation-induced damage to the oral and gastrointestinal mucosa (mucositis), hepatocellular carcinoma, adverse effects due to anti-cancer drugs, overactive bladder, pelvic pain, prostadynia, interstitial cystitis, septic shock, erectile dysfunction, acne, dynamic wrinkles and psoriasis.

In certain embodiments, the disclosure provides a method of treating a condition selected from locomotor hyperactivity, hypertension, acute hypoxia, depression, and infertility.

In certain embodiments, the disclosure provides a method of treating a condition selected from inflammatory disorders, such as vascular inflammation and arthritis, allergies, asthma, wound healing, stroke, cardiac failure, acute spinal cord injury, acute head injury or trauma, seizure, neonatal hypoxia (cerebral palsy; prophylactic treatment involves chronic exposure through placental circulation), chronic hypoxia due to arteriovenous malformations and occlusive cerebral artery disease, ischemia and reperfusion injury in skeletal muscle, severe neurological disorders related to excitotoxicity, Parkinson's disease, Huntington's chorea, and other diseases of the CNS, cardiac disease, kidney disease, and contraception.

In certain embodiments, the compounds of the invention may also be used to treat pain associated with chemotherapy-induced peripheral neuropathy (CIPN) induced by one or more combinations comprising a chemotherapeutic drug as part of a treatment regimen. Non-limiting examples of combinations include CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); ChIVPP (chlorambucil, vinblastine, procarbazine, and prednisone); IMVP-16 (ifosfamide, methotrexate, and etoposide); NIU-VIE (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylpredisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

In certain embodiments, the method comprises administering to a subject a first amount of a compound or salt described herein in combination with a second amount of analgesic, wherein the first and second amount together comprise a pharmaceutically effective amount. The first amount, the second amount, or both may be less than effective amounts of each compound administered as monotherapies. Therapeutically effective amounts of the compound of the invention and analgesic may be administered to the subject simultaneously or separately, in any given order and by the same or different routes of administration. It may be advantageous to initiate administration of the compound of the invention first, for example one or more days or weeks prior to initiation of administration of the analgesic. Moreover, additional drugs may be given in conjunction with the above combination therapy. In certain embodiments, the present disclosure provides a method of treating or preventing chemotherapy-induced peripheral neuropathy (CIPN) in a subject comprising administering to the subject a compound, salt, or pharmaceutical composition described herein. In some embodiments, the CIPN is due to anti-cancer chemotherapy. In some cases, the anti-cancer chemotherapy is a taxane chemotherapeutic, a platinum-complex chemotherapeutic, a *vinca* alkaloid chemotherapeutic, or a proteasome inhibitor chemotherapeutic. In some cases, CIPN is due to anti-viral chemotherapy In some cases, the anti-viral chemotherapy is an anti-HIV chemotherapy.

In certain embodiments, the present disclosure provides a method of treating or preventing diabetic peripheral neuropathy in a subject comprising administering to the subject a compound, salt, or pharmaceutical composition as described herein.

In certain embodiments, the present disclosure provides a method of treating or preventing neurodegeneration in a subject comprising administering to the subject a compound, salt, or pharmaceutical composition as described herein. In some cases, the neurodegeneration is due to Alzheimer's disease, Parkinson's disease, Huntington's disease, amyotrophic lateral sclerosis, or Leber's optic neuropathy.

In certain embodiments, the present disclosure provides a method of preventing or treating drug-induced ototoxicity in a subject comprising administering to the subject a compound, salt, or pharmaceutical composition described herein. In some embodiments, the drug-induced ototoxicity is deafness, tinnitus, or hyperacusia.

In certain embodiments, the present disclosure provides a method of treating or preventing spinocerebellar degeneration in a subject comprising administering to the subject a compound, salt, or pharmaceutical composition described herein.

In certain embodiments, the present disclosure provides method for treating or preventing symptoms associated with traumatic brain injury in a subject in need thereof, comprising administering to the subject a compound, salt, or pharmaceutical composition described herein. In some cases, the method comprises treating one or more symptoms associated with traumatic brain injury. In some cases, the one or more symptoms is cognitive impairment. In some cases, the cognitive impairment comprises at least one of the following: memory loss, disrupted insight, judgement, and thought, reduced processing speed, distractibility and/or deficits in executive functions such as abstract reasoning, planning, problem-solving, and multi-tasking. In some cases, the compound, salt, or pharmaceutical composition is administered within 24 hours of a traumatic brain injury or within 48 hours of a traumatic brain injury. In some cases, the compound, salt, or pharmaceutical composition is administered in multiple doses.

In certain embodiments, the present disclosure provides a method for treating or preventing chemotherapy-induced cognitive impairment, comprising administering a compound, salt, or a pharmaceutical composition described herein to a patient undergoing or about to undergo cancer chemotherapy treatment. In some cases, the method comprises administering the compound, salt, or pharmaceutical composition prior to the cancer chemotherapy treatment. In some cases, the method comprises administering the compound, salt, or pharmaceutical composition from about one minute to about 7 days prior to the cancer chemotherapy treatment. In some cases, the method comprises administering the compound, salt, or a pharmaceutical composition simultaneously with the cancer chemotherapy treatment. In some cases, the method comprises administering the compound, salt, or pharmaceutical composition only on days when the cancer chemotherapy treatment is administered. In some embodiments, the method comprises administering the compound, salt, or pharmaceutical composition on days when the cancer chemotherapy treatment is administered and on one or more of those days intervening between successive doses of the chemotherapeutic. In some cases, the method comprises administering the compound, salt, or pharmaceutical composition after the cancer chemotherapy treatment. In some cases, the method comprises administering the compound, salt, or pharmaceutical composition from about one minute to about 7 days after the cancer chemotherapy treatment. In some cases, the cancer chemotherapy treatment is selected from the group consisting of taxane agents, platinum-complex agents, *vinca* alkaloids, proteasome inhibitors, 5-fluorouracil, methotrexate, doxorubicin, and combinations thereof.

In certain embodiments, the present disclosure provides a method for treating pain and discomfort of Irritable Bowel Syndrome comprising administering a compound, salt, or a pharmaceutical composition described herein to a patient undergoing or about to undergo cancer chemotherapy treatment. In some cases, the method comprises administering before the onset of pain or discomfort. In some cases, the method comprises administering after the onset of pain or discomfort. In some cases, the method comprises administering during the onset of pain or discomfort. In some cases, the pain or discomfort is reduced by at least about 10% as determined by an abdominal measurement to colorectal distension measurement. In some cases, the pain or discomfort is reduced by at least about 50%. In some cases, the pain or discomfort is reduced by at least about 90%. In some cases, the pain or discomfort is reduced by at least about 10% as determined by viscero-motor to colorectal distension measurement. In some cases, the pain or discomfort is reduced by at least 50%. In some cases, the pain or discomfort is reduced by at least 90%. In some cases, administering is performed at least 5 days after the onset of pain or discomfort.

In certain embodiments, a compound or salt of the disclosure administered with an analgesic may be used to alleviate the symptoms of neuropathic pain regardless of the cause of the pain, for example, but not limited to, spinal cord injury, multiple sclerosis, stroke, diabetes, herpes zoster infection, HIV-related neuropathies, nutritional deficiencies, toxins, remote manifestations of malignancies, genetic, immune mediated disorders or physical trauma to a nerve trunk, cancer, chemotherapy, radiation injury or surgery (e.g., post-operative pain), vulvodynia, and burning mouth syndrome. In an embodiment, the neuropathic pain is associated with chronic use of opioids.

The analgesic administered in conjunction with the compound or of the invention may be selected in relation to the particular condition being treated. Currently known analgesics include, but are not limited to, opioids, morphinomimetics, antidepressants, antiepileptics, NMDA receptor antagonists, fatty acid amine hydrolyase inhibitors, anticonvulsives, non-steroidal anti-inflammatory drugs (NSAIDs), COX-2 inhibitors, NOS inhibitors, acetaminophen, and calcium channel subunit $\alpha 2\delta$ ligands.

Example opioids include any natural or synthetic opioid analgesic, such as morphine, fentanyl, codeine, thebaine, diacetylmorphine (heroin), dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levoalphacetylmethadol (LAAM), loperamide, diphenoxylate, pentazocine, phenazocine, buprenorphine, etorphine, butorphanol, nalbuphine, levorphanol, levomethorphan, dezocine, lefetamine, tilidine, tramadol, propoxyphene, and oxycodone. As intended herein, an opioid also encompasses any natural or synthetic narcotic antagonist such as nalmefene, naloxone or naltrexone as well as any natural or synthetic mixed opioid agonist/antagonist such as nalbuphine, butorphanol, buprenorphine and pentazocine.

Example non-steroidal anti-inflammatory drugs (NSAIDs) include aspirine, ibuprofen, acetaminophen, naproxen, fenoprofen, ketoprofen, flurbiprofen, oxaprozin, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, and licofelone. Example antidepressants include tricyclic antidepressants such as: amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, and quinupramine; amineptine, norepinephrine, iprindole, opipramol, tianeptine, trimipramine, carbamezapine, and flupirtine.

It is contemplated that a compound or salt of the invention may be especially suited to the treatment of pain when co-administered with an opioid, a tricyclic antidepressant, or an analgesic believed to bind the calcium channel subunit $\alpha_2\delta$, i.e. a calcium channel subunit $\alpha_2\delta$ ligand. Examples of such ligands include GABA analogs, such as gabapentin (2-[1-(aminomethyl)cyclohexyl]acetic acid) and pregabalin ((S)-3-(aminomethyl)-5-methylhexanoic acid).

In certain embodiments, the method comprises administering to a subject a first amount of a compound or salt described herein in combination with a second amount of a dopamine agonist, e.g. carbidopa or levodopa.

The relative amounts of the compounds or salts thereof may be selected to provide for synergistic pain relief. For example, a suitable ratio of a compound of the invention to gabapentin may be in the range of from about 0.1 part by weight of the compound to from about 3 to about 30 parts by weight of the gabapentin. A suitable ratio of a compound of the invention to morphine may be in the range of from about 0.1 part by weight of the compound to from about 1 to about 5 parts by weight of the morphine. While these ratios are calculated with respect to the free compounds (non-salt forms), it should be understood that the equivalent ratios can also readily be determined for pharmaceutically acceptable salts or prodrugs of the compounds by using a ratio of the molecular weights of the salts.

In certain embodiments, co-administration of the compound of the invention and analgesic is achieved by formulating the compounds together in a combination composition. The combination composition may comprise a first pharmaceutically acceptable composition containing a first amount of a compound of the invention, and a second pharmaceutically acceptable composition comprising a second amount of an analgesic, wherein the first and second amounts taken together comprise a pharmaceutically effective amount. The first amount, the second amount, or both may be less than effective amounts of each compound administered as monotherapies. The combination composition is a pharmaceutically acceptable composition comprising a first amount of a compound or salt of the invention and a second amount of an analgesic, wherein the first and second amounts taken together comprise a pharmaceutically effective amount. The first amount, the second amount, or both may be less than effective amounts of each compound administered as monotherapies.

In an embodiment, the invention provides a method of reducing opioid antinociceptive tolerance and/or hypersensitivity in a subject receiving opioid therapy comprising administering to the subject an amount of a compound or salt of the invention sufficient to reduce opioid antinociceptive tolerance.

In another embodiment, there is provided a method of preventing or treating opioid dependence, i.e., withdrawal in a subject receiving opiates, comprising administering to the subject an amount of a compound or salt of the invention sufficient to treat one or more symptons of opioid withdrawal. The opioid may be morphine, oxycodone, fentanyl, cocaine herion, or opium. The compound or salt of the invention may be delivered prior to initiating withdrawal or after initiating withdrawal. The compound or salt of the invention may be co-administered with a decreasing dosage of opioid. The compound or salt of the invention may be delivered prior to beginning opioid therapy. The compound or salt of the invention may be delivered for a period of time after the opioid is no longer administered to the subject. The compound or salt of the invention may be delivered over a period of one week, two weeks, three weeks, four weeks, one month, two months, three months, four months, five months, or six months after the opiate is no longer administered to the subject. The opioid and/or the compound or salt of the invention may be delivered by continuous infusion, such as by an implanted pump.

The one or more symptoms of opioid withdrawal may comprise agitation, anxiety, muscle ache, increased tearing, insomnia, runny nose, sweating, and yawning, while late symptoms of withdrawal include abdominal cramping, diarrhea, dilated pupils, goose bumps, nausea and/or vomiting. The method may further comprise subjecting the subject to a drug treatment program, such as methadone treatment or buprenorphine treatment.

In other embodiments, the compound or salt of the invention is administered in conjunction with agents such as TNF-α inhibitors, IL-1β inhibitors, p38 kinase inhibitors, ERK inhibitors, JNK inhibitors, modulators of transcription factors such as NF-κB, agents that modulate glial cell function, agents that block expression and/or activity of adenosine kinase, recombinant ectonucleotidases, ENT inhibitors, and the like. Non-limiting examples of p38 kinase inhibitors include PH-797804, BIRB 796, VX-702, SB 239063, SB202190, SCIO 469, and BMS 582949. An example of an ERK inhibitor is sorafenib. An example of a JNK inhibitor is AM-111. Non-limiting examples of NF-κB modulators include disulfiram, olmesartan, dithiocarbamates, and anatabine.

The following examples further illustrate the invention but, of course, should not be construed as in any way limiting its scope.

EXAMPLES

The invention now being generally described will be more readily understood by reference to the following examples which are included merely for purposes of illustration of certain aspects and embodiments of the present invention, and are not intended to limit the invention in any way.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Examples 1-11 show exemplary procedures for the preparation of key intermediates and the claimed $A_3$ receptor agonists.

Example 1. Preparation of 2,6-dichloro-9-((3aR,3bR,4aS,5R,5aS)-2,2-dimethylhexahydrocyclopropa[3,4]cyclopenta[1,2-d][1,3]dioxol-5-yl)-9H-purine (5.1)

5.1

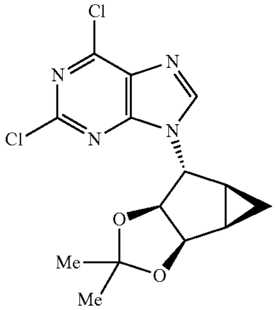

Step-1

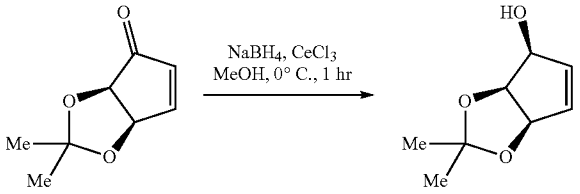

1

2

To a solution of compound 1 (4.50 g) in MeOH (225 mL) was added $CeCl_3$ (7.19 g. 1.84 mL, 1.00 eg), then $NaBH_4$ (1.27 g, 1.15 eq) was added portion-wise at 0° C. The mixture was stirred at 0° C. for 1 hr. TLC (petroleum ether:ethyl acetate=5:1) showed that the starting material was consumed and a new spot was formed. The mixture was quenched with water (100 mL) and was extracted with DCM (50 mL×3), and then the combined organic extract was washed with brine.

After drying over $Na_2SO_4$ and filtration, the solvent was concentrated in vacuum. The mixture was purified by column chromatography ($SiO_2$, petroleum ether:eEthyl acetate=50:1 to 5:1) to give compound 2 (3.20 g) as yellow liquid. $^1H$ NMR: 400 MHz $CDCl_3$ δ (ppm) 5.96-5.86 (m, 2H), 5.02 (d, J=5.5 Hz, 1H), 4.75 (t, J=5.6 Hz, 1H), 4.56 (dd, J=5.6, 9.8 Hz, 1H), 2.71 (d, J=9.9 Hz, 1H), 1.44 (s, 3H), 1.41 (s, 3H).

Step-2

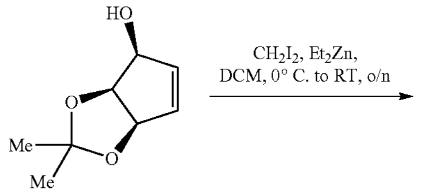

2

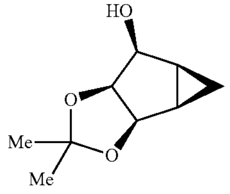

3

A solution of diethylzinc in DCM (1.0 M, 89.6 mL, 4.00 eq) was added dropwise to a solution of compound 2 (3.50 g, 1.00 eq) in DCM (110 mL) at 0° C. After stirring the mixture at 0° C. for 15 min, $CH_2I_2$ (48.0 g, 14.4 mL, 8.00 eq) was added and the mixture was stirred at 20° C. for 16 hrs. TLC (petroleum ether:ethyl acetate=2:1) showed the starting material was consumed. The mixture was quenched by saturated $NH_4Cl$ solution (100 mL) and was extracted with DCM (50 mL×3). The organic extract was dried over $Na_2SO_4$ and was concentrated to give the crude product, which was purified by column chromatography ($SiO_2$, petroleum ether:ethyl acetate=20:1 to 5:1) to give compound 3 (1.90 g) as colorless oil. $^1H$ NMR: 400 MHz $CDCl_3$ δ (ppm) 4.89 (t, J=5.9 Hz, 1H), 4.59-4.43 (m, 2H), 2.35 (s, 1H), 1.91-1.80 (m, 1H), 1.71-1.60 (m, 1H), 1.56 (s, 3H), 1.30 (s, 3H), 1.05-0.88 (m, 1H), 0.69-0.58 (m, 1H).

Step-3

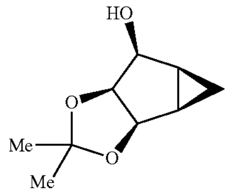

3

+

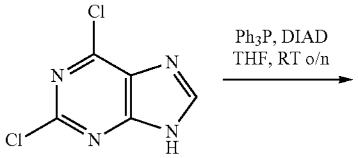

4

-continued

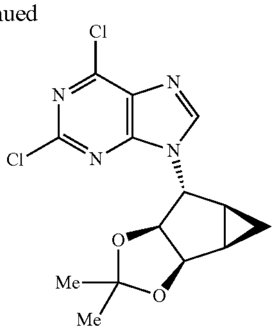

5.1

To a solution of compound 4 (3.16 g, 1.50 eq) in THF (40 mL) under $N_2$ was added $PPh_3$ (5.86 g, 2.00 eq) and DIAD (4.51 g, 4.34 mL, 2.00 eq). After stirring the mixture at 20° C. for 15 min, compound 3 (1.90 g, 1.00 eq) was added and the mixture was stirred at 20° C. for 16 hrs. TLC (petroleum ether:thyl acetate=1:1) showed the starting material was consumed. The reaction mixture was concentrated under reduced pressure to give a residue. The residue was purified by column chromatography ($SiO_2$, petroleum ether:ethyl acetate=20:1 to 5:1) to give compound 5.1 (3.50 g) as white solid. MS: 340.9 (M+H)+. $^1H$ NMR: 400 MHz $CDCl_3$ δ (ppm) 8.16 (s, 1H), 5.43-5.32 (m, 11H), 5.05 (s, 11H), 4.67 (d, J=7.2 Hz, 1H), 2.21-2.11 (m, 1H), 1.72-1.63 (m, 1H), 1.55 (s, 3H), 1.26 (s, 3H), 1.01-0.99 (s, 2H).

Similarly prepared according to the method of Example 1 were the following intermediates:

Substituting 6-chloro-2-iodo-9H-purine for 4 in step-3 gave 6-chloro-9-((3aR,3bR,4aS,5R,5aS)-2,2-dimethylhexahydrocyclopropa[3,4]cyclopenta[1,2-d][1,3]dioxol-5-yl)-2-iodo-9H-purine (5.2). MS: 433.0 $(M+H)^+$. $^1H$ NMR: 400 MHz DMSO-$d_6$ δ (ppm) 8.71 (s, 1H), 5.31-5.24 (m, 1H), 5.01 (s, 1H), 4.73 (d, J=7.2 Hz, 1H), 2.02-1.96 (m, 1H), 1.83-1.76 (m, 1H), 1.44 (s, 3H), 1.17-1.13 (m, 3H), 0.90-0.76 (m, 2H);

Substituting 5,7-dichloro-3H-imidazo[4,5-b]pyridine for 4 in step-3 gave 5,7-dichloro-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridine (5.3). MS: 339.9 (M+H)+. $^1H$ NMR: 400 MHz DMSO-$d_6$ δ (ppm) 8.69 (s, 1H), 7.66 (s, 1H), 5.28 (t, J=6.0 Hz, 1H), 5.03 (s, 1H), 4.69 (d, J=6.8 Hz, 1H), 2.01-2.99 (m, 1H), 1.81-1.78 (m, 1H), 1.44 (s, 3H), 1.16 (s, 3H), 0.88-0.79 (m, 2H);

Substituting 7-chloro-3H-imidazo[4,5-b]pyridine for 4 in step-3 gave 7-chloro-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridine (5.4). MS: 306.1 $(M+H)^+$. $^1H$ NMR: 400 MHz DMSO-$d_6$ δ (ppm) 8.66 (s, 1H), 8.36 (d, J=5.2 Hz, 1H), 7.47 (d, J=5.0 Hz, 1H), 5.34-5.26 (m, 1H), 5.10 (s, 1H), 4.69 (d, J=7.2 Hz, 1H), 2.04-1.98 (m, 1H), 1.83-1.76 (m, 1H), 1.44 (s, 3H), 1.14-1.12 (m, 3H), 0.90-0.78 (m, 2H);

Substituting 5-bromo-7-chloro(bromo)-3H-imidazo[4,5-b]pyridine for 4 in step-3 gave 5-bromo-7-chloro(bromo)-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridine (5.5). MS: 386.0 (M+H)+ and 430.0 (M+H)+. 7-chloro isomer, $^1H$ NMR: 400 MHz DMSO-$d_6$ 3 (ppm) 8.74 (s, 1H), 7.82 (s, 1H), 5.34 (t, J=6.0 Hz, 1H), 5.09 (d, J=5.2 Hz, 1H), 4.76 (d, J=6.8 Hz, 1H), 2.07-2.04 (m, 1H), 1.86-1.84

(m, 1H), 1.51 (s, 3H), 1.23 (s, 3H), 0.94-0.85 (m, 2H). 7-bromo isomer δ (ppm) 8.74 (s, 1H), 7.93 (s, 1H), 5.34 (t, J=6.0 Hz, 1H), 5.09 (d, J=5.2 Hz, 1H), 4.76 (d, J=6.8 Hz, 1H), 2.07-2.04 (m, 1H), 1.86-1.84 (m, 1H), 1.51 (s, 3H), 1.23 (s, 3H), 0.94-0.85 (m, 2H).

TABLE 1

| Intermediates prepared by the method of Example 1 | |
|---|---|
| 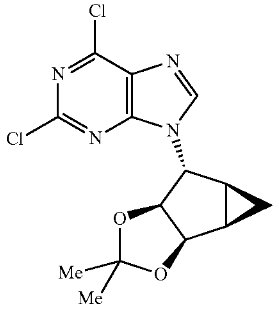 [SMILES: CC1(C)O[C@@H]2[C@@H]3C[C@@H]3[C@@H](n3cnc4c(Cl)nc(Cl)nc43)[C@@H]2O1] | 5.1 |
| 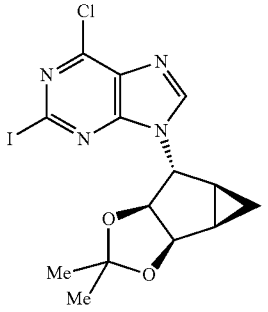 [SMILES: CC1(C)O[C@@H]2[C@@H]3C[C@@H]3[C@@H](n3cnc4c(Cl)nc(I)nc43)[C@@H]2O1] | 5.2 |
| 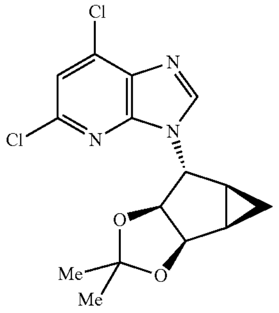 [SMILES: CC1(C)O[C@@H]2[C@@H]3C[C@@H]3[C@@H](n3cnc4c(Cl)cc(Cl)nc43)[C@@H]2O1] | 5.3 |
| 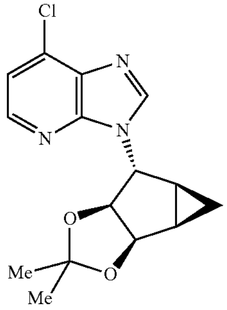 [SMILES: CC1(C)O[C@@H]2[C@@H]3C[C@@H]3[C@@H](n3cnc4c(Cl)ccnc43)[C@@H]2O1] | 5.4 |

TABLE 1-continued

| Intermediates prepared by the method of Example 1 | |
|---|---|
| 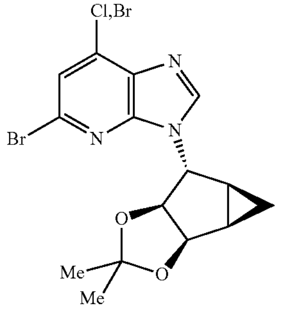 | 5.5 |

Example 2. Preparation of 2-chloro-N-(2,2-difluoroethyl)-9-((3aR,3bR,4aS,5R,5aS)-2,2-dimethylhexahydrocyclopropa[3,4]cyclopenta[1,2-d][1,3]dioxol-5-yl)-9H-purin-6-amine (7.1)

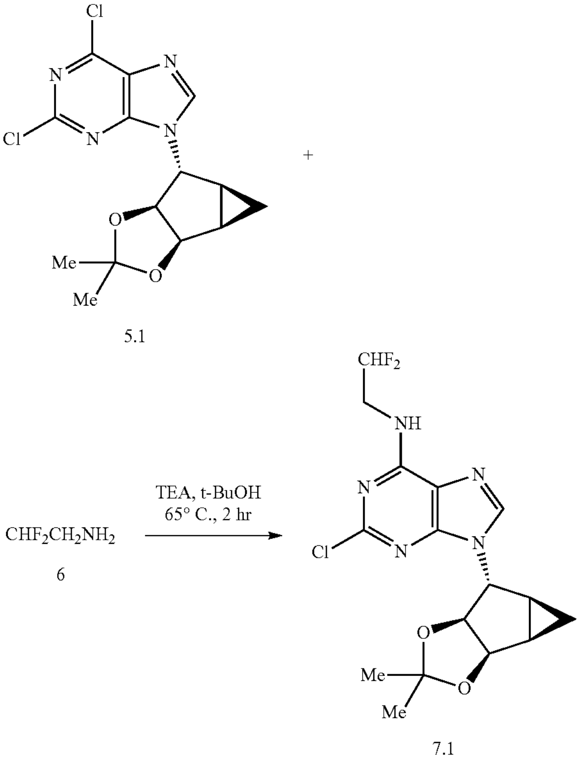

A solution of compound 5.1 (150.0 mg, 1.00 eq), compound 6 (71.2 mg, 2.00 eq), TEA (222.4 mg, 305.9 μL, 5.00 eq) in t-BuOH (2 mL) was stirred at 65° C. for 2 hrs. LCMS analysis showed the starting material was consumed completely. The reaction mixture was concentrated under reduced pressure to give a residue. The residue was purified by prep-TLC ($SiO_2$, EtOAc) to give compound 7.1 (110.0 mg) as yellow solid. MS: 386.0 (M+H)+. $^1H$ NMR: 400 MHz DMSO-$d_6$ δ (ppm) 8.63 (s, 1H), 8.31 (s, 1H), 6.35-6.01 (m, 1H), 5.25 (t, J=6.0 Hz, 1H), 4.89 (s, 1H), 4.63 (d, J=7.2 Hz, 1H), 3.95-3.75 (m, 2H), 1.99-1.93 (m, 1H), 1.78-1.69 (m, 1H), 1.44 (s, 3H), 1.18-1.14 (m, 3H), 0.89-0.74 (m, 2H).

Similarly prepared by the method of Example 2 were the following intermediates:

Substituting 2-fluoroethylamine for 6 gave 2-chloro-9-((3aR,3bR,4aS,5R,5aS)-2,2-dimethylhexahydrocyclopropa[3,4]cyclopenta[1,2-d][1,3]dioxol-5-yl)-N-(2-fluoroethyl)-9H-purin-6-amine (7.2). MS: 368.2 $(M+H)^+$. $^1H$ NMR: 400 MHz DMSO-$d_6$ δ (ppm) 8.48-8.42 (m, 1H), 8.27 (s, 1H), 5.25 (t, J=5.8 Hz, 1H), 4.80-4.71 (m, 1H), 4.68-4.60 (m, 2H), 4.54 (t, J=4.8 Hz, 1H), 3.81-3.67 (m, 2H), 1.98-1.96 (m, 1H), 1.76-1.69 (m, 1H), 1.44 (s, 3H), 1.19 (s, 3H), 0.89-0.74 (m, 2H);

Substituting 2,2,2-trifluoroethylamine for 6 gave 2-chloro-9-((3aR,3bR,4aS,5R,5aS)-2,2-dimethylhexahydrocyclopropa[3,4]cyclopenta[1,2-d][1,3]dioxol-5-yl)-N-(2,2,2-trifluoroethyl)-9H-purin-6-amine (7.3). MS: 404.1 $(M+H)^+$. $^1H$ NMR: 400 MHz DMSO-$d_6$ δ (ppm) 8.92 (s, 1H), 8.35 (s, 11H), 5.25 (t, J=6.4 Hz, 1H), 4.90 (s, 1H), 4.65 (d, J=7.2 Hz, 1H), 4.26 (s, 2H), 1.98-1.96 (m, 1H), 1.76-1.74 (m, 1H), 1.43 (s, 3H), 1.11 (s, 3H), 0.85-0.77 (m, 21H).

Substituting methyl-d3 amine for 6 gave 2-chloro-9-((3aR,3bR,4aS,5R,5aS)-2,2-dimethylhexahydrocyclopropa[3,4]cyclopenta[1,2-d][1,3]dioxol-5-yl)-N-methyl-$d_3$-9H-purin-6-amine (7.4). MS 339 $(M+H)^+$.

TABLE 2

Intermediates prepared by the method of Example 2.

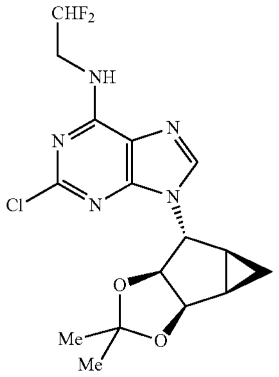

7.1

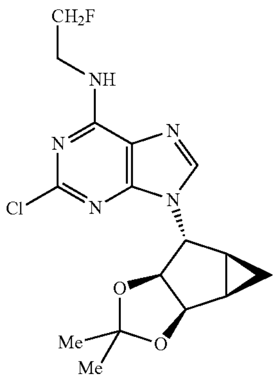

7.2

TABLE 2-continued

Intermediates prepared by the method of Example 2.

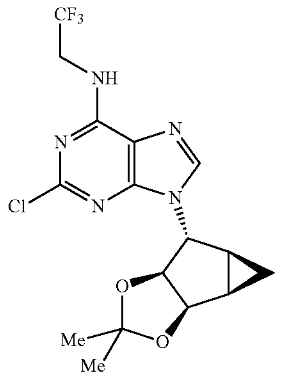

7.3

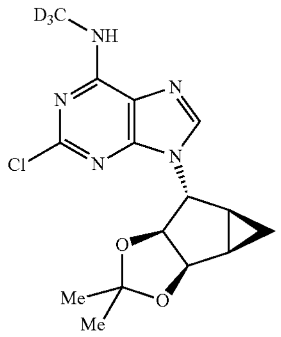 [SMILES: [2H]C([2H])([2H])Nc1nc(Cl)nc2c1ncn2[C@@H]1[C@H]2C[C@H]2[C@H]2OC(C)(C)O[C@H]21]

7.4

Example 3. Preparation of N-(2,2-difluoroethyl)-9-((3aR,3bR,4aS,5R,5aS)-2,2-dimethylhexahydrocyclopropa[3,4]cyclopenta[1,2-d][1,3]dioxol-5-yl)-2-iodo-9H-purin-6-amine (8.1)

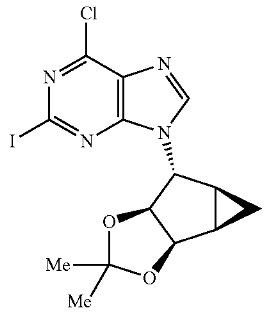

5.2

+

-continued

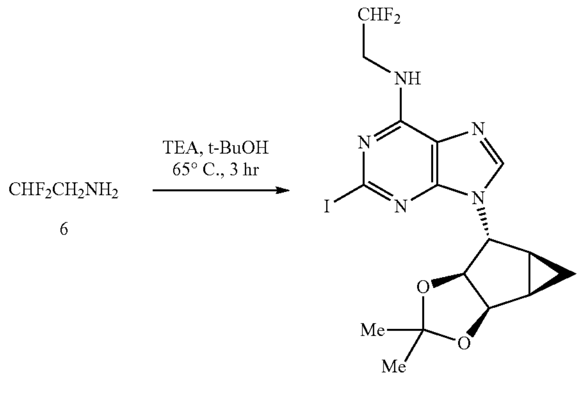

6

8.1

A solution of compound 5.2 (300.0 mg, 1.00 eq), compound 6 (84.3 mg, 1.50 eq) in t-BuOH (5 mL) was added TEA (350.8 mg, 482.6 μL, 5.00 eq) at 20° C. The mixture was stirred at 65° C. for 3 hrs. TLC analysis (EtOAc) showed the starting material was consumed completely. The mixture was diluted with $H_2O$ (20 mL) and was extracted with EtOAc (20 mL×4). The organic extract was dried over $Na_2SO_4$, was filtrated and was concentrated. The residue, was purified by prep-TLC (EtOAc) to give compound 8.1 (250.0 mg) as a yellow solid. $^1H$ NMR: 400 MHz DMSO-$d_6$ δ (ppm) 8.46 (s, 1H), 8.22 (s, 1H), 6.33-6.01 (m, 1H), 5.22-5.29 (m, 1H), 4.88 (s, 1H), 4.62 (d, J=6.8 Hz, 1H), 3.91-3.72 (m, 2H), 1.98-1.93 (m, 1H), 1.65-1.74 (m, 1H), 1.44 (s, 3H), 1.17 (s, 3H), 0.74-0.88 (m, 2H).

Similarly prepared by the method of Example 3 was:

Substituting ethyl amine for 6 gave 9-((3aR,3bR,4aS,5R,5aS)-2,2-dimethylhexahydrocyclopropa[3,4]cyclopenta[1,2-d][1,3]dioxol-5-yl)-N-ethyl-2-iodo-9H-purin-6-amine (8.2). MS: 442.0 $(M+H)^+$. $^1H$ NMR: 400 MHz $CDCl_3$ δ (ppm) 7.65 (s, 1H), 5.68 (s, 1H), 5.36-5.33 (m, 1H), 4.94 (s, 1H), 4.64 (d, J=7.2 Hz, 1H), 3.65 (s, 2H), 2.10-2.08 (m, 1H), 1.65-1.60 (m, 1H), 1.54 (s, 3H), 1.31-1.25 (m, 6H), 0.97-0.89 (m, 2H).

TABLE 3

| Intermediates prepared by the method of Example 3 | |
|---|---|
| 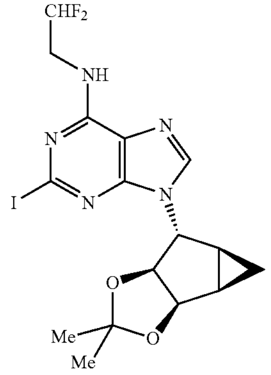 [SMILES: CC1(C)O[C@@H]2[C@@H]3C[C@@H]3[C@@H](n3cnc4c(NCC(F)F)nc(I)nc43)[C@@H]2O1] | 8.1 |

TABLE 3-continued

| Intermediates prepared by the method of Example 3 | |
|---|---|
| 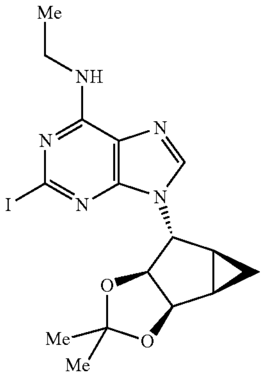 [SMILES: CCNc1nc(I)nc2c1ncn2[C@@H]1[C@H]2C[C@H]2[C@H]2OC(C)(C)O[C@H]21] | 8.2 |

Example 4. Preparation of 5-chloro-N-(2,2-difluoroethyl)-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridin-7-amine (9.1)

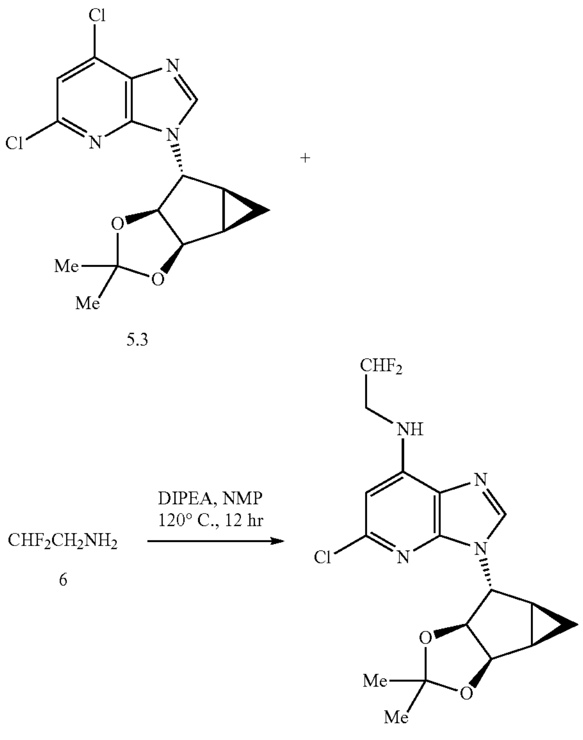

5.3

6

9.1

To a solution of compound 5.3 (300.0 mg, 1.0 eq) in NMP (3 mL) was added DIPEA (569.8 mg, 768.0 μL, 5.0 eq) and compound 6 (285.9 mg, 130.5 μL, 4.0 eq). The mixture was stirred at 120° C. for 16 hrs. TLC analysis (ethyl acetate) showed compound 5.3/compound 9.1=2/1. The mixture was extracted with ethyl acetate (10 mL×3). The combined organic layers were washed with brine (20 mL×3), dried over $Na_2SO_4$, filtered and concentrated under reduced pressure to give a residue. The residue was purified by Pre-TLC (DCM/MeOH=40/1) to obtain compound 9.1 (130.0 mg) as a yellow solid. MS: 385.1 $(M+H)^+$. $^1$H NMR: 400 MHz DMSO-$d_6$ δ (ppm) 8.26 (s, 1H), 7.47 (t, J=6.8 Hz, 1H), 6.57 (s, 1H), 6.32-6.03 (m, 1H), 5.09 (t, J=6.4 Hz, 1H), 4.92 (s, 1H), 4.58 (d, J=6.8 Hz, 1H), 3.97 (brs, 2H), 1.98-1.95 (m, 1H), 1.72-1.70 (m, 1H), 1.44 (s, 3H), 1.16 (s, 3H), 0.84-0.79 (m, 2H).

Similarly prepared by the method of Example 4 were the following compounds:

Substituting 2-fluoroethylamine for 6 gave 5-chloro-3-((3aR,3bR,4aS,5R,5aS)-2,2-dimethylhexahydrocyclopropa[3,4]cyclopenta[1,2-d][1,3]dioxol-5-yl)-N-(2-fluoroethyl)-3H-imidazo[4,5-b]pyridin-7-amine (9.2). MS: 366.9 $(M+H)^+$. $^1$H NMR: 400 MHz DMSO-$d_6$ δ (ppm) 8.21 (s, 1H), 7.37-7.34 (m, 1H), 6.47 (s, 1H), 5.30-5.25 (m, 1H), 4.91 (s, 1H), 4.59-4.52 (m, 3H), 3.81-3.73 (m, 2H), 2.00-1.95 (m, 1H), 1.73-1.68 (m, 1H), 1.44 (s, 3H), 1.19-1.16 (m, 4H), 0.80-0.78 (m, 1H);

Substituting 2,2,2-trifluoroethylamine for 6 gave 5-chloro-3-((3aR,3bR,4aS,5R,5aS)-2,2-dimethylhexahydrocyclopropa[3,4]cyclopenta[1,2-d][1,3]dioxol-5-yl)-N-(2,2,2-trifluoroethyl)-3H-imidazo[4,5-b]pyridin-7-amine (9.3). MS: 403.2 $(M+H)^+$. $^1$H NMR: 400 MHz DMSO-$d_6$ δ (ppm) 8.28 (s, 1H), 7.71 (t, J=6.8 Hz, 1H), 6.66 (s, 1H), 5.28-5.25 (m, 1H), 4.93 (s, 1H), 4.59 (d, J=7.2 Hz, 1H), 4.47 (s, 2H), 1.98-1.97 (m, 1H), 1.73-1.718 (m, 1H), 1.44 (s, 3H), 1.62 (s, 3H), 0.85-0.78 (m, 2H);

Substituting ethylamine for 6 gave 5-chloro-3-((3aR,3bR,4aS,5R,5aS)-2,2-dimethylhexahydrocyclopropa[3,4]cyclopenta[1,2-d][1,3]dioxol-5-yl)-N-ethyl-3H-imidazo[4,5-b]pyridin-7-amine (9.4). MS: 349.0 $(M+H)^+$. $^1$H NMR: 400 MHz DMSO-$d_6$ δ (ppm) 8.18 (s, 11H), 7.19 (t, J=5.6 Hz, 11H), 6.35 (s, 11H), 5.27 (t, J=6.0 Hz, 11H), 4.91 (s, 1H), 4.59 (d, J=6.8 Hz, 1H), 3.41 (brs, 2H), 1.99-1.97 (m, 1H), 1.72-1.69 (m, 1H), 1.44 (s, 3H), 1.20-1.17 (m, 6H), 0.84-0.79 (m, 2H);

Substituting cyclobutylamine for 6 gave 5-chloro-N-cyclobutyl-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridin-7-amine (9.5). MS: 375.2 $(M+H)^+$. $^1$H NMR: 400 MHz DMSO-$d_6$ δ (ppm) 8.19 (s, 1H), 7.44 (d, J=7.2 Hz, 1H), 6.29 (s, 1H), 5.30-5.23 (m, 1H), 4.90 (s, 1H), 4.57 (d, J=7.2 Hz, 1H), 4.47-4.15 (m, 1H), 2.37-2.27 (m, 2H), 2.09-1.93 (m, 3H), 1.75-1.64 (m, 3H), 1.43 (s, 3H), 1.16 (s, 3H), 0.87-0.75 (m, 2H);

Substituting 2,5-difluorobenzylamine for 6 gave 5-chloro-N-(2,5-difluorobenzyl)-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridin-7-amine (9.6) MS: 447.3 $(M+H)^+$. $^1$H NMR: 400 MHz DMSO-$d_6$ δ (ppm) 8.24 (s, 1H), 7.82-7.79 (m, 1H), 7.28-7.26 (m, 1H), 7.17-7.12 (m, 2H), 6.38 (s, 1H), 5.27-5.24 (m, 1H), 4.91 (s, 1H), 4.71-4.69 (m, 2H), 4.60-4.58 (m, 1H), 1.99-1.96 (m, 1H), 1.72-1.71 (m, 1H), 1.43 (s, 3H), 1.16 (s, 3H), 0.86-0.78 (m, 2H).

Substituting (5-chloro-2-((3-methylisoxazol-5-yl)methoxy)phenyl)methanamine for 6 gave 5-chloro-N-(5-chloro-2-((3-methylisoxazol-5-yl)methoxy)benzyl)-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridin-7-amine (9.7). LCMS: MS: 556.1 $(M+H)^+$.

Substituting (6-methoxypyridin-2-yl)methanamine for 6 gave 5-chloro-3-((3aR,3bR,4aS,5R,5aS)-2,2-dimethylhexahydrocyclopropa[3,4]cyclopenta[1,2-d][1,3]dioxol-5-yl)-N-((6-methoxypyridin-2-yl)methyl)-3H-imidazo[4,5-b]pyridin-7-amine (9.8). LCMS: 442.1 $(M+H)^+$.

Substituting propan-1-amine for 6 gave 5-chloro-3-((3aR,3bR,4aS,5R,5aS)-2,2-dimethylhexahydrocyclopropa[3,4]cyclopenta[1,2-d][1,3]dioxol-5-yl)-N-propyl-3H-imidazo[4,5-b]pyridin-7-amine (9.9). LCMS: 363.1 (M+H)+.

Substituting cyclobutylmethanamine for 6 gave 5-chloro-N-(cyclobutylmethyl)-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridin-7-amine. (9.10) LCMS: 389.1 $(M+H)^+$.

Substituting (2,5-dichlorophenyl)methanamine for 6 gave 5-chloro-N-(2,5-dichlorobenzyl)-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridin-7-amine. (9.11) LCMS: Rt=0.798, MS: 479.1 $(M+H)^+$.

TABLE 4

Intermediates prepared by the method of Example 4

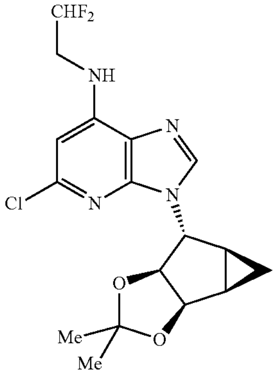 [SMILES: CC1(C)O[C@@H]2[C@@H]3C[C@@H]3[C@@H](n3cnc4c(NCC(F)F)cc(Cl)nc43)[C@@H]2O1]

9.1

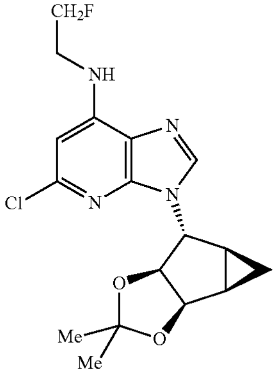

9.2

TABLE 4-continued
| Intermediates prepared by the method of Example 4 | |
|---|---|
| 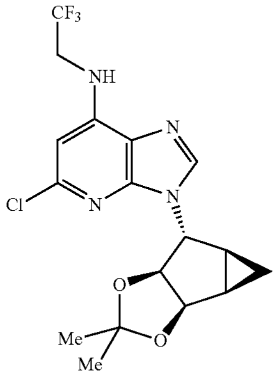 [SMILES: CC1(C)O[C@@H]2[C@@H]3C[C@@H]3[C@@H](n3cnc4c(NCC(F)(F)F)cc(Cl)nc43)[C@@H]2O1] | 9.3 |
| 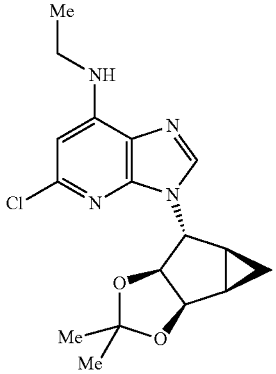 [SMILES: CCNc1cc(Cl)nc2c1ncn2[C@@H]1[C@H]2C[C@H]2[C@H]2OC(C)(C)O[C@H]21] | 9.4 |
| 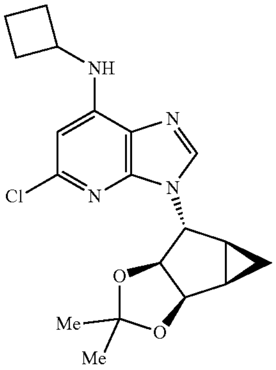 [SMILES: CC1(C)O[C@@H]2[C@@H]3C[C@@H]3[C@@H](n3cnc4c(NC5CCC5)cc(Cl)nc43)[C@@H]2O1] | 9.5 |
| 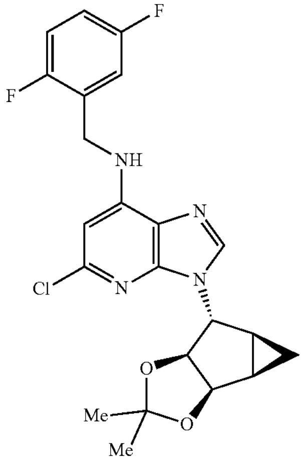 [SMILES: CC1(C)O[C@@H]2[C@@H]3C[C@@H]3[C@@H](n3cnc4c(NCc5cc(F)ccc5F)cc(Cl)nc43)[C@@H]2O1] | 9.6 |
TABLE 4-continued
| Intermediates prepared by the method of Example 4 | |
|---|---|
| 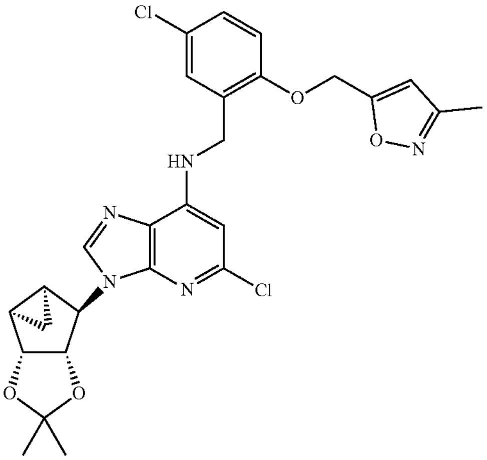 [SMILES: Cc1cc(COc2ccc(Cl)cc2CNc2cc(Cl)nc3c2ncn3[C@@H]2[C@H]3C[C@H]3[C@H]3OC(C)(C)O[C@H]32)on1] | 9.7 |
| 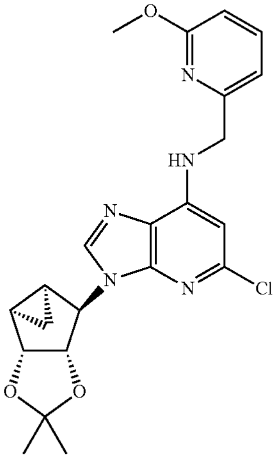 [SMILES: COc1cccc(CNc2cc(Cl)nc3c2ncn3[C@@H]2[C@H]3C[C@H]3[C@H]3OC(C)(C)O[C@H]32)n1] | 9.8 |
| 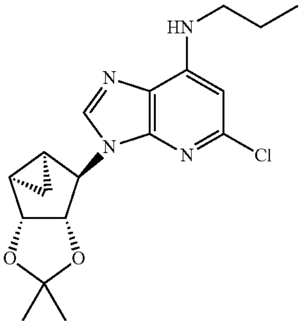 [SMILES: CCCNc1cc(Cl)nc2c1ncn2[C@@H]1[C@H]2C[C@H]2[C@H]2OC(C)(C)O[C@H]21] | 9.9 |
| 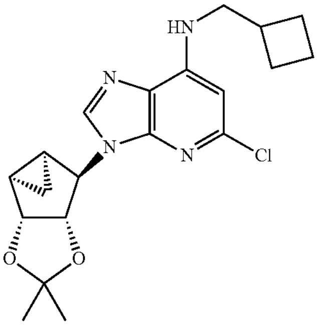 [SMILES: CC1(C)O[C@@H]2[C@@H]3C[C@@H]3[C@@H](n3cnc4c(NCC5CCC5)cc(Cl)nc43)[C@@H]2O1] | 9.10 |

TABLE 4-continued

| Intermediates prepared by the method of Example 4 | |
|---|---|
| 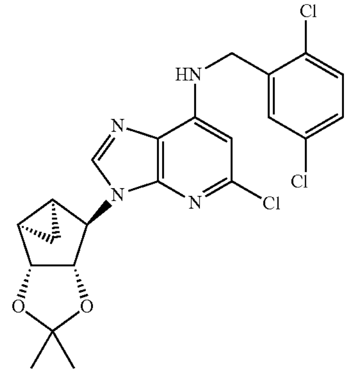 [SMILES: CC1(C)O[C@@H]2[C@@H]3C[C@@H]3[C@@H](n3cnc4c(NCc5cc(Cl)ccc5Cl)cc(Cl)nc43)[C@@H]2O1] | 9.11 |

Example 5. Preparation of 2-(cyclopropylethynyl)-N-(2,2-difluoroethyl)-9-((3aR,3bR,4aS,5R,5aS)-2,2-dimethylhexahydrocyclopropa[3,4]cyclopenta[1,2-d][1,3]dioxol-5-yl)-9H-purin-6-amine (11.1)

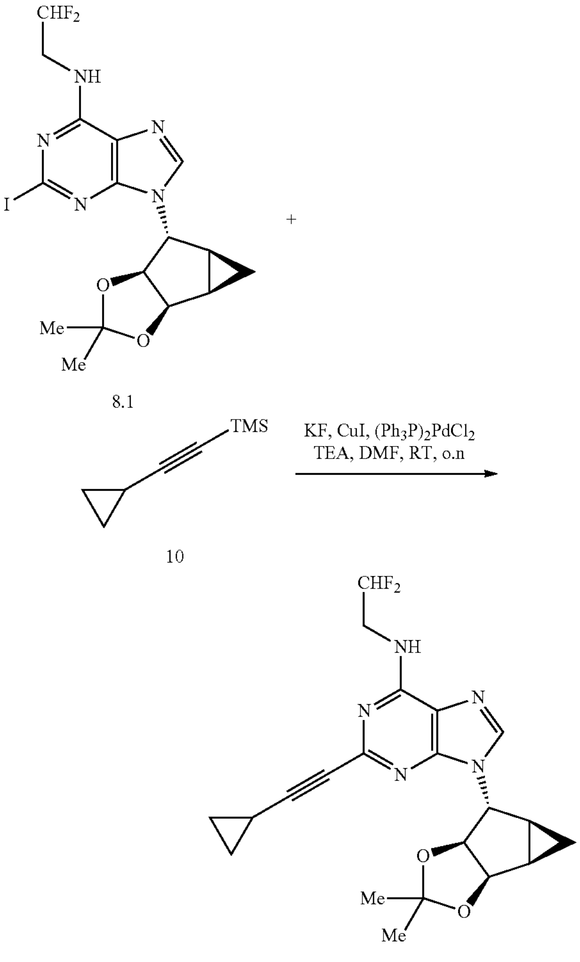

8.1

10

11.1

A solution of compound 8.1 (220.0 mg, 1.00 eq), compound 10 (382.5 mg, 312.8 μL, 6.00 eq) in DMF (5 mL) was added TEA (466.5 mg, 641.6 μL, 10.0 eq), CuI (17.6 mg, 0.20 eq), KF (80.4 mg, 3.00 eq) at 20° C. under $N_2$, then $Pd(PPh_3)_2Cl_2$ (64.7 mg, 0.20 eq) was added at 20° C. under $N_2$.

The mixture was stirred at 20° C. for 12 hrs. LCMS analysis showed the starting material was consumed completely. The mixture was diluted with $H_2O$ (20 mL) and was extracted with EtOAc (20 mL×4). The organic extract was dried over $Na_2SO_4$, was filtered and was concentrated to give a residue, which was purified by prep-TLC (EtOAc) to give compound 11.1 (160.0 mg) as red oil. MS 416.2 $(M+H)^+$. $^1H$ NMR: 400 MHz DMSO-$d_6$ δ (ppm) 8.32 (s, 1H), 8.25-8.10 (m, 1H), 6.35-6.05 (m, 1H), 5.24-5.22 (m, 1H), 4.91 (s, 1H), 4.57 (d, J=7.2 Hz, 1H), 3.98-3.76 (m, 2H), 1.77-1.69 (m, 1H), 1.63-1.54 (m, 1H), 1.44 (s, 3H), 1.16 (s, 3H), 0.95-0.89 (m, 2H), 0.86-0.73 (m, 5H).

Similarly prepared by the method of Example 5 was:

Substituting 8.2 for 8.1 gave 2-(cyclopropylethynyl)-9-((3aR,3bR,4aS,5R,5aS)-2,2-dimethylhexahydrocyclopropa[3,4]cyclopenta[1,2-d][1,3]dioxol-5-yl)-N-ethyl-9H-purin-6-amine (11.2). MS: 380.2 $(M+H)^+$ $^1H$ NMR: 400 MHz $CDCl_3$ δ (ppm) 7.77 (s, 1H), 5.32-5.30 (m, 1H), 5.11 (s, 1H), 4.58 (d, J=7.2 Hz, 1H), 3.74 (s, 2H), 2.10-2.07 (m, 1H), 1.69-1.65 (m, 1H), 1.54-1.48 (m, 4H), 1.31 (t, J=7.2 Hz, 3H), 1.24 (s, 3H), 0.97-0.90 (m, 6H);

Substituting 26.3 for 8.1 gave 5-(cyclopropylethynyl)-3-((3aR,3bS,4aS,5R,5aS)-3b-(difluoromethyl)-2,2-dimethylhexahydrocyclopropa[3,4]cyclopenta[1,2-d][1,3]dioxol-5-yl)-N-ethyl-3H-imidazo[4,5-b]pyridin-7-amine (11.3). MS: 429.3 $(M+H)^+$. $^1H$ NMR: 400 MHz DMSO-$d_6$ δ (ppm) 8.06 (s, 1H), 6.90 (s, 1H), 6.54-6.22 (m, 2H), 5.35 (d, J=7.2 Hz, 1H), 5.01 (s, 1H), 4.67 (d, J=6.8 Hz, 1H), 3.43-3.35 (m, 2H), 1.99 (s, 3H), 1.96-1.90 (m, 1H), 1.61-1.51 (m, 1H), 1.46 (s, 3H), 1.32-1.26 (m, 1H), 1.20-1.18 (m, 4H), 0.96-0.88 (m, 2H), 0.79-0.69 (m, 2H).

TABLE 5

| Intermediates prepared by the method of Example 5 | |
|---|---|
| 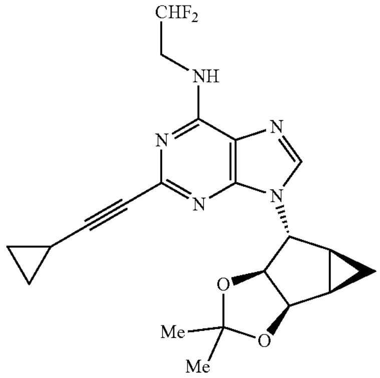 [SMILES: CC1(C)O[C@@H]2[C@@H]3C[C@@H]3[C@@H](n3cnc4c(NCC(F)F)nc(C#CC5CC5)nc43)[C@@H]2O1] | 11.1 |

TABLE 5-continued

| Intermediates prepared by the method of Example 5 | |
|---|---|
| 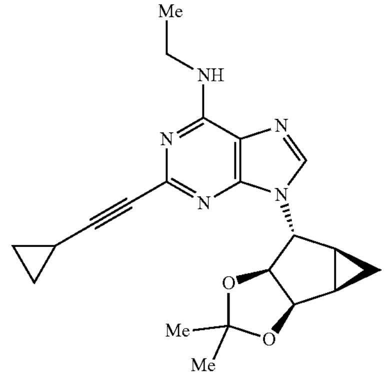 [SMILES: CCNc1nc(C#CC2CC2)nc2c1ncn2[C@@H]1[C@H]2C[C@H]2[C@H]2OC(C)(C)O[C@H]21] | 11.2 |
| 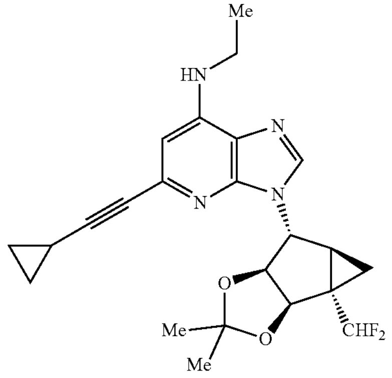 [SMILES: CCNc1cc(C#CC2CC2)nc2c1ncn2[C@H]1[C@@H]2OC(C)(C)O[C@@H]2[C@]2(C(F)F)C[C@H]12] | 11.3 |

Example 6. Preparation of 5-(cyclopropylethynyl)-3-((3aR,3bR,4aS,5R,5aS)-2,2-dimethylhexahydrocyclopropa[3,4]cyclopenta[1,2-d][1,3]dioxol-5-yl)-N-ethyl-3H-imidazo[4,5-b]pyridin-7-amine (14.1)

14.1

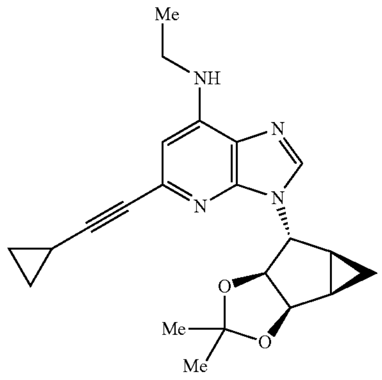

Step-1

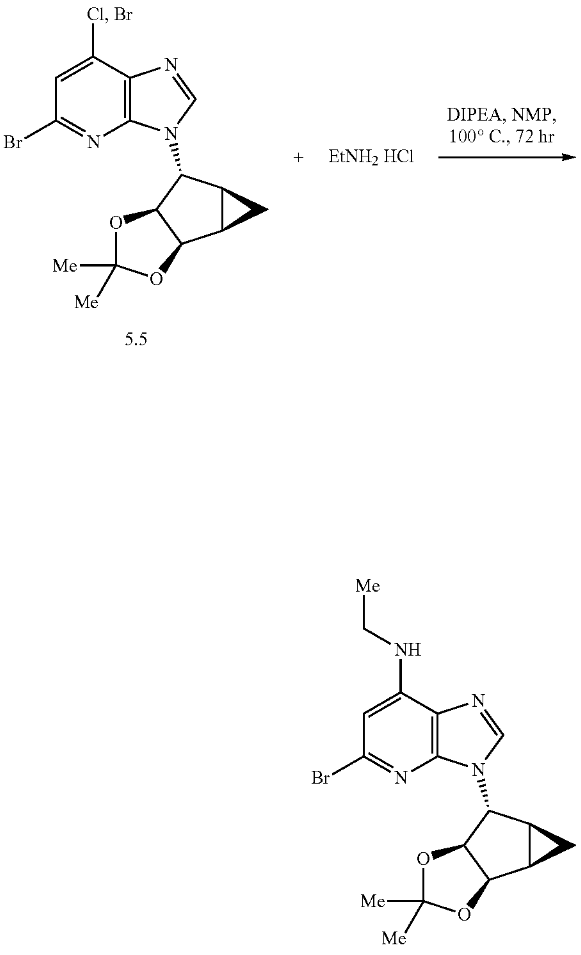

5.5

12

To a solution of compound 5.5 (140.0 mg, crude) in NMP (5 mL) was added DIPEA (1.11 g, 1.50 mL, 23.6 eq) and ethylamine hydrochloride (148.4 mg, 5.00 eq) at 20° C. The mixture was stirred at 100° C. for 12 hrs. TLC analysis (dichloromethane:methanol=10:1) indicated compound 5.5 was consumed, and one major new spot with greater polarity was detected. The reaction mixture was diluted with $H_2O$ (20 mL) and was extracted with EtOAc (10 mL×3). The combined organic extract was washed with brine (15 mL), was dried over $Na_2SO_4$, was filtered and was concentrated under reduced pressure to give a residue. The residue was purified by prep-TLC (dichloromethane:methanol=10:1) to give compound 12 (40.0 mg) as a yellow solid. MS: 393.0 $(M+H)^+$. $^1H$ NMR: 400 MHz DMSO-$d_6$ δ (ppm) 8.16 (s, 1H), 7.18 (t, J=5.8 Hz, 1H), 6.47 (s, 1H), 5.27 (t, J=6 Hz, 1H), 4.90 (s, 1H), 4.58 (d, J=6.8 Hz, 1H), 3.40 (s, 2H), 1.70-1.68 (s, 1H), 1.44 (s, 3H), 1.28-1.24 (m, 1H), 1.19-1.15 (m, 6H), 0.84-0.78 (m, 2H).

Step-2

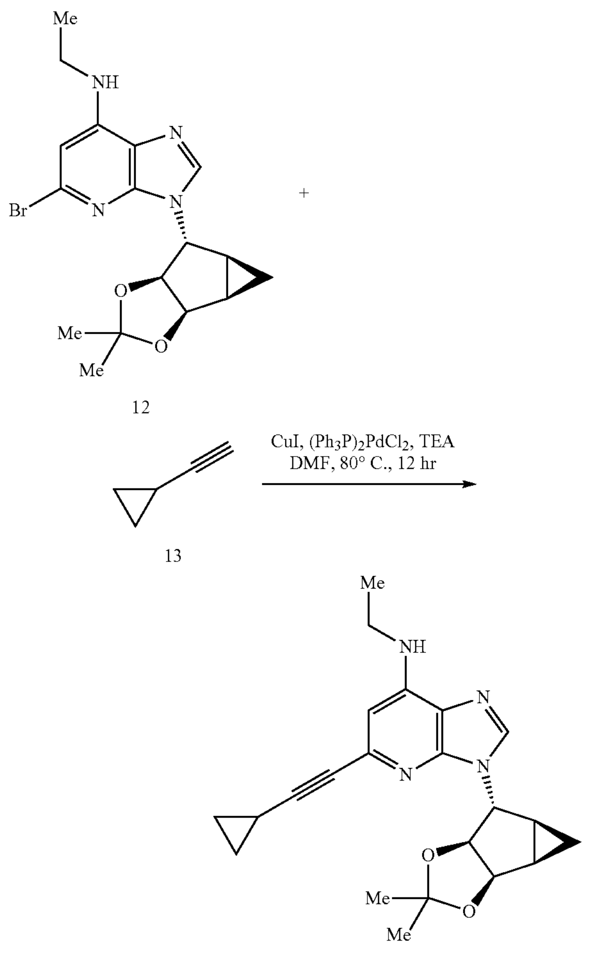

12 + 13 → 14.1

A solution consisting of compound 12 (120.0 mg, 1.00 eq), compound 13 (239.1 mg, 300.0 mL, 11.8 eq), $Pd(PPh_3)_2Cl_2$ (42.8 mg, 0.20 eq), CuI (11.6 mg, 0.20 eq), TEA (436.2 mg, 600.0 μL, 14.13 eq) and DMF (6 mL) was prepared at 20° C. The resulting mixture was stirred at 80° C. for 12 hrs. TLC (petroleum ether:ethyl acetate=10:1) indicated compound 12 was consumed, and one major new spot with greater polarity was detected. The reaction mixture was diluted with $H_2O$ (20 mL) and was extracted with EtOAc (10 mL×3). The combined extract was washed with brine (18 mL), was dried over $Na_2SO_4$, was filtered and was concentrated under reduced pressure to give a residue. The residue was purified by prep-TLC (dichloromethane:methanol=10:1) to give compound 14.1 (120.0 mg, crude) as brown solid. MS: 379.3 $(M+H)^+$. H NMR: 400 MHz DMSO-$d_6$ δ (ppm) 8.18 (s, 1H), 6.81 (t, J=5.8 Hz, 1H), 6.40 (s, 1H), 5.25 (t, J=6 Hz, 1H), 4.95 (s, 1H), 4.52 (d, J=7.2 Hz, 1H), 3.38 (s, 2H), 1.99-1.96 (m, 1H), 1.71-1.69 (m, 1H), 1.57-1.53 (m, 1H), 1.44 (s, 3H), 1.19-1.15 (m, 6H), 1.92-1.75 (m, 6H).

TABLE 6

| Intermediate prepared by procedure of Example 6 | |
|---|---|
| 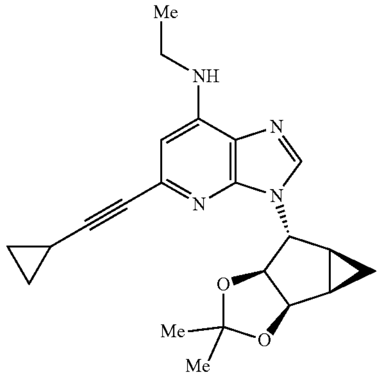 [SMILES: CCNc1cc(C#CC2CC2)nc2c1ncn2[C@@H]1[C@H]2C[C@H]2[C@H]2OC(C)(C)O[C@H]21] | 14.1 |

Example 7. Preparation of N-(2,2-difluoroethyl)-3-((3aR,3bR,4aS,5R,5aS)-2,2-dimethylhexahydrocyclopropa[3,4]cyclopenta[1,2-d][1,3]dioxol-5-yl)-5-methyl-3H-imidazo[4,5-b]pyridin-7-amine (16.1)

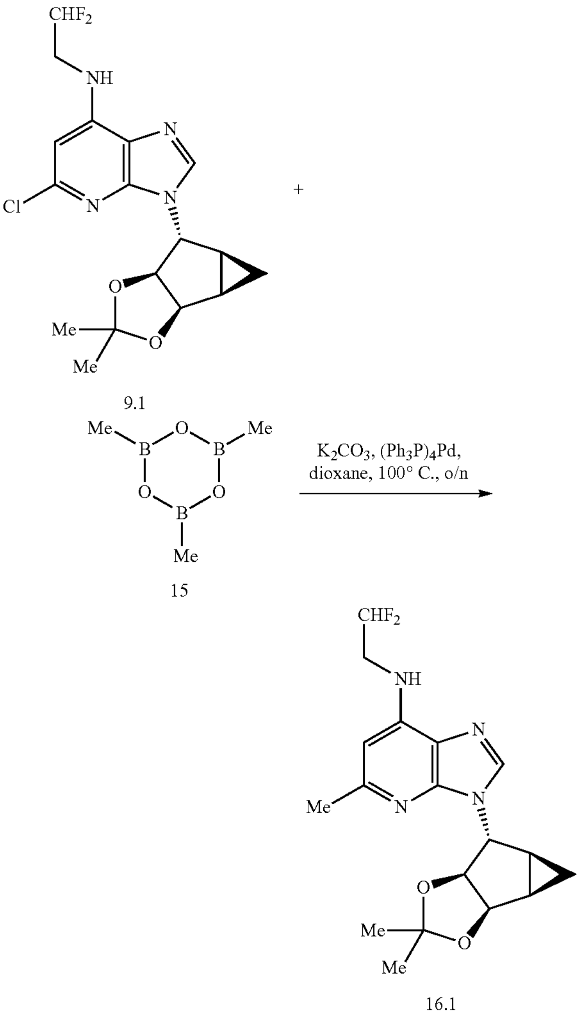

9.1 + 15 → 16.1

To a solution of compound 9.1 (230.0 mg, 1.00 eq), compound 15 (150.1 mg, 167.1 μL, 2.00 eq) and $K_2CO_3$ (330.4 mg, 4.00 eq) in dioxane (3 mL) was added $Pd(PPh_3)_4$ (69.1 mg, 0.10 eq) under $N_2$. The mixture was stirred at 100° C. for 12 hrs. LCMS analysis showed 9.1 was consumed. The mixture was diluted with $H_2O$ (20 mL) and was extracted with EtOAc (20 mL×4). The organic extract was washed with saturated salt water (40 mL×3), was dried over $Na_2SO_4$, was filtered and was concentrated to give a residue. The residue was purified by prep-TLC (petroleum ether: ethyl acetate=1:5) to give compound 16.1 (200.0 mg) as a yellow oil. MS: 365.0 $(M+H)^+$. $^1H$ NMR: 400 MHz DMSO-$d_6$ δ (ppm) 8.15-8.10 (m, 1H), 6.97-6.88 (m, 11H), 6.38 (s, 1H), 6.32-6.00 (m, 1H), 5.35-5.24 (m, 1H), 5.03-4.98 (m, 114), 4.56 (d, J=7.0 Hz, 11H), 4.01-3.85 (m, 2H), 2.40 (s, 3H), 2.00-1.92 (m, 11H), 1.68-1.61 (m, 1H), 1.44 (s, 3H), 1.16 (s, 3H), 0.88-0.77 (m, 2H).

Similarly prepared according to the method of Example 7 were the following compounds:

Substituting 9.2 for 9.1 gave 3-((3aR,3bR,4aS,5R,5aS)-2,2-dimethylhexahydrocyclopropa[3,4]cyclopenta[1,2-d][1,3]dioxol-5-yl)-N-(2-fluoroethyl)-5-methyl-3H-imidazo[4,5-b]pyridin-7-amine (16.2). MS 347 $(M+H)^+$;

Substituting 9.3 for 9.1 gave 3-((3aR,3bR,4aS,5R,5aS)-2,2-dimethylhexahydrocyclopropa[3,4]cyclopenta[1,2-d][1,3]dioxol-5-yl)-N-ethyl-5-methyl-3H-imidazo[4,5-b]pyridin-7-amine (16.3). MS: 329.1 $(M+H)^+$. $^1H$ NMR: 400 MHz DMSO-$d_6$ δ (ppm) 8.04 (s, 1H), 6.62-6.53 (m, 1H), 6.21 (s, 11H), 5.33-5.27 (m, 1H), 4.97 (s, 1H), 4.59-4.53 (m, 11H), 3.41-3.34 (m, 2H), 2.39 (s, 3H), 2.00-1.92 (m, 1H), 1.68-1.61 (m, 1H), 1.44 (s, 31H), 1.20-1.15 (m, 6H), 0.84-0.76 (m, 2H);

Substituting 9.6 for 9.1 gave N-(2,5-difluorobenzyl)-3-((3aR,3bR,4aS,5R,5aS)-2,2-dimethylhexahydrocyclopropa[3,4]cyclopenta[1,2-d][1,3]dioxol-5-yl)-5-methyl-3H-imidazo[4,5-b]pyridin-7-amine (16.4). MS 427 $(M+H)^+$.

TABLE 7

| Intermediates prepared by procedure of Example 7 | |
|---|---|
| 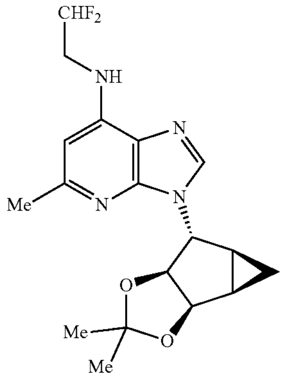 [SMILES: Cc1cc(NCC(F)F)c2ncn([C@@H]3[C@H]4C[C@H]4[C@H]4OC(C)(C)O[C@H]43)c2n1] | 16.1 |

TABLE 7-continued

| Intermediates prepared by procedure of Example 7 | |
|---|---|
| 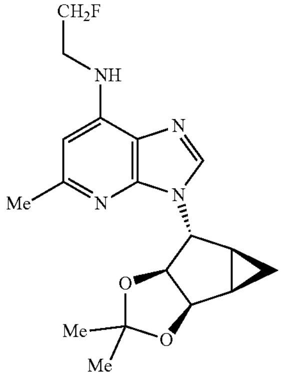 | 16.2 |
| 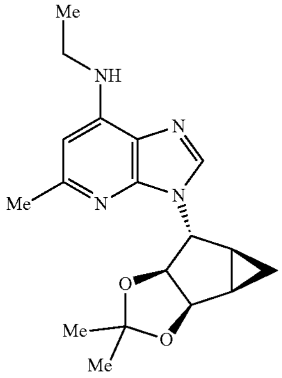 [SMILES: CCNc1cc(C)nc2c1ncn2[C@@H]1[C@H]2C[C@H]2[C@H]2OC(C)(C)O[C@H]21] | 16.3 |
| 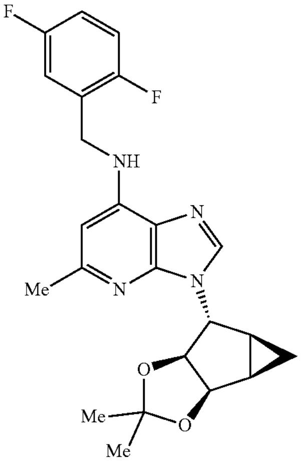 [SMILES: Cc1cc(NCc2cc(F)ccc2F)c2ncn([C@@H]3[C@H]4C[C@H]4[C@H]4OC(C)(C)O[C@H]43)c2n1] | 16.4 |

Example 8. Preparation of 2-chloro-N-(2,2-difluoroethyl)-9-((3aR,3bS,4aS,5R,5aS)-3b-(fluoromethyl)-2,2-dimethylhexahydrocyclopropa[3,4]cyclopenta[1,2-d][1,3]dioxol-5-yl)-9H-purin-6-amine (23)

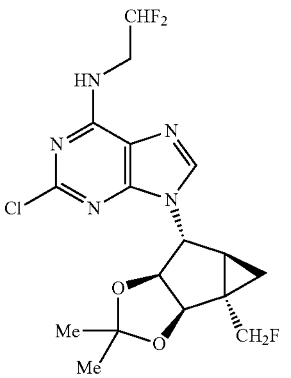

23

Step-1

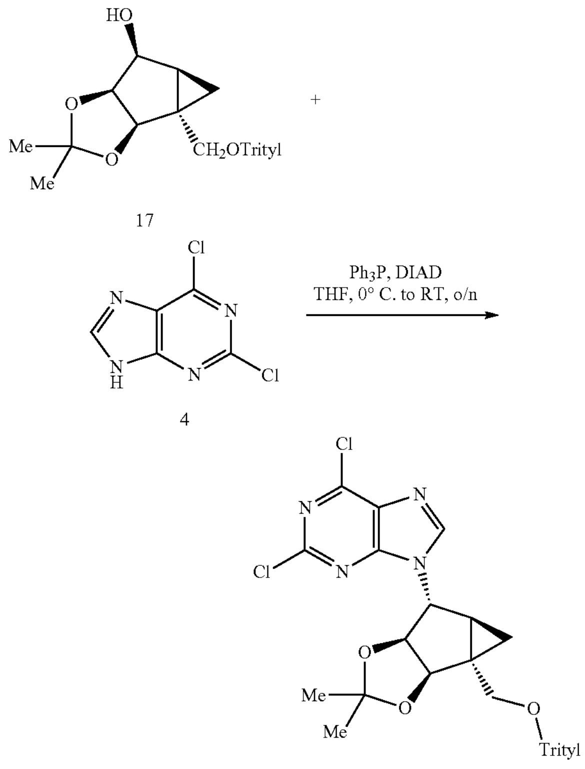

17 + 4 → 18.1

To a solution of compound 4 (2.00 g, 1.00 eq) and compound 17 (5.15 g, 1.10 eq) in THF (70 mL) was added DIAD (4.28 g, 4.11 mL, 2.00 eq) and $PPh_3$ (5.55 g, 2.00 eq) at 20° C. The resulting mixture was stirred at 20° C. for 12 hrs. The reaction mixture was diluted with $H_2O$ (200 mL) and was extracted with EtOAc (90 mL×3). The organic extract was washed with brine (150 mL), was dried over $Na_2SO_4$, was filtered and was concentrated under reduced pressure to give a residue. The residue was purified by column chromatography ($SiO_2$, petroleum ether:ethyl acetate=10:1 to 0:1) to give compound 18.1 (4.30 g, crude) as light yellow solid. $^1$H NMR: 400 MHz DMSO-$d_6$ δ (ppm) 8.78 (s, 1H), 7.39-7.24 (m, 15H), 5.20 (d, J=7.2 Hz, 1H), 5.05 (s, 1H), 4.83 (d, J=6.4 Hz, 1H), 4.79-4.75 (m, 1H), 4.06-4.01 (m, 1H), 1.83-1.79 (m, 1H), 1.47 (s, 3H), 1.18 (s, 3H), 1.04-1.06 (m, 2H).

Similarly prepared by the procedure of Step-1 by substituting 5,7-dichloro-3H-imidazo[4,5-b]pyridine for compound 4 was 5,7-dichloro-3-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-3H-imidazo[4,5-b]pyridine (18.2). MS: 611.9 $(M+H)^+$. $^1$H NMR: 400 MHz DMSO-$d_6$ $\delta_{(ppm)}$ 8.67 (s, 1H), 7.60 (s, 1H), 7.38-7.24 (m, 15H), 5.25 (d, J=7.2 Hz, 1H), 5.05 (s, 1H), 4.79 (d, J=7.2 Hz, 1H), 3.38-3.28 (m, 2H), 1.75-1.72 (m, 1H), 1.46 (s, 3H), 1.19 (s, 3H), 1.03 (t, J=4.8 Hz, 1H), 0.95-0.93 (m, 1H);

Similarly prepared by the procedure of Step-1 by substituting 5-bromo-7-bromo/chloro-3H-imidazo[4,5-b]pyridine for compound 4 was 5-bromo-,7-bromo/chloro-3-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-3H-imidazo[4,5-b]pyridine (18.3). MS: 658.1 $(M+H)^+$ and 702.0 $(M+H)^+$.

Step-2

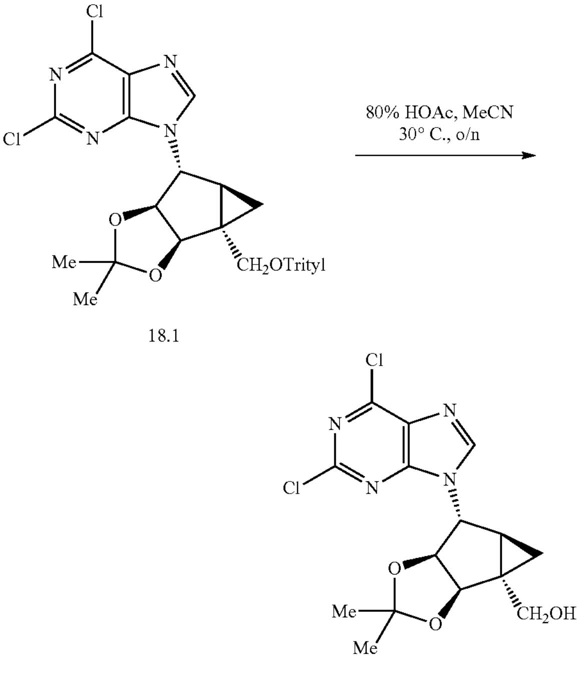

18.1 → 19.1

A mixture of compound 18.1 (4.20 g, crude), AcOH (44.1 g, 42.0 mL, 80.0% in water, 220.0 eq) in ACN (13 mL) was stirred at 30° C. for 12 hrs. TLC (petroleum ether:ethyl acetate=0:1) indicated ~0% of compound 18.1 remained, and one major new spot with greater polarity was detected. The reaction mixture was basified with aq. $NH_3 \cdot H_2O$ to pH~8 and was extracted with EtOAc (50 mL×3). The combined organic extract was washed with brine (70 mL), was dried over $Na_2SO_4$, was filtered and was concentrated under reduced pressure to give a residue. The residue was purified by column chromatography ($SiO_2$, Petroleum ether:

Ethyl acetate=50:1 to 0:1) to give compound 19.1 (840.0 mg) as white solid. MS: 371.1 $(M+H)^+$. $^1H$ NMR: 400 MHz DMSO-$d_6$ δ (ppm) 8.85 (s, 1H), 5.18 (d, J=7.2 Hz, 1H), 4.99 (s, 1H), 4.95 (t, J=5.4 Hz, 1H), 4.72 (d, J=3.6 Hz, 1H), 3.85-3.81 (m, 1H), 3.79-3.44 (m, 1H), 1.75-1.72 (m, 1H), 1.45 (s, 3H), 1.16 (s, 3H), 0.99-0.97 (m, 1H), 0.95-0.92 (m, 1H).

Similarly prepared by the procedure of Step-2 by substituting compound 18.2 for 18.1 was ((3aR,3bR,4aS,5R,5aS)-5-(5,7-dichloro-3H-imidazo[4,5-b]pyridin-3-yl)-2,2-dimethylhexahydrocyclopropa[3,4]cyclopenta[1,2-d][1,3]dioxol-3b-yl)methanol (19.2). MS: 370.1 $(M+H)^+$. $^1H$ NMR: 400 MHz DMSO-$d_6$ δ (ppm) 8.75 (s, 1H), 7.67 (s, 1H), 5.20 (d, J=7.2 Hz, 1H), 5.01 (s, 1H), 4.95 (t, J=5.2 Hz, 1H), 4.66-4.65 (m, 2H), 3.47-3.43 (m, 1H), 1.72-1.69 (m, 1), 1.45 (s, 3H), 1.16 (s, 3H), 1.00-0.92 (m, 2H).

Similarly prepared by the procedure of Step-2 by substituting compound 18.3 for 18.1 was ((3aR,3bR,4aS,5R,5aS)-5-(5-bromo-7-bromo/chloro-3H-imidazo[4,5-b]pyridin-3-yl)-2,2-dimethylhexahydrocyclopropa[3,4]cyclopenta[1,2-d][1,3]dioxol-3b-yl)methanol (19.3). MS: 416.0 $(M+H)^+$ and 460.0 $(M+H)^+$ Step-3

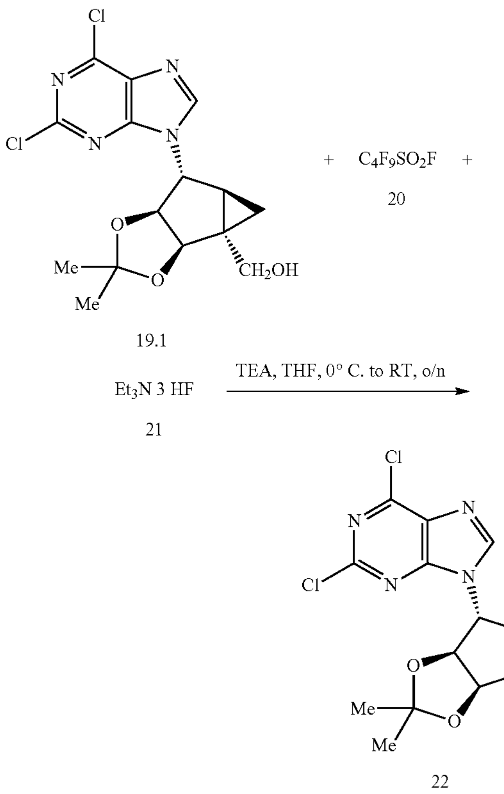

19.1 20 21 22

To a solution of compound 19.1 (200.0 mg, 1.00 eq) in THF (2 mL) was added compound 20 (651.0 mg, 378.5 μL, 4.00 eq), compound 21 (347.4 mg, 351.2 μL, 4.00 eq) and TEA (436.1 mg, 599.9 μL, 8.00 eq) at 0° C. The resulting mixture was stirred at 20° C. for 12 hrs. TLC (petroleum ether:ethyl acetate=3:1) indicated ~0% of compound 19 remained, and one major new spot with lower polarity was detected. The reaction mixture was concentrated under reduced pressure to give a residue. The residue was purified by prep-TLC (petroleum ether:ethyl acetate=3:1) to give compound 22 (0.17 g) as light yellow solid. MS: 373.1 $(M+H)^+$. $^1H$ NMR: 400 MHz DMSO-$d_6$ δ (ppm) 8.71 (s, 1H), 5.26 (d, J=7.2 Hz, 1H), 5.08 (d, J=3.2 Hz, 1H), 4.99-4.84 (m, 2H), 4.46-4.31 (m, 1H), 1.94 (t, J=7.6 Hz, 1H), 1.47 (s, 3H), 1.18 (s, 3H), 1.13 (d, J=7.6 Hz, 1H).

Step-4

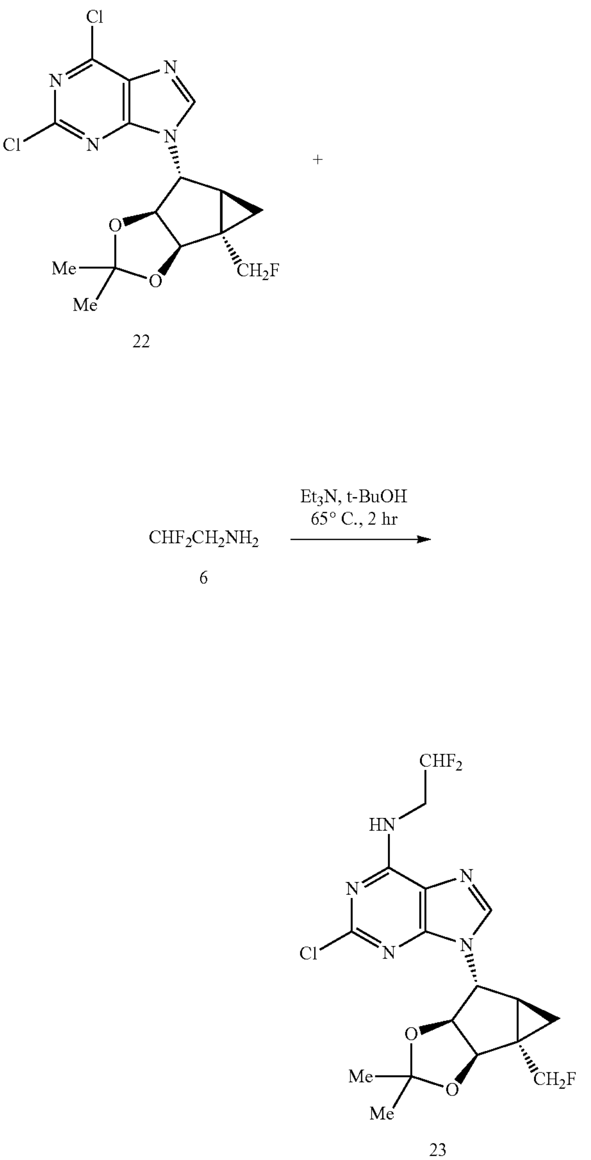

22 6 23

To a solution of compound 22 (0.17 g 1.00 eq) and compound 6 (110.7 mg, 3.00 eq) in t-BuOH (10 mL) was added TEA (230.4 mg, 317.0 μL, 5.00 eq) at 20° C. The resulting mixture was stirred at 65° C. for 2 hrs. The reaction mixture was diluted with $H_2O$ (30 mL) and was extracted with EtOAc (10 mL×3). The combined organic extract was washed with brine (15 mL×3), was dried over $Na_2SO_4$, was filtered and was concentrated under reduced pressure to give compound 23 (0.17 g, crude) as light yellow solid. MS: 418.1 $(M+H)^+$. $^1H$ NMR: 400 MHz DMSO-$d_6$ δ (ppm) 8.65 (s, 1H), 8.22 (s, 1H), 6.18 (t, J=56 Hz, 1H), 5.25 (d, J=7.2 Hz, 1H), 4.95 (d, J=2.4 Hz, 1H), 4.84-4.73 (m, 2H), 4.47-4.32 (m, 1H), 3.85 (s, 2H), 1.83-1.80 (m, 1H), 1.46 (s, 3H), 1.18 (s, 3H), 1.11-1.06 (m, 2H).

TABLE 8

| Intermediate prepared by procedure of Example 8 | |
|---|---|
| 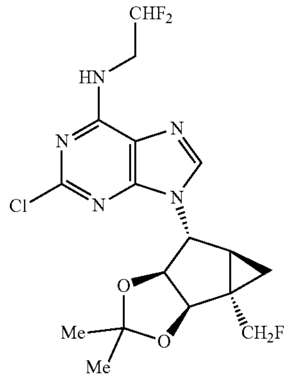 | 23 |

Example 9. Preparation of 2-chloro-9-((3aR,3bS,4aS,5R,5aS)-3b-(difluoromethyl)-2,2-dimethylhexahydrocyclopropa[3,4]cyclopenta[1,2-d][1,3]dioxol-5-yl)-N-ethyl-9H-purin-6-amine (26.1)

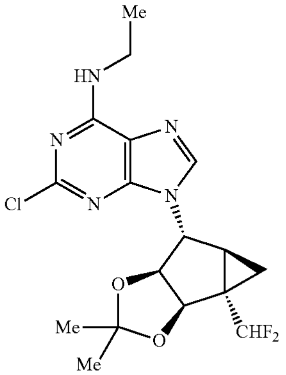

26

Step-1

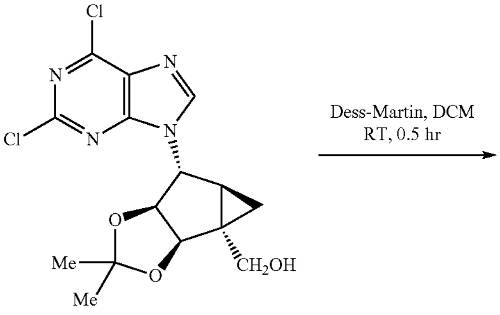

19.1

-continued

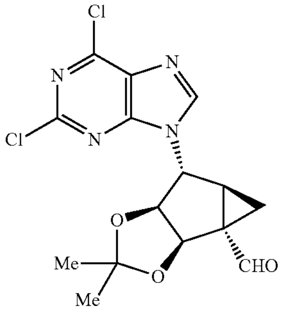

24

A solution of compound 19.1 (370.0 mg, 1.00 eq), Dess-Martin periodinane (507.3 mg, 0.37 uL, 1.20 eq) in DCM (4 mL) was stirred at 20° C. for 0.5 hr. LC-MS analysis showed ~0% of compound 19.1 remained. The mixture was filtered with a diatomite filter, was diluted with 5% aqueous $Na_2SO_3$ (20 mL), 5% aqueous $NaHCO_3$ (40 mL) and was extracted with DCM (25 mL×5). The organic extract was washed with brine (60 mL), was dried over $Na_2SO_4$, was filtered and was concentrated under reduced pressure to give compound 24 (360.0 mg, crude) as light yellow solid. MS: 369.1 $(M+H)^+$.

Step-2

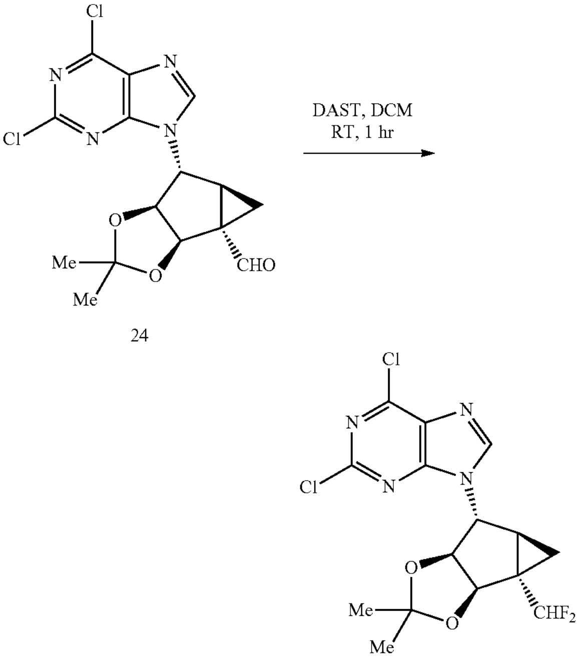

24

25

A solution of compound 24 (360.0 mg, 1.00 eq) in DCM (4 mL), DAST (738.7 mg, 0.61 μL, 4.70 eq) in DCM (0.5 mL) was stirred at 20° C. for 1 hr. TLC (petroleum ether: ethyl acetate=0:1) indicated ~0% of compound 24 remained. The reaction mixture was diluted with sat. aqueous $NaHCO_3$ (25 mL) and was extracted with DCM (20 mL×3). The combined organic extract was washed with brine (30 mL), was dried over $Na_2SO_4$, was filtered and was concentrated under reduced pressure to give a residue. The residue was purified by prep-TLC (petroleum ether:ethyl acetate=0:1) to give compound 25 (260.0 mg) as a light yellow solid. MS: 391.0 $(M+H)^+$. $^1H$ NMR: 400 MHz DMSO-$d_6$ $\delta_{(ppm)}$ 8.68 (s, 1H), 6.42-6.13 (m, 1H), 5.39 (d, J=7.2 Hz, 1H), 5.11 (s, 11H), 4.92 (d, J=6.8 Hz, 1H), 2.16-2.13 (m, 1H), 1.48 (s, 3H), 1.34-1.32 (m, 1H), 1.19 (s, 3H), 1.17-1.15 (m, 1H).

Step-3

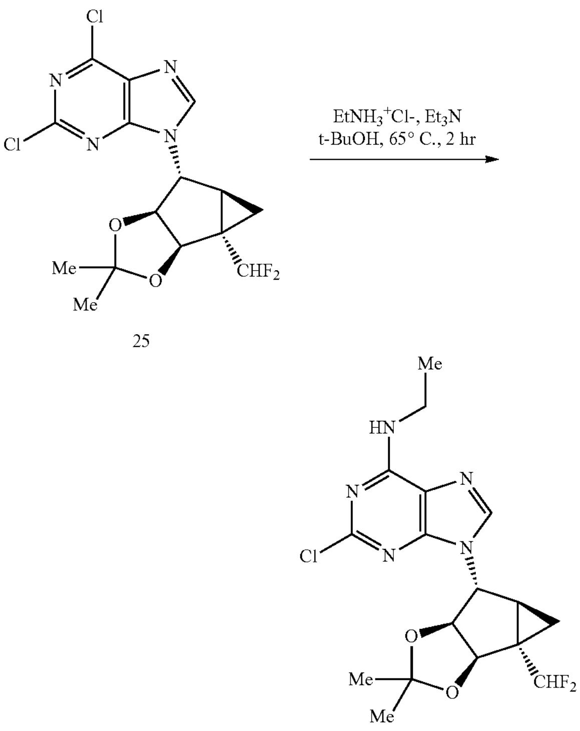

25

26.1

To a solution of compound 25 (150.0 mg, 1.00 eq) and ethylamine hydrochloride (62.5 mg, 2.00 eg) in t-BuOH (3 mL) was added TEA (194.0 mg, 0.27 μL, 5.00 eq) at 20° C. The resulting mixture was stirred at 65° C. for 2 hrs. LC-MS analysis showed ~0% of compound 25 remained. The reaction mixture was concentrated under reduced pressure to give compound 26.1 (160.0 mg, crude) as light yellow solid. MS: 400.2 $(M+H)^+$. $^1H$ NMR: 400 MHz DMSO-$d_6$ δ (ppm) 8.38 (s, 1H), 8.10 (s, 1H), 6.42-6.13 (m, 1H), 5.35 (d, J=6.4 Hz, 1H), 4.96 (s, 1H), 4.78 (d, t=3.6 Hz, 1H), 3.47-3.44 (m, 2H), 2.01-1.99 (m, 11H), 1.46 (s, 3H), 1.31-1.28 (m, 1H), 1.22-1.14 (m, 7H).

Similarly prepared by the method of Example 9 by substituting compound 19.2 in Step-1 was 5-chloro-3-((3aR,3bS,4aS,5R,5aS)-3b-(difluoromethyl)-2,2-dimethylhexahydrocyclopropa[3,4]cyclopenta[1,2-d][1,3]dioxol-5-yl)-N-ethyl-3H-imidazo[4,5-b]pyridin-7-amine (26.2). MS: 399.0 $(M+H)^+$. $^1H$ NMR: 400 MHz MeOD δ (ppm) 8.02 (s, 1H), 6.49-6.20 (m, 2H), 5.47 (d, J=7.2 Hz, 1H), 5.00 (s, 1H), 4.79 (d, J=6.8 Hz, 1H), 3.41-3.35 (m, 2H), 1.90-1.87 (m, 1H), 1.53 (s, 3H), 1.34-1.25 (s, 8H);

Similarly prepared by the method of Example 9 by substituting compound 19.3 in Step-1 was 5-bromo-3-((3aR,3bS,4aS,5R,5aS)-3b-(difluoromethyl)-2,2-dimethylhexahydrocyclopropa[3,4]cyclopenta[1,2-d][1,3]dioxol-5-yl)-N-ethyl-3H-imidazo[4,5-b]pyridin-7-amine (26.3). MS: 443.1 $(M+H)^+$. $^1H$ NMR: 400 MHz DMSO-$d_6$ δ (ppm) 8.06 (s, 1H), 7.25 (t, J=5.6 Hz, 1H), 6.19-6.18 (m, 1H), 6.53-6.18 (m, 1H), 5.36 (d, J=7.2 Hz, 1H), 4.99 (s, 1H), 4.74 (d, J=6.8 Hz, 1H), 3.48-3.35 (m, 2H), 1.98-1.91 (m, 1H), 1.46 (s, 3H), 1.33-1.25 (m, 2H), 1.20-1.16 (m, 6H).

TABLE 9

| Intermediates prepared by the procedure of Example 9 | |
|---|---|
| 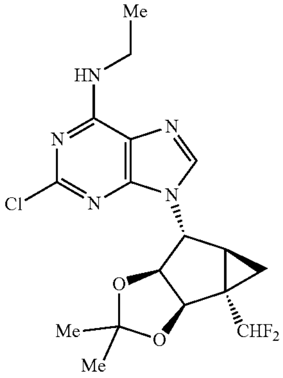 [SMILES: CCNc1nc(Cl)nc2c1ncn2[C@H]1[C@@H]2OC(C)(C)O[C@@H]2[C@]2(C(F)F)C[C@H]12] | 26.1 |
| 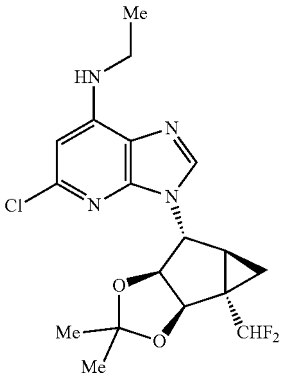 [SMILES: CCNc1cc(Cl)nc2c1ncn2[C@H]1[C@@H]2OC(C)(C)O[C@@H]2[C@]2(C(F)F)C[C@H]12] | 26.2 |
| 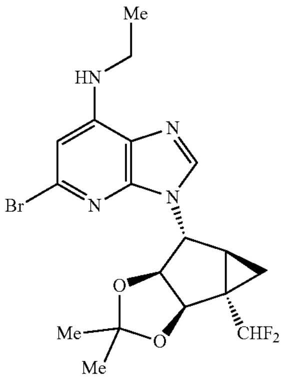 | 26.3 |

Example 10. Preparation of 2-chloro-N-(2,2-difluoroethyl)-9-((3aR,3bR,4aS,5R,5aS)-2,2,3b-trimethylhexahydrocyclopropa[3,4]cyclopenta[1,2-d][1,3]dioxol-5-yl)-9H-purin-6-amine (34)

34

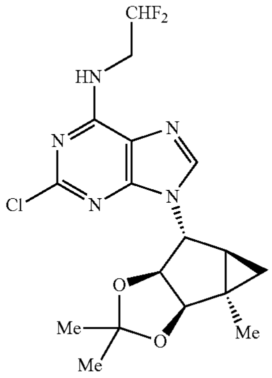

Step-1

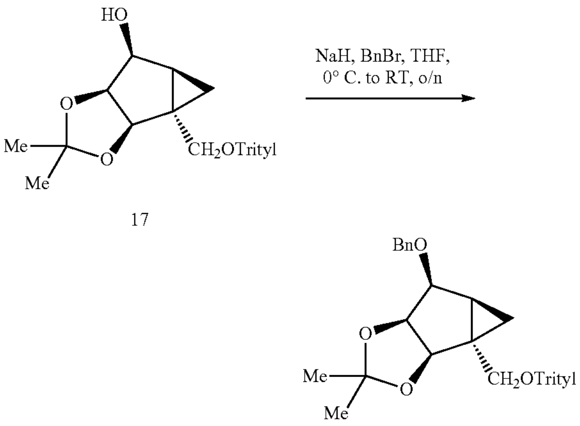

17

27

To a solution of compound 17 (3.00 g, 1.00 eq) in THF (30 mL) was added NaH (298.2 mg, 60.0% in mineral oil, 1.10 eq) at 0° C., the reaction mixture was stirred at 0° C. for 0.5 hr and then BnBr (3.48 g, 2.42 mL, 3.00 eq) and NaI (10.1 mg 0.010 eq) were added at 0° C. The reaction mixture was stirred at 20° C. for 12 hrs. TLC (petroleum ether:ethyl acetate=5:1) indicated ~0% of compound 17 remained, and one major new spot with lower polarity was detected. The reaction mixture was quenched by addition saturated aqueous $NH_4C_1$ (100 mL) at 0° C., and was extracted with EtOAc (50 mL×3). The organic extract was washed with brine (80 mL), was dried over $Na_2SO_4$, was filtered and was concentrated under reduced pressure to give a residue. The residue was purified by column chromatography ($SiO_2$, petroleum ether:ethyl acetate=1:0 to 0:1) to give compound 27 (3.60 g) as a yellow oil. $^1$H NMR: 400 MHz DMSO-$d_6$ δ (ppm) 7.37-7.25 (m, 20H), 4.85 (d, J=6.8 Hz, 1H), 4.63 (t, J=1.2 Hz, 1H), 4.54-4.50 (m, 2H), 4.30 (t, J=5.4 Hz, 1H), 3.16 (d, J=10 Hz, 1H), 2.81 (d, J=9.6 Hz, 1H), 1.62-1.60 (m, 1H), 1.41 (s, 3H), 1.21-1.19 (m, 4H), 0.51-0.48 (m, 1H).

Step-2

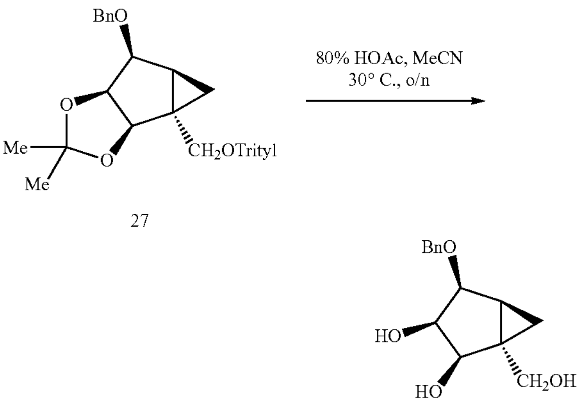

27

28

A mixture of compound 27 (3.60 g, 1.00 eq), AcOH (113.4 g, 108.0 mL, 80.0% aqueous) in acetonitrile (33 mL) was stirred at 30° C. for 12 hrs. TLC (dichloromethane:methanol=10:1) indicated ~0% of compound 27 remained, and one major new spot with greater polarity was detected. The reaction mixture was basified with aqueous ammonia, to pH ~8 and was concentrated under reduced pressure to give a residue. The residue was stirred with EtOAc (20 mL) and was filtered. The filtrate was concentrated under reduced pressure to give a residue. The residue was purified by column chromatography ($SiO_2$, dichloromethane:methanol=1:0 to 0:1) to give compound 28 (2.00 g, crude) as a yellow oil. $^1$H NMR: 400 MHz DMSO-$d_6$ δ (ppm) 7.38-7.33 (m, 4H), 7.30-7.26 (m, 1H), 4.57 (d, J=12 Hz, 1H), 4.49-4.40 (m, 3H), 4.20-4.18 (m, 1H), 4.06-3.98 (m, 2H), 3.88-3.85 (m, 1H), 3.78 (d, J=12 Hz, 1H), 3.01 (d, J=11.6 Hz, 1H), 1.38-1.36 (m, 1H), 1.30 (t, J=4 Hz, 1H), 0.29-0.26 (m, 1H).

Step-3

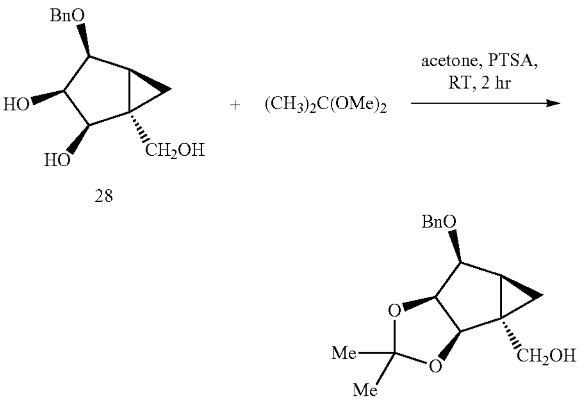

28

29

To a solution of compound 28 (2.00 g, crude) in acetone (200 mL) was added 2,2-dimethoxypropane (4.99 g, 5.87 mL, 6.00 eq) and TsOH·$H_2O$ (1.38 g, 1.00 eg) at 20° C. The resulting mixture was stirred at 20° C. for 2 hrs. TLC analysis (petroleum ether:ethyl acetate=0:1) indicated ~0% of compound 28 remained, and one major new spot with lower polarity was detected. The reaction mixture was basified with aqueous ammonia, to pH~8, was filtered and was concentrated under reduced pressure to give a residue. The residue was purified by column chromatography ($SiO_2$, petroleum ether:ethyl acetate=1:0 to 0:1) to give compound 29 (1.50 g) as light yellow solid. $^1H$ NMR: 400 MHz DMSO-$d_6$ δ (ppm) 7.35 (d, J=4.4 Hz, 4H), 7.31-7.27 (m, 1H), 4.81 (d, J=6.4 Hz, 1H), 4.61-4.56 (m, 2H), 4.56-4.48 (m, 2H), 4.21 (d, J=8 Hz, 1H), 3.64-3.60 (m, 1H), 3.11-3.07 (m, 1H), 1.62-1.58 (m, 1H), 1.42 (s, 3H), 1.21 (s, 3H), 1.15 (t, J=4.4 Hz, 1H), 0.53-0.50 (m, 1H).

Step-4

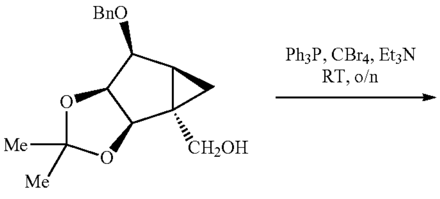

29

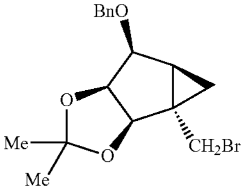

30

To a solution of compound 29 (500.0 mg, 1.00 eq) in DCM (10 mL) was added $CBr_4$ (1.14 g, 2.00 eq) $PPh_3$ (903.3 mg, 2.00 eq) and TEA (522.8 mg, 719.1 μL, 3.00 eq). The mixture was stirred at 25° C. for 16 hrs. TLC (petroleum ether:ethyl acetate=1:1) showed complete reaction. The mixture was quenched by adding $H_2O$ (20 mL) and was extracted with DCM (10 mL×3). The organic extract was washed with sat. aqueous NaCl (20 mL), was dried over $Na_2SO_4$, was filtered and was concentrated under reduced pressure to give a residue. The residue was purified by silica gel chromatography ($SiO_2$, petroleum ether:ethyl acetate=100:1 to 50:1) to obtain compound 30 (500.0 mg) as a white solid. $^1H$ NMR: 400 MHz DMSO-$d_6$ δ (ppm) 7.36-7.29 (m, 5H), 4.82 (d, J=6.0 Hz, 1H), 4.62 (t, J=6.4 Hz, 1H), 4.56-4.48 (m, 2H), 4.24-4.21 (m, 1H), 3.74-3.59 (m, 2H), 1.84-1.80 (m, 1H), 1.49-1.47 (m, 1H), 1.43 (s, 3H), 1.22 (s, 3H), 0.87-0.84 (m, 1H).

Step-5

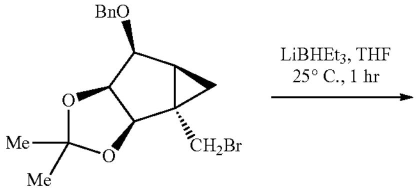

30

-continued

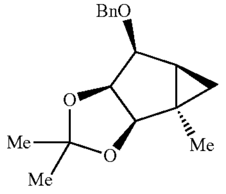

31

To a solution of compound 30 (750.0 mg, 1.00 eq) in THF (10 mL) was added $LiBHEt_3$ (1 M, 8.49 mL, 4.00 eq) at 0° C. The mixture was stirred at 25° C. for 1 hr. TLC analysis (petroleum ether:ethyl acetate=8:1) showed complete reaction. The mixture was quenched by adding $H_2O$ (20 mL) and was extracted with ethyl acetate (10 mL×3). The organic extract was washed with sat. aqueous NaCl (20 mL), was dried over $Na_2SO_4$, was filtered and was concentrated under reduced pressure to give a residue. The residue was purified by Pre-TLC (petroleum ether:ethyl acetate=5:1) to obtain compound 31 (600.0 mg, 90.0% purity) as a white solid. $^1H$ NMR: 400 MHz DMSO-$d_6$ 3 (ppm) 7.35-7.27 (m, 5H), 4.55-4.67 (m, 4H), 44.24 (s, 11H), 1.51-1.48 (m, 11H), 1.42 (s, 3H), 1.17-1.14 (m, 7H), 0.39-0.36 (m, 11H).

Step-6

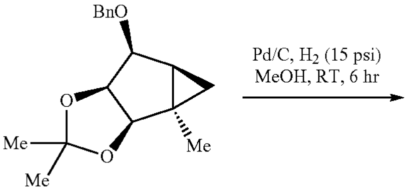

31

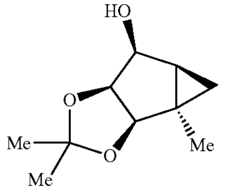

32

To a solution of compound 31 (600.0 mg, 1.00 eq) in MeOH (15 mL) was added 10% Pd/C (500.0 mg) under $N_2$ atmosphere. The suspension was degassed and was purged with $H_2$ for 3 times. The mixture was stirred under $H_2$ (15 Psi) at 25° C. for 6 hrs. TLC analysis (petroleum ether:ethyl acetate=5:1) showed ~⅓ of compound 31 remained. Solids were removed by filtration and the filtrates were concentrated under reduced pressure. The residue was purified by Pre-TLC (petroleum ether:ethyl acetate=3:1) to obtain compound 32 (150.0 mg) as white solid. $^1H$ NMR: 400 MHz DMSO-$d_6$ δ (ppm) 4.49-4.48 (m, 1H), 4.37-4.33 (m, 3H), 1.42-1.39 (m, 4H), 1.78 (s, 3H), 1.13-1.10 (m, 4H), 0.30-0.26 (m, 1H).

Step-7

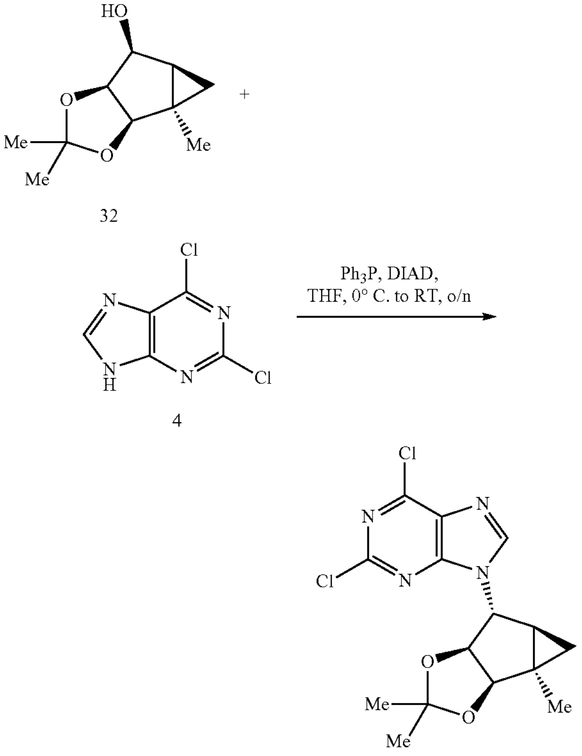

32

4

33

To a solution of compound 32 (170.0 mg, 1.00 eq) in THF (4 mL) was added $PPh_3$ (484.1 mg, 2.00 eq) and DIAD (373.1 mg, 358.8 uL, 2.00 eq) at 0° C. under $N_2$. The mixture was stirred at 20° C. for 15 min, compound 4 (209.3 mg, 1.20 eq) was added to the mixture in one portion. The resulting mixture was stirred at 20° C. for 1 hr. TLC (petroleum ether:ethyl acetate=1:1) showed complete reaction. The mixture was concentrated under reduced pressure. The residue was purified by Prep-TLC (petroleum ether: ethyl acetate=1:1) to obtain compound 33 (130.0 mg, 55.0% purity) as a yellow oil. MS: 355.0 $(M+H)^+$. $^1H$ NMR: 400 MHz DMSO-$d_6$ δ (ppm) 8.75 (s, 1H), 5.03-4.99 (m, 2H), 4.78-4.74 (m, 1H), 1.56-1.52 (m, 1H), 1.45 (s, 3H), 1.39 (s, 3H), 1.15 (s, 3H), 0.90 (t, J=4.8 Hz, 0.74-0.70 (m, 1H).

Step-8

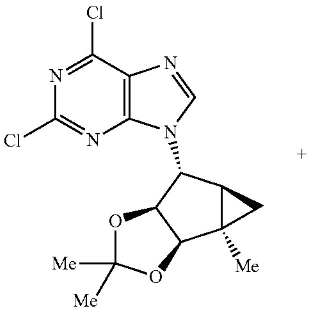

33

-continued

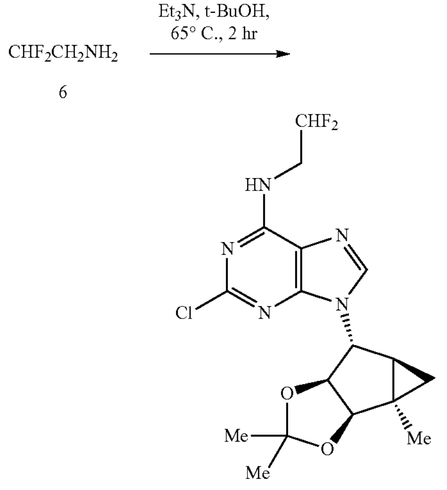

6

34

To a solution of compound 33 (180.0 mg, 55.0% purity, 1.00 eq) in t-BuOH (5 mL) was added compound 6 (67.8 mg, 3.00 eq) and TEA (84.6 mg, 116.4 μL, 3.00 eq). The mixture was stirred at 65° C. for 1 hr. TLC (petroleum ether:ethyl acetate=0:1) showed complete reaction. The mixture was concentrated under reduced pressure. The residue was diluted with ethyl acetate (10 mL×3) and was extracted with water (15 mL). The organic layer was washed with brine (20 mL), was dried over $Na_2SO_4$, was filtered and was concentrated under reduced pressure to give a residue to obtain compound 34 (150.0 mg) as a yellow oil. MS: 400.0 (M+H)+$^1$H NMR: 400 MHz DMSO-$d_6$ δ(ppm) 8.60 (s, 1H), 8.25 (s, 1H), 6.33-6.04 (m, 1H), 5.01 (d, J=6.8 Hz, 1H), 4.86 (s, 1H), 4.63 (d, J=7.2 Hz, 1H), 3.85 (s, 2H), 1.44 (s, 3H), 1.37 (s, 3H), 1.27-1.19 (m, 2H), 1.16 (s, 3H), 0.70-0.67 (m, 1H).

Example 11. Preparation of (1R,2R,3S,4R,5S)-4-(2-chloro-6-((2,2-difluoroethyl)amino)-9H-purin-9-yl) bicyclo[3.1.0]hexane-2,3-diol (35)

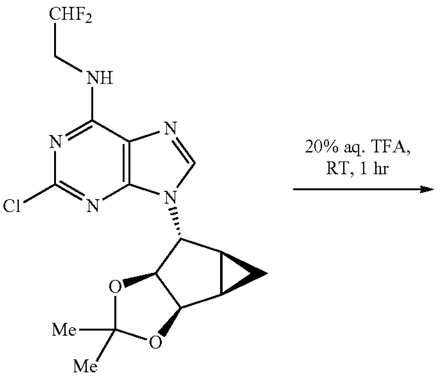

7.1

-continued

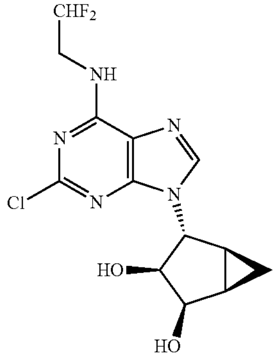

35

A solution of compound 7.1 (110.0 mg, 1.00 eq) in 20% aqueous TFA (10 mL) was stirred at 20° C. for hr. LCMS analysis showed the starting material was consumed completely. The reaction mixture was concentrated under reduced pressure to give a residue. The residue was purified by prep-HPLC (column: Phenomenex Gemini-NX C18 75*30 mm*3 um; mobile phase: [water (0.05% $NH_3H_2O$+ 10 mM $NH_4HCO_3$)-ACN]; B %: 5%-35%, 8 min) to give compound 35 (87.2 mg) as white solid. MS: 346.1 $(M+H)^+$. $^1$H NMR: 400 MHz DMSO-$d_6$ δ (ppm) 8.69-8.40 (m, 1H), 8.28 (s, 1H), 6.37-6.01 (m, 11H), 5.15 (d, J=4.4 Hz, 1H), 4.70-4.49 (m, 3H), 3.91-3.72 (m, 3H), 1.87-1.78 (m, 1H), 1.55-1.43 (m, 1H), 1.12-1.05 (m, 1H), 0.67-0.59 (m, 1H).

Similarly prepared by substituting for compound 7.1 in the method of Example 11 were the following compounds:

Compound 7.2 gave (1R,2R,3S,4R,5S)-4-(2-chloro-6-((2-fluoroethyl)amino)-9H-purin-9-yl)bicyclo[3.1.0]hexane-2,3-diol (36). MS: 328.1 $(M+H)^+$. $^1$H NMR: 400 MHz DMSO-$d_6$ δ (ppm) 8.46-8.40 (m, 1H), 8.23 (s, 1H), 5.13 (d, J=4.4 Hz, 1H), 4.70-4.48 (m, 5H), 3.84-3.66 (m, 3H), 1.85-1.78 (m, 1H), 1.54-1.46 (m, 1H), 1.13-1.06 (m, 1H), 0.68-0.58 (m, 1H);

Compound 7.3 gave (1R,2R,3S,4R,5S)-4-(2-chloro-6-((2,2,2-trifluoroethyl)amino)-9H-purin-9-yl)bicyclo[3.1.0]hexane-2,3-diol (37). MS: 364.0 $(M+H)^+$. $^1$H NMR: 400 MHz DMSO-$d_6$ δ(ppm) 8.88 (s, 1H), 8.32 (s, 1H), 5.14 (d, J=4.4 Hz, 1H), 4.66 (d, J=1.2 Hz, 1H), 4.63-4.58 (m, 1H), 4.55-4.53 (m, 1H), 4.26 (s, 2H), 3.80 (t, J=5.2 Hz, 1H), 1.84-1.81 (m, 1H), 1.53-1.51 (m, 1H), 1.12-1.09 (m, 1H), 0.64-0.62 (m, 1H);

Compound 11.1 gave (1R,2R,3S,4R,5S)-4-(2-(cyclopropylethynyl)-6-((2,2-difluoroethyl)amino)-9H-purin-9-yl)bicyclo[3.1.0]hexane-2,3-diol (38). MS: 376.1 $(M+H)^+$. $^1$H NMR: 400 MHz DMSO-$d_6$ δ (ppm) 8.27 (s, 1H), 8.13 (s, 1H), 6.34-5.99 (m, 1H), 5.13 (d, J=4.4 Hz, 1H), 4.69 (s, 1H), 4.62-4.50 (m, 2H), 3.96-3.72 (m, 3H), 1.84-1.80 (m, 1H), 1.63-1.53 (m, 1H), 1.52-1.45 (m, 1H), 1.13-1.10 (m, 1H), 0.96-0.88 (m, 2H), 0.84-0.75 (m, 2H), 0.64-0.59 (m, 1H);

Compound 11.1 gave (1R,2R,3S,4R,5S)-4-(2-(cyclopropylethynyl)-6-(ethylamino)-9H-purin-9-yl)bicyclo[3.1.0]hexane-2,3-diol (39). MS: 340.2 $(M+H)^+$. $^1$H NMR: 400 MHz DMSO-$d_6$ δ(ppm) 8.18 (s, 1H), 7.79 (s, 1H), 5.11 (d, J=4.4 Hz, 1H), 4.68 (s, 1H), 4.62-4.51 (m, 2H), 3.75 (t, J=4.8 Hz, 1H), 3.47 (s, 2H), 1.84-1.83 (m, 1H), 1.57-1.49 (m, 2H), 1.18-1.12 (m, 4H), 0.93-0.88 (m, 2H), 0.79-0.78 (m, 2H), 0.62-0.60 (m, 1H);

Compound 9.1 gave (1R,2R,3S,4R,5S)-4-(5-chloro-7-((2,2-difluoroethyl)amino)-3H-imidazo[4,5-b]pyridin-3-yl)bicyclo[3.1.0]hexane-2,3-diol (40). MS: 345.0 $(M+H)^+$. $^1$H NMR: 400 MHz DMSO-$d_6$ δ(ppm) 8.20 (s, 1H), 7.40 (t, J=6.4 Hz, 1H), 6.55 (s, 1H), 6.31-6.16 (m, 1H), 5.09 (d, J=2.8 Hz, 1H), 4.71 (s, 1H), 4.62-4.60 (m, 1H), 4.52-4.51 (m, 1H), 3.98 (br s, 2H), 3.75 (d, J=5.6 Hz, 1H), 1.84-1.81 (m, 1H), 1.50-1.47 (m, 1H), 1.13-1.10 (s, 1H), 0.62-0.60 (m, 1H);

Compound 9.2 gave (1R,2R,3S,4R,5S)-4-(5-chloro-7-((2-fluoroethyl)amino)-3H-imidazo[4,5-b]pyridin-3-yl)bicyclo[3.1.0]hexane-2,3-diol (41). MS: 327.1 $(M+H)^+$. $^1$H NMR: 400 MHz DMSO-$d_6$ δ (ppm) 8.17 (s, 1H), 7.35-7.32 (m, 1H), 6.46 (s, 1H), 5.11 (s, 1H), 4.71-4.53 (m, 5H), 3.81-3.75 (m, 3H), 1.86-1.81 (m, 1H), 1.50-1.48 (m, 1H), 1.14-1.11 (m, 1H), 0.63-0.61 (m, 1H);

Compound 9.3 gave (1R,2R,3S,4R,5S)-4-(5-chloro-7-((2,2,2-trifluoroethyl)amino)-3H-imidazo[4,5-b]pyridin-3-yl)bicyclo[3.1.0]hexane-2,3-diol (42). MS: 363.0 $(M+H)^+$. $^1$H NMR: 400 MHz DMSO-$d_6$ δ (ppm) 8.23 (s, 1H), 7.67 (t, J=6.8 Hz, 1H), 6.64 (s, 1H), 5.10 (d, J=4.4 Hz, 11H), 4.71 (s, 1H), 4.61-4.59 (m, 1H), 4.54-4.47 (m, 3H), 3.76 (t, J=5.2 Hz, 1H), 1.84-1.81 (m, 1H), 1.52-1.50 (m, 1H), 1.13-1.10 (m, 1H), 0.63-0.60 (m, 1H);

Compound 9.4 gave (1R,2R,3S,4R,5S)-4-(5-chloro-7-(ethylamino)-3H-imidazo[4,5-b]pyridin-3-yl)bicyclo[3.1.0]hexane-2,3-diol (43). MS: 309.0 $(M+H)^+$. $^1$H NMR: 400 MHz DMSO-$d_6$ δ(ppm) 8.12 (s, 1H), 7.13 (t, J=5.6 Hz, 1H), 6.33 (s, 1H), 5.08 (t, J=4.4 Hz, 1H), 4.70 (s, 1H), 4.62-4.59 (m, 11H), 4.51 (d, J=7.2 Hz, 1H), 3.75 (t, J=4.8 Hz, 1H), 3.40 (brs, 2H), 1.84-1.82 (m, 1H), 1.49-1.48 (m, 1H), 1.19-1.11 (m, 4H), 0.62-0.60 (m, 1H);

Compound 9.5 gave (1R,2R,3S,4R,5S)-4-(5-chloro-7-(cyclobutylamino)-3H-imidazo[4,5-b]pyridin-3-yl)bicyclo[3.1.0]hexane-2,3-diol (44). MS: 335.0 $(M+H)^+$. $^1$H NMR: 400 MHz DMSO-$d_6$ δ (ppm) 8.14 (s, 1H), 7.41 (d, J=7.2 Hz, 1H), 6.28 (s, 1H), 5.09 (d, J=4.4 Hz, 1H), 4.69 (s, 1H), 4.63-4.57 (m, 1H), 4.51 (d, J=7.2 Hz, 1H), 4.46-4.16 (m, 1H), 3.76-3.71 (m, 1H), 2.35-2.28 (m, 2H), 2.09-1.97 (m, 2H), 1.85-1.78 (m, 1H), 1.74-1.64 (m, 2H), 1.51-1.43 (m, 1H), 1.13-1.08 (m, 1H), 0.65-0.58 (m, 1H);

Compound 9.6 gave (1R,2R,3S,4R,5S)-4-(5-chloro-7-((2,5-difluorobenzyl)amino)-3H-imidazo[4,5-b]pyridin-3-yl)bicyclo[3.1.0]hexane-2,3-diol (45). MS: 407.0 $(M+H)^+$. $^1$H NMR: 400 MHz DMSO-$d_6$ δ (ppm) 8.19 (s, 1H), 7.77-7.74 (m, 1H), 7.28-7.26 (m, 1H), 7.17-7.13 (m, 2H), 6.37 (s, 1H), 5.08 (d, J=4.4 Hz, 1H), 4.70-4.69 (m, 3H), 4.62-4.59 (m, 1H), 4.52-4.50 (m, 1H), 3.76 (t, J=4.8 Hz, 1H), 1.84-1.80 (m, 1H), 1.50-1.48 (m, 1H), 1.13-1.10 (m, 11H), 0.62-0.60 (m, 11H);

Compound 14.1 gave (1R,2R,3S,4R,5S)-4-(5-(cyclopropylethynyl)-7-(ethylamino)-3H-imidazo[4,5-b]pyridin-3-yl)bicyclo[3.1.0]hexane-2,3-diol (46). MS: 339.1 $(M+H)^+$. $^1$H NMR: 400 MHz DMSO-$d_6$ δ (ppm) 8.12 (s, 1H), 6.75 (t, J=5.8 Hz, 1H), 6.39 (s, 1H), 5.07 (d, J=4.4 Hz, 1H), 4.76 (s, 1H), 4.62-4.57 (m, 1H), 4.48 (d, J=7.2 Hz, 1H), 3.72 (t, J=5.4 Hz, 1H), 3.37 (t, J=6.6 Hz, 2H), 1.82-1.81 (m, 1H), 1.57-1.53 (m, 1H), 1.48-1.44 (m, 1H), 1.19-1.12 (m, 4H), 0.91-0.87 (m, 2H), 0.78-0.74 (m, 2H), 0.63-0.59 (m, 1H);

Compound 16.1 gave (1R,2R,3S,4R,5S)-4-(7-((2,2-difluoroethyl)amino)-5-methyl-3H-imidazo[4,5-b]pyridin-3-yl)bicyclo[3.1.0]hexane-2,3-diol (47). MS: 325.0 $(M+H)^+$. $^1$H NMR: 400 MHz DMSO-$d_6$ δ (ppm) 8.06 (s, 1H), 6.93-6.82 (m, 1H), 6.37 (s, 1H), 6.32-6.01 (m, 1H), 5.04 (d, J=4.4 Hz, 1H), 4.81 (s, 1H), 4.67-4.61 (m, 1H), 4.50 (d, J=7.3 Hz, 1H), 3.99-3.86 (m, 2H), 3.74-3.71 (m, 1H), 2.39 (s, 3H), 1.83-1.79 (m, 1H), 1.49-1.40 (m, 1H), 1.13-1.10 (m, 1H), 0.63-0.55 (m, 1H);

Compound 16.2 gave (1R,2R,3S,4R,5S)-4-(7-((2-fluoroethyl)amino)-5-methyl-3H-imidazo[4,5-b]pyridin-3-yl)bicyclo[3.1.0]hexane-2,3-diol (48). MS: 307.1 $(M+H)^+$. $^1H$ NMR: 400 MHz DMSO-$d_6$ δ (ppm) 8.03 (s, 1H), 6.75 (t, J=6.0 Hz, 1H), 6.30 (s, 1H), 5.06 (d, J=4.4 Hz, 1H), 4.81 (s, 1H), 4.67-4.64 (m, 2H), 4.55-4.51 (m, 2H), 3.78-3.70 (m, 3H), 2.40 (s, 3H), 1.84-1.80 (m, 1H), 1.46-1.44 (m, 1H), 1.14-1.10 (m, 1H), 0.61-0.59 (m, 1H);

Compound 16.3 gave (1R,2R,3S,4R,5S)-4-(7-(ethylamino)-5-methyl-3H-imidazo[4,5-b]pyridin-3-yl)bicyclo[3.1.0]hexane-2,3-diol (49). MS: 289.0 $(M+H)^+$. $^1H$ NMR: 400 MHz DMSO-$d_6$ δ (ppm) 7.99 (s, 1H), 6.52 (t, J=5.6 Hz, 1H), 6.20 (s, 1H), 5.04 (d, J=4.4 Hz, 1H), 4.80 (s, 1H), 4.67-4.60 (m, 11H), 4.50 (d, J=7.2 Hz, 1H), 3.73 (t, J=5.2 Hz, 1H), 3.41-3.34 (m, 2H), 2.39 (s, 3H), 1.83-1.79 (m, 1H), 1.47-1.40 (m, 1H), 1.18 (t, J=7.2 Hz, 3H), 1.12-1.09 (m, 1H), 0.63-0.55 (m, 1H);

Compound 16.4 gave (1R,2R,3S,4R,5S)-4-(7-((2,5-difluorobenzyl)amino)-5-methyl-3H-imidazo[4,5-b]pyridin-3-yl)bicyclo[3.1.0]hexane-2,3-diol (50). MS: 387.1 $(M+H)^+$. $^1H$ NMR: 400 MHz DMSO-$d_6$ δ (ppm) 8.05 (s, 1H), 7.28-7.23 (m, 2H), 7.14-7.11 (m, 2H), 6.21 (s, 1H), 5.03 (d, J=4.4 Hz, 1H), 4.80 (s, 1H), 4.68-4.62 (m, 3H), 4.50 (d, J=7.6 Hz, 1H), 3.74 (t, J=4.8 Hz, 1H), 2.35 (s, 3H), 1.83-1.80 (m, 1H), 1.46-1.44 (m, 1H), 1.13-1.10 (m, 1H), 0.60-0.58 (m, 1H);

Compound 18.1 gave (1R,2R,3S,4R,5S)-4-(7-((2,5-difluorobenzyl)amino)-3H-imidazo[4,5-b]pyridin-3-yl)bicyclo[3.1.0]hexane-2,3-diol (51). MS: 373.0 $(M+H)^+$. $^1H$ NMR: 400 MHz DMSO-$d_6$ δ (ppm) 8.15 (s, 1H), 7.89 (d, J=5.6 Hz, 1H), 7.37 (t, J=6.4 Hz, 1H), 7.29-7.23 (m, 1H), 7.17-7.08 (m, 2H), 6.31 (d, J=5.6 Hz, 1H), 5.07 (d, J=4.4 Hz, 1H), 4.79 (d, J=0.8 Hz, 1H), 4.69 (d, J=6.0 Hz, 2H), 4.63-4.57 (m, 1H), 4.48 (d, J=7.3 Hz, 1H), 3.78 (t, J=5.4 Hz, 1H), 1.84-1.80 (m, 1H), 1.55-1.46 (m, 1H), 1.14-1.10 (m, 1H), 0.65-0.57 (m, 1H);

Compound 23 gave (1S,2R,3S,4R,5S)-4-(2-chloro-6-((2,2-difluoroethyl)amino)-9H-purin-9-yl)-1-(fluoromethyl)bicyclo[3.1.0]hexane-2,3-diol (52). MS: 378.0 $(M+H)^+$. $^1H$ NMR: 400 MHz DMSO-$d_6$ δ (ppm) 8.62 (s, 1H), 8.13 (s, 1H), 6.19 (t, J=55.8 Hz, 1H), 5.36 (d, J=7.2 Hz, 1H), 4.91-4.76 (m, 2H), 4.69 (s, 1H), 4.58 (t, J=6 Hz, 1H), 4.49-4.34 (m, 1H), 3.89-3.85 (m, 3H), 1.71-1.68 (m, 1H), 1.51-1.47 (m, 1H), 0.83-0.79 (m, 1H);

Compound 26.1 gave (1S,2R,3S,4R,5S)-4-(2-chloro-6-(ethylamino)-9H-purin-9-yl)-1-(difluoromethyl)bicyclo[3.1.0]hexane-2,3-diol (53). MS: 360.0 $(M+H)^+$. $^1H$ NMR: 400 MHz DMSO-$d_6$ δ (ppm) 8.31 (s, 1H), 8.05 (s, 1H), 6.38-6.09 (m, 1H), 5.46 (s, 1H), 4.86 (d, J=7.2 Hz, 1H), 4.73 (t, J=6.4 Hz, 1H), 4.62 (s, 1H), 3.97 (s, 1H), 3.45 (t, J=6.4 Hz, 2H), 1.81-1.78 (m, 1H), 1.49 (s, 1H), 1.16 (t, J=7.0 Hz, 3H), 1.07-1.05 (m, 1H). $^1H$ NMR: 400 MHz MeOD δ (ppm) 8.00 (s, 1H), 6.36-6.07 (m, 1H), 4.88 (d, J=6.8 Hz, 1H), 4.78 (s, 1H), 4.02 (d, t=6.8 Hz, 1H), 3.59 (s, 2H), 1.92-1.89 (m, 1H), 1.68 (s, 1H), 1.28 (t, J=14.8 Hz, 3H), 1.17-1.15 (m, 1H);

Compound 26.2 gave (1S,2R,3S,4R,5S)-4-(5-chloro-7-(ethylamino)-3H-imidazo[4,5-b]pyridin-3-yl)-1-(difluoromethyl)bicyclo[3.1.0]hexane-2,3-diol (54). MS: 359.0 $(M+H)^+$. $^1H$ NMR: 400 MHz DMSO-$d_6$ δ (ppm) 8.01 (s, 1H), 7.18 (t, J=6.0 Hz, 1H), 6.39-6.10 (m, 2H), 5.43 (d, J=5.2 Hz, 1H), 4.85-4.83 (m, 1H), 4.77-4.73 (m, 1H), 4.68 (s, 1H), 3.94 (t, J=5.2 Hz, 1H), 3.40 (s, 2H), 1.78-1.75 (m, 1H), 1.52-1.51 (m, 1H), 1.18 (t, J=7.2 Hz, 3H), 1.07-1.04 (m, 1H);

Compound 11.3 gave (1S,2R,3S,4R,5S)-4-(5-(cyclopropylethynyl)-7-(ethylamino)-3H-imidazo[4,5-b]pyridin-3-yl)-1-(difluoromethyl)bicyclo[3.1.0]hexane-2,3-diol (55). MS: 389.0 $(M+H)^+$. $^1H$ NMR: 400 MHz DMSO-$d_6$ δ (ppm) 8.00 (s, 1H), 6.81 (s, 1H), 6.44-6.11 (m, 2H), 5.42 (d, 0.1=4.8 Hz, 1H), 4.84-4.80 (m, 1H), 4.77-4.71 (m, 2H), 3.89 (s, 1H), 3.42-3.36 (m, 2H), 1.78-1.70 (m, 1H), 1.59-1.50 (m, 2H), 1.16 (t, J=7.2 Hz, 3H), 1.07-1.01 (m, 1H), 0.93-0.87 (m, 2H), 0.79-0.72 (m, 2H);

Compound 34 gave (1R,2R,3S,4R,5S)-4-(2-chloro-6-((2,2-difluoroethyl)amino)-9H-purin-9-yl)-1-methylbicyclo[3.1.0]hexane-2,3-diol (56). MS: 360.0 $(M+H)^+$. $^1H$ NMR: 400 MHz DMSO-$d_6$ δ(ppm) 8.59 (s, 1H), 8.12 (s, 1H), 6.32-6.04 (m, 1H), 5.11 (d, J=4.0 Hz, 1H), 4.64 (s, 1H), 4.50 (d, J=8.0 Hz, 1H), 4.40 (t, J=7.2 Hz, 1H), 3.87-3.75 (m, 3H), 1.34 (s, 3H), 1.29-1.26 (m, 1H), 1.23-1.21 (m, 1H), 0.46-0.43 (m, 1H);

Compound 7.4 gave (1R,2R,3S,4R,5S)-4-(2-chloro-6-(methyl-$d_3$-amino)-9H-purin-9-yl)bicyclo[3.1.0]hexane-2,3-diol (57). MS 299 $(M+H)^+$. $^1H$ NMR: 400 MHz DMSO $d_6$ δ 8.18 (s, 1H), 7.99 (b, 1H), 4.63-4.58 (m, 3H). 5.25 (d, J=5.2 Hz, 1H), 5.1 (t, J=5.2 Hz, 1H), 1.84-1.80 (m, 1H), 1.51. 1.49 (m, 1H), 1.12-1.09 (m, 1H), 0.625-0.61 (m, 1H).

Compound 9.7 gave (1R,2R,3S,4R,5S)-4-(5-chloro-7-((5-chloro-2-((3-methylisoxazol-5-yl)methoxy)benzyl)amino)-3H-imidazo[4,5-b]pyridin-3-yl)bicyclo[3.1.0]hexane-2,3-diol (BIO-0461) (75). LCMS: MS: 516.1 $(M+H)^+$. $^1H$ NMR: 400 MHz DMSO-$d_6$ δ(ppm) 8.17 (s, 1H), 7.72-7.66 (m, 1H), 7.32-7.29 (m, 1H), 7.23-7.18 (m, 2H), 6.51 (s, 11H), 6.26 (s, 1H), 5.35 (s, 2H), 5.08 (d, 0.1=4.4 Hz, 1H), 4.70 (s, 1H), 4.63-4.59 (m, 3H), 4.52 (d, J=6.8 Hz, 1H), 3.78-3.75 (m, 1H), 2.24 (s, 3H), 1.84-1.80 (m, 1H), 1.50-1.48 (m, 1H), 1.13-1.10 (m, 1H), 0.62-0.60 (m, 1H)

Compound 9.8 gave (1R,2R,3S,4R,5S)-4-(5-chloro-7-(((6-methoxypyridin-2-yl)methyl)amino)-3H-imidazo[4,5-b]pyridin-3-yl)bicyclo[3.1.0]hexane-2,3-diol (88). LCMS: MS: 402.1 $(M+H)^+$. $^1H$ NMR: 400 MHz DMSO-$d_6$. δ (ppm) 8.17 (s, 1H), 7.73 (t, J=6.4 Hz, 1H), 7.64 (t, J=7.6 Hz, 1H), 6.90 (d, J=7.2 Hz, 1H), 6.68 (d, J=8.4 Hz, 1H), 6.41 (s, 1H), 5.09 (d, J=4.4 Hz, 1H), 4.70 (s, 1H), 4.63-4.59 (m, 3H), 4.52 (d, J=6.4 Hz, 1H), 3.85 (s, 3H), 3.77-3.74 (m, 1H), 1.84-1.80 (m, 1H), 1.50-1.48 (m, 1H), 1.13-1.10 (m, 1H), 0.63-0.60 (m, 1H).

Compound 110.1 gave (1R,2R,3S,4R,5S)-4-(5-chloro-7-((2,2-difluoroethyl)amino)-6-fluoro-3H-imidazo[4,5-b]pyridin-3-yl)bicyclo[3.1.0]hexane-2,3-diol (61). 71.5% yield as white solid. LCMS: 363.1 $(M+H)^+$. $^1H$ NMR: 400 MHz DMSO-$d_{6δ}$ $_{(ppm)}$ 8.31 (s, 1H), 7.48-7.40 (m, 1H), 6.39-6.06 (m, 1H), 5.11 (s, 1H), 4.70 (s, 1H), 4.56 (d, J=17.6 Hz, 2H), 4.34 (tt, J=5.6, 14.8 Hz, 2H), 3.76 (d, J=5.6 Hz, 1H), 1.84-1.80 (m, 1H), 1.49 (td, J=4.4, 8.8 Hz, 1H), 1.12 (q, J=4.4 Hz, 1H), 0.62 (dt, J=4.8, 8.4 Hz, 1H).

Compound 103.1 gave (1R,2R,3S,4R,5S)-4-(5-chloro-7-((2,2-difluoroethyl)amino)-6-methyl-3H-imidazo[4,5-b]pyridin-3-yl)bicyclo[3.1.0]hexane-2,3-diol (60). 43.6% yield) as yellow solid. LCMS: 359.1 $(M+H)^+$. $^1H$ NMR: 400 MHz DMSO-$d_6$ δ (ppm) 8.21 (s, 1H), 6.72 (t, J=6.4 Hz, 1H), 6.40-6.07 (m, 1H), 5.10 (d, J=4.4 Hz, 1H), 4.70 (s, 1H), 4.64-4.57 (m, 1H), 4.56-4.51 (m, 1H), 4.40-4.38 (m, 2H), 3.76-3.71 (m, 1H), 2.22 (s, 3H), 1.82-1.79 (m, 1H), 1.54-1.40 (m, 1H), 1.13-1.10 (m, 1H), 0.62-0.59 (m, 1H)

Compound 150.1 gave (1R,2R,3S,4R,5S)-4-(5,6-dichloro-7-(ethylamino)-3H-imidazo[4,5-b]pyridin-3-yl)bicyclo[3.1.0]hexane-2,3-diol (71) (57% yield). LCMS 343.0 $(M+H)^+$. $^1H$ NMR: 400 MHz DMSO-$d_6$ δ (ppm) 8.23 (s, 1H), 6.96 (t, J=6.4 Hz, 1H), 5.10 (d, J=4.4 Hz, 1H), 4.69 (s, 1H), 4.63-4.57 (m, 1H), 4.55-4.51 (m, 1H), 4.11-4.00 (m, 2H), 3.76 (t, J=5.2 Hz, 1H), 1.85-1.78 (m, 1H), 1.51-1.46 (m, 1H), 1.22 (t, J=7.2 Hz, 3H), 1.12-1.10 (m, 1H), 0.63-0.59 (m, 1H).

Compound 9.9 gave ((1R,2R,3S,4R,5S)-4-(5-chloro-7-(propylamino)-3H-imidazo[4,5-b]pyridin-3-yl)bicyclo[3.1.0]hexane-2,3-diol (66). LCMS: 323.1 $(M+H)^+$. $^1H$ NMR: DMSO+$D_2O$ 400 MHz δ (ppm) 8.13 (s, 1H), 7.18-7.16 (m, 1H), 6.35 (s, 1H), 4.69 (s, 1H), 4.60 (t, 0.1=5.6 Hz, 1H), 3.74 (d, 0.1=6.4 Hz, 1H), 3.41 (s, 2H), 1.83-1.82 (m, 1H), 1.62-1.56 (m, 2H), 1.51-1.49 (m, 11H), 1.12-1.11 (m, 1H), 0.92 (t, J=7.6 Hz, 3H), 0.63-0.61 (m, 1H).

Compound 9.10 gave (1R,2R,3S,4R,5S)-4-(5-chloro-7-((cyclobutylmethyl)amino)-3H-imidazo[4,5-b]pyridin-3-yl)bicyclo[3.1.0]hexane-2,3-diol (67). LCMS: 349.2 $(M+H)^+$. $^1H$ NMR: DMSO 400 MHz. δ (ppm) 8.12 (s, 1H), 7.15 (t, J=6.00 Hz, 1H), 6.35 (s, 1H), 5.08 (d, J=4.8 Hz, 1H), 4.69 (s, 1H), 4.63-4.58 (m, 1H), 4.51 (d, J=7.2 Hz, 1H), 3.74 (t, J=5.2 Hz, 1H), 3.43 (s, 2H), 2.52-2.51 (m, 1H), 2.00-1.98 (m, 2H), 1.85-1.82 (m, 3H), 1.80-1.72 (m, 2H), 1.51-1.48 (m, 1H), 1.13-1.11 (m, 1H), 0.62-0.60 (m, 1H).

Compound 9.11 gave (1R,2R,3S,4R,5S)-4-(5-chloro-7-((2,5-dichlorobenzyl)amino)-3H-imidazo[4,5-b]pyridin-3-yl)bicyclo[3.1.0]hexane-2,3-dio. (68) LCMS: 439.1 $(M+H)^+$. $^1H$ NMR: DMSO δ (ppm) 8.20 (s, 1H), 7.80 (t, J=5.6 Hz, 1H), 7.53 (d, J=8.8 Hz, 1H), 7.40-7.35 (m, 2H), 6.33 (s, 1H), 5.09 (d, J=4.4 Hz, 1H), 4.75 (s, 2H), 4.71 (s, 1H), 4.62-4.59 (m, 1H), 4.51 (d, J=7.2 Hz, 1H), 3.77 (t, J=4.8 Hz, 1H), 1.83-1.81 (m, 1H), 1.51-1.49 (m, 1H), 1.13-1.10 (m, 1H), 0.63-0.61 (m, 1H).

Example 12. Preparation of 5,7-dichloro-3-((3aR,3bR,4aS,5R,5aS)-2,2-dimethylhexahydrocyclopropa[3,4]cyclopenta[1,2-d][1,3]dioxol-5-yl)-2-(triisopropylsilyl)-3H-imidazo[4,5-b]pyridine (100)

-continued

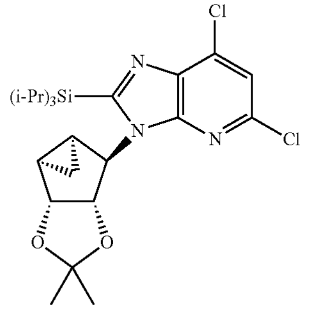

100

To a solution compound 5.3 (1.8 g, 5.29 mmol, 1.0 eq), TIPSCl (1.70 mL, 7.94 mmol, 1.5 eq) and HMPA (9.30 mL, 52.91 mmol, 10 eq) in THF (20 mL) was added LiHMDS (1 M, 13.23 mL, 2.5 eq) dropwise at −70° C. under $N_2$. The mixture was stirred at −70° C. for 3 hrs. TLC (petroleum ether:ethyl acetate=1:1) showed reaction completed. The reaction was quenched by addition sat. $NH_4Cl$ solution (40 mL) and extracted with ethyl acetate (20 mL×3). The combined organic layers were washed with brine (40 mL×1), dried over $Na_2SO_4$, filtered, concentrated and then purified by silica gel chromatography ($SiO_2$, petroleum ether) to give compound 100 (2 g, 4.03 mmol, 76.1% yield) as white solid. LCMS: MS: 496.1 $(M+H)^+$. $^1H$ NMR: 400 MHz DMSO-$d_6$ δ (ppm) 7.61 (s, 1H), 5.45-5.40 (m, 1H), 4.89 (d, J=7.2 Hz, 1H), 4.72 (s, 1H), 1.98-1.94 (m, 1H), 1.64-1.50 (m, 4H), 1.20-1.11 (m, 24H), 0.89-0.81 (m, 1H), 0.71-0.69 (m, 1H).

Example 13. Preparation of 5,7-dichloro-3-((3aR,3bR,4aS,5R,5aS)-2,2-dimethylhexahydrocyclopropa[3,4]cyclopenta[1,2-d][1,3]dioxol-5-yl)-2-(triisopropylsilyl)-3H-imidazo[4,5-b]pyridine-6-carbonitrile (101)

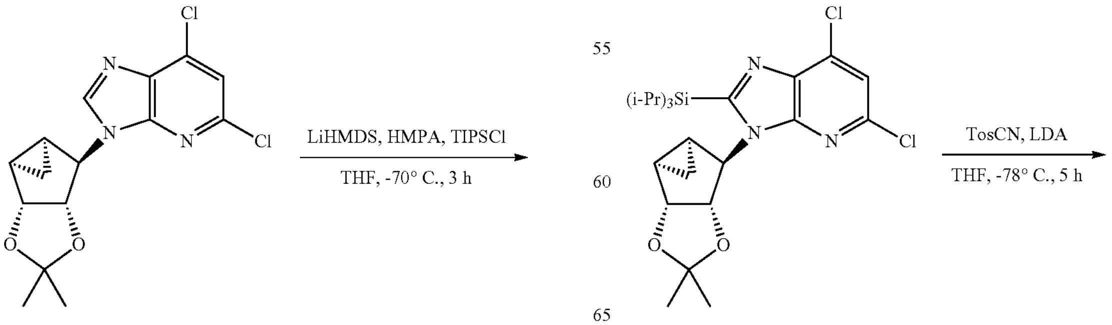

5.3

100

-continued

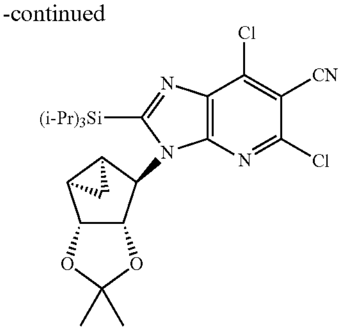

101

To a solution of compound 100 (0.5 g, 1.01 mmol, 1 eq) in THF (10 mL) was added dropwise LDA (2 M, 1.01 mL, 2 eq) at −70° C. under $N_2$. After addition, the mixture was stirred at −70° C. for 0.5 hrs. TosCN (364.9 mg, 2.01 mmol, 2 eq) in THF (10 mL) was added dropwise at −70° C. The resulting mixture was stirred at −70° C. for 2 hrs. LC-MS showed ~7.0% of compound 100 remained. Several new peaks were shown on LC-MS and ~17.2% of desired compound was detected. The reaction mixture was quenched by addition saturated aqueous $NH_4Cl$ (40 mL), and extracted with ethyl acetate (20 mL×3). The combined organic layers were washed with brine (40 mL×3), dried over $Na_2SO_4$, filtered and concentrated under reduced pressure to give a residue. The residue was purified by column chromatography ($SiO_2$, Petroleum ether/Ethyl acetate=10/1, 8/1 to 0/1) to obtain compound 101 (0.23 g, 440.99 umol, 43.79% yield) as a white solid. LCMS: 521.1 $(M+H)^+$. $^1H$ NMR: 400 MHz DMSO-$d_6$ δ (ppm) 5.37 (t, J=6.4 Hz, 11H), 4.91 (d, J=7.2 Hz, 11H), 4.72 (s, 1H), 2.01-1.99 (m, 11H), 1.69-1.68 (m, 1H), 1.59-1.55 (m, 3H), 1.43 (s, 3H), 1.18-1.14 (m, 18H), 0.98 (s, 3H), 0.91-0.89 (m, 1H), 0.72-0.71 (m, 1H).

Similarly prepared according to the method of Example 13 were the following compounds:

Substituting TosCN for NFSI gave 5,7-dichloro-3-((3aR,3bR,4aS,5R,5aS)-2,2-dimethylhexahydrocyclopropa[3,4]cyclopenta[1,2-d][1,3]dioxol-5-yl)-6-fluoro-2-(triisopropylsilyl)-3H-imidazo[4,5-b]pyridine (101.1)

Substituting TosCN for

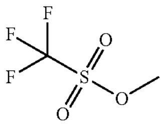

gave 5,7-dichloro-3-((3aR,3bR,4aS,5R,5aS)-2,2-dimethylhexahydrocyclopropa[3,4]cyclopenta[1,2-d][1,3]dioxol-5-yl)-6-methyl-2-(triisopropylsilyl)-3H-imidazo[4,5-b]pyridine (102.1). LCMS: 510.2 $(M+H)^+$. $^1H$ NMR: 400 MHz DMSO-$d_6$ δ (ppm) 5.44-5.43 (m, 1H), 4.86 (d, J=6.8 Hz, 1H), 4.71 (s, 1H), 1.98-1.93 (m, 1H), 1.59-1.56 (m, 4H), 1.43 (s, 3H), 1.19-1.10 (m, 24H), 0.86-0.84 (m, 1H), 0.70-0.73 (m, 1H).

Substituting TosCN for $Cl_2Cl_6$ gave 5,6,7-trichloro-3-((3aR,3bR,4aS,5R,5aS)-2,2-dimethylhexahydrocyclopropa[3,4]cyclopenta[1,2-d][1,3]dioxol-5-yl)-2-(triisopropylsilyl)-3H-imidazo[4,5-b]pyridine (104.1) LCMS: 532.1 $(M+H)^+$. $^1H$ NMR: 400 MHz $CDCl_3$ δ (ppm) 5.63-5.58 (m, 1H), 4.82 (t, J=3.2 Hz, 2H), 2.17-2.10 (m, 1H), 1.67-1.59 (m, 3H), 1.56-1.53 (m, 3H), 1.53-1.45 (m, 1H), 1.23-1.17 (m, 21H), 0.95-0.83 (m, 2H).

101.1

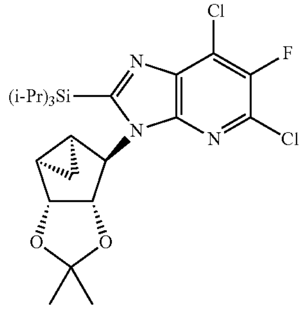

102.1

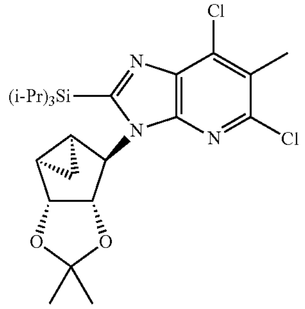

104.1

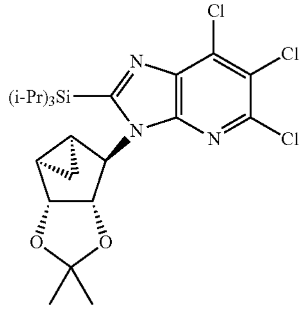

Example 14. Preparation of 5-chloro-3-((3aR,3bR,4aS,5R,5aS)-2,2-dimethylhexahydrocyclopropa[3,4]cyclopenta[1,2-d][1,3]dioxol-5-yl)-7-(ethylamino)-3H-imidazo[4,5-b]pyridine-6-carbonitrile (102)

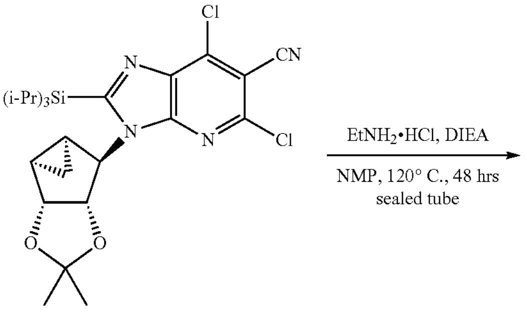

101

-continued

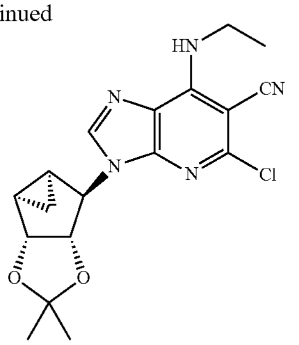

102

To a solution of compound 101 (0.2 g, 383.47 umol, 1 eq) in NMP (5 mL) was added dropwise DIEA (1.92 mmol, 0.35 mL, 5 eq) and $EtNH_2 \cdot HCl$ (156.3 mg, 1.92 mmol, 5 eq) under $N_2$. The resulting mixture was stirred at 130° C. for 16 hrs. LC-MS showed ~0% of compound 101 remained. Several new peaks were shown on LC-MS and ~14.9% of desired compound was detected. The reaction mixture was quenched by addition water (15 mL), and extracted with ethyl acetate (20 mL×3). The combined organic layers were washed with brine (40 mL×3), dried over $Na_2SO_4$, filtered and concentrated under reduced pressure to give compound 102 (0.2 g, crude) as white solid. LCMS: MS: 374.1 (M+H).

Example 15. Preparation of 5-chloro-3-((1S,2R,3S,4R,5R)-3,4-dihydroxybicyclo[3.1.0]hexan-2-yl)-7-(ethylamino)-3H-imidazo[4,5-b]pyridine-6-carbonitrile (93)

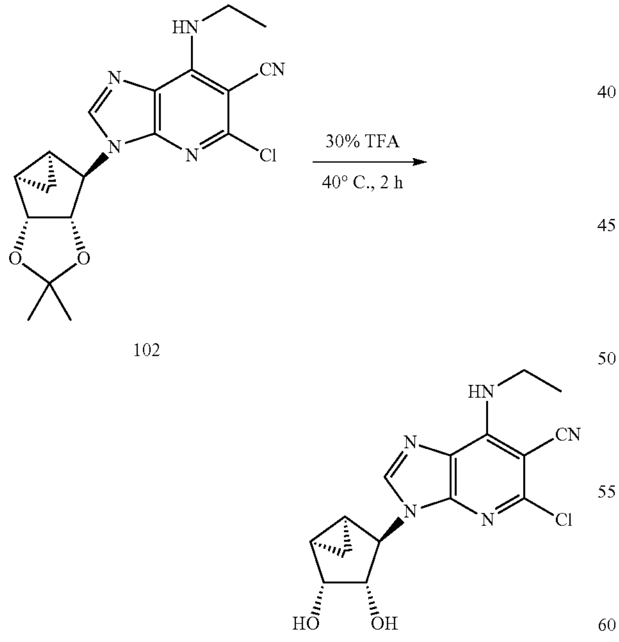

102

93

To a solution of compound 102 (0.20 g, 534.99 umol, 1 eq) was added dropwise TFA (60.78 mmol, 15.0 mL, 30% purity, 113.6 eq) at 20° C. After addition, the mixture was stirred at 40° C. for 2 hrs. LC-MS showed ~0% of compound 102 remained. Several new peaks were shown on LC-MS and ~97.8% of desired compound was detected. The reaction mixture was concentrated under reduced pressure to remove solvent. The crude product was purified by prep-HPLC (column: Phenomenex C18 75*30 mm*3 um; mobile phase: [water ($NH_3H_2O$+$NH_4HCO_3$)-ACN]; B %: 10%-40%, 8 min) to obtain BIO-0458 (52.0 mg, 155.79 umol, 29.1% yield) as white solid. LCMS: MS: 334.0 $(M+H)^+$. $^1H$ NMR: DMSO 400 MHz δ(ppm) 8.32 (s, 1H), 7.72 (t, J=6.0 Hz, 1H), 5.13 (d, J=4.4 Hz 1H), 4.70 (s, 1H), 4.60-4.54 (m, 2H), 4.03-3.98 (m, 2H), 3.78-3.76 (m, 1H), 1.83-1.81 (m, 1H), 1.51-1.48 (m, 1H), 1.24-1.20 (m, 3H), 1.12-1.11 (m, 1H), 0.64-0.61 (m, 1H).

Example 16. Preparation of 5-chloro-N-(2,2-difluoroethyl)-3-((3aR,3bR,4aS,5R,5aS)-2,2-dimethylhexahydrocyclopropa[3,4]cyclopenta[1,2-d][1,3]dioxol-5-yl)-6-fluoro-3H-imidazo[4,5-b]pyridin-7-amine (110.1)

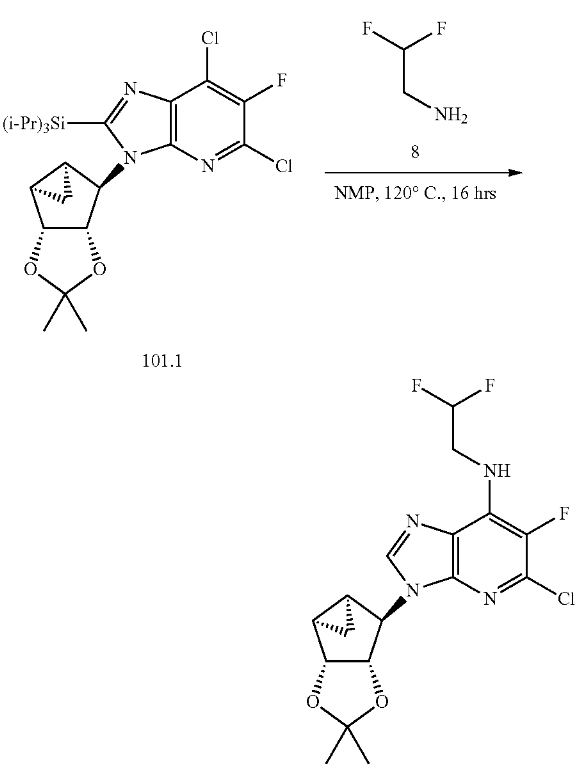

101.1

8

110.1

The mixture of compound 101.1 (300 mg, 583.1 umol, 1.0 eq) and compound 8 (472.6 mg, 5.83 mmol, 10 eq) in NMP (2 mL) were stirred at 120° C. for 40 hrs. LCMS showed reaction completed. The reaction mixture was partitioned between ethyl acetate (15 mL×3). The combined organic layers were washed with brine (20 mL×3), dried over $Na_2SO_4$, filtered, concentrated and then purified by Pre-TLC (petroleum ether:ethyl acetate=2:1) to give compound 110.1 (130 mg, 322.7 umol, 55.3% yield) as yellow solid. LCMS: 403.0 $(M+H)^+$. $^1H$ NMR: 400 MHz DMSO-$d_6$ δ (ppm) 8.36 (s, 1H), 7.48-7.45 (m, 1H), 6.38-6.06 (m, 1H), 5.27-5.22 (m, 1H), 4.92 (s, 1H), 4.58 (d, J=7.2 Hz, 1H), 4.34-4.30 (m, 2H), 2.00-1.94 (m, 1H), 1.75-1.69 (m, 1H), 1.44 (s, 3H), 1.16 (s, 3H), 0.88-0.76 (m, 2H).

Similarly prepared according to the method of Example 16 were the following compounds:

Substituting 101.1 for 102.1 gave 5-chloro-N-(2,2-difluoroethyl)-3-((3aR,3bR,4aS,5R,5aS)-2,2-dimethylhexahydrocyclopropa[3,4]cyclopenta[1,2-d][1,3]dioxol-5-yl)-6-methyl-3H-imidazo[4,5-b]pyridin-7-amine (103.1). 42.6% yield as yellow solid. LCMS: 399.1 $(M+H)^+$. $^1H$ NMR: 400 MHz DMSO-$d_6$ δ (ppm) 8.25 (s, 1H), 6.74 (t, J=6.5 Hz, 1H), 6.38-6.07 (m, 1H), 5.29-5.23 (m, 1H), 4.90 (s, 1H), 4.56 (d, J=6.8 Hz, 1H), 4.49-4.32 (m, 2H), 2.22 (s, 3H), 1.98-1.90 (m, 1H), 1.70-1.68 (m, 1H), 1.44 (s, 3H), 1.16 (s, 3H), 0.88-0.76 (m, 2H).

Substituting 101.1 for 104.1 and adding HCl gave 5,6-dichloro-3-((3aR,3bR,4aS,5R,5aS)-2,2-dimethylhexahydrocyclopropa[3,4]cyclopenta[1,2-d][1,3]dioxol-5-yl)-N-ethyl-3H-imidazo[4,5-b]pyridin-7-amine (150.1). LCMS: 383.1 $(M+H)^+$. $^1H$ NMR: 400 MHz DMSO-$d_6$ δ (ppm) 7.81 (s, 1H), 5.41-5.30 (m, 1H), 5.25 (t, J=5.6 Hz, 1H), 5.01 (s, 1H), 4.65 (d, J=7.2 Hz, 1H), 4.25-4.07 (m, 2H), 2.09-2.07 (m, 1H), 1.72-1.64 (m, 1H), 1.55 (s, 3H), 1.37 (t, J=7.2 Hz, 3H), 1.24 (s, 3H), 1.00-0.86 (m, 2H).

103.1

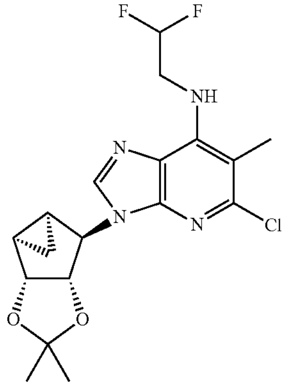

150.1

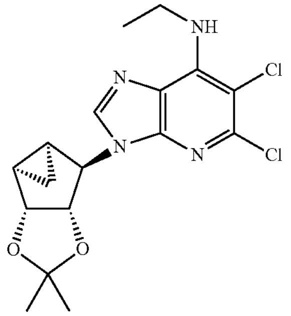

Example 17. Preparation of 5,7-dichloro-3-((3aR,3bR,4aS,5R,5aS)-2,2-dimethylhexahydrocyclopropa[3,4]cyclopenta[1,2-d][1,3]dioxol-5-yl)-2-(triisopropylsilyl)-3H-imidazo[4,5-b]pyridine-6-carbaldehyde (110)

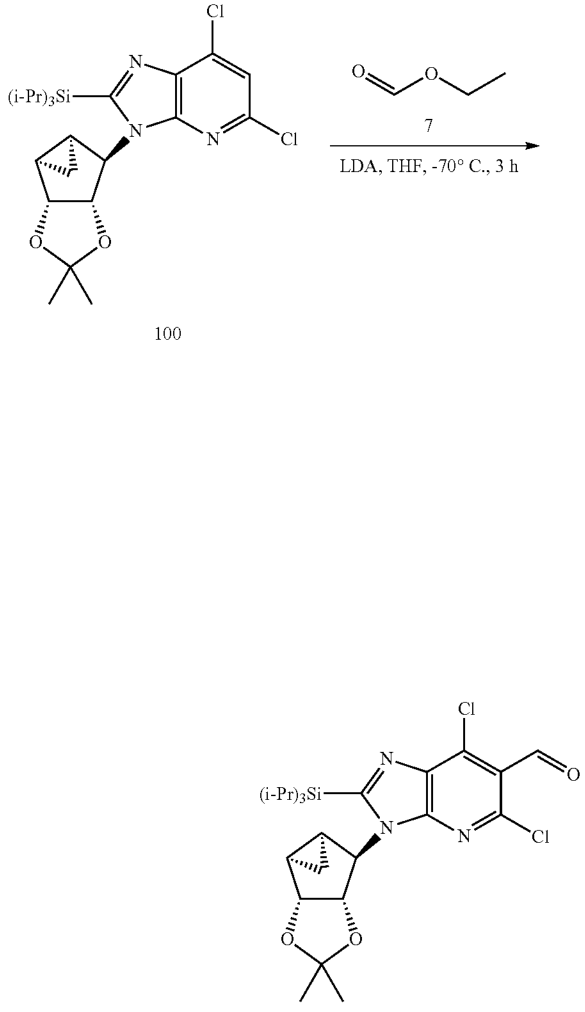

100

110

To a solution of compound 100 (500 mg, 1.01 mmol, 1.0 eq) in THF (8 mL) was added LDA (2 M, 1.01 mL, 2.0 eq) dropwise at −78° C. under $N_2$ and stirred for 30 min. Compound 7 (373.0 mg, 5.03 mmol, 5.0 eq) in THF (1 mL) was added dropwise and stirred at −78° C. for 1 hr. TLC (petroleum ether:ethyl acetate=20:1) showed reaction completed. The reaction mixture was quenched by addition sat.$NH_4Cl$ solution (20 mL) at 20° C., and then extracted with ethyl acetate (15 mL×3). The combined organic layers were washed with brine (20 mL), dried over $Na_2SO_4$, filtered, concentrated and then purified by Pre-TLC (petroleum ether:ethyl acetate=20:1) to give (470 mg, 896.00 umol, 88.9% yield) of 110 as white solid. LCMS: 524.1 $(M+H)^+$. $^1H$ NMR: 400 MHz $CDCl_3$. δ (ppm) 10.62 (s, 1H), 5.66-5.60 (m, 1H), 4.87-4.80 (m, 2H), 2.18-2.17 (m, 1H), 1.71-1.59 (m, 3H), 1.56-1.54 (m, 3H), 1.53-1.48 (m, 1H), 1.24-1.20 (m, 21H), 0.97-0.84 (m, 2H).

Example 18. Preparation of 5,7-dichloro-3-((3aR,3bR,4aS,5R,5aS)-2,2-dimethylhexahydrocyclopropa[3,4]cyclopenta[1,2-d][1,3]dioxol-5-yl)-2-(triisopropylsilyl)-3H-imidazo[4,5-b]pyridin-6-ol (1H)

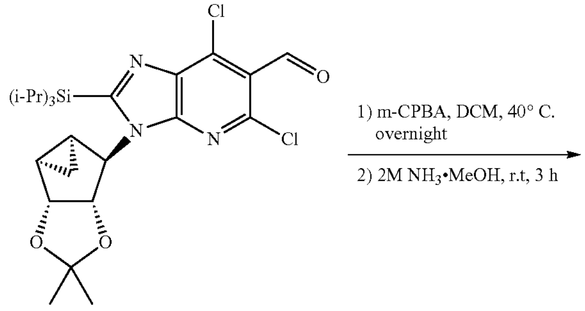

110

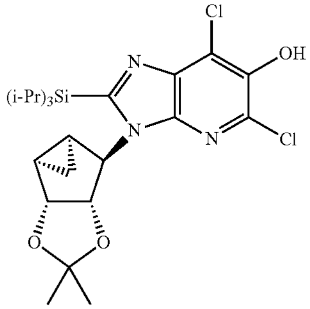

111

To a solution of compound 110 (200 mg, 381.28 umol, 1.0 eq) in DCM (5 mL) was added m-CPBA (77.41 mg, 381.28 umol, 85% purity, 1.0 eq) at 25° C., the reaction mixture was stirred at 40° C. for 20 hrs. LCMS showed compound 110 was consumed. The mixture was cooled to r.t and $NH_3$-MeOH (2M, ~ 2.5 mL, until appearance of clean solution) was added and stirred at the same temperature. LCMS showed desired MS. The reaction mixture was quenched by addition sat. $Na_2SO_3$ (20 mL), and then extracted with DCM (10 mL×3). The combined organic layers were washed with brine (15 mL), dried over $Na_2SO_4$, filtered, concentrated and then purified by Pre-TLC (petroleum ether:ethyl acetate=5:1) to give compound 111 (120 mg, 234.13 umol, 61.4% yield) as white solid. LCMS: 512.2 $(M+H)^+$. $^1H$ NMR: 400 MHz $CDCl_3$ δ (ppm) 5.64-5.58 (m, 1H), 4.85-4.79 (m, 2H), 2.14-2.11 (m, 1H), 1.67-1.60 (m, 4H), 1.54 (s, 3H), 1.53-1.47 (m, 1H), 1.23-1.17 (m, 21H), 0.94-0.82 (m, 2H).

Example 19. Preparation of 5,7-dichloro-6-((3-chlorobenzyl)oxy)-3-((3aR,3bR,4aS,5R,5aS)-2,2-dimethylhexahydrocyclopropa[3,4]cyclopenta[1,2-d][1,3]dioxol-5-yl)-2-(triisopropylsilyl)-3H-imidazo[4,5-b]pyridine (112)

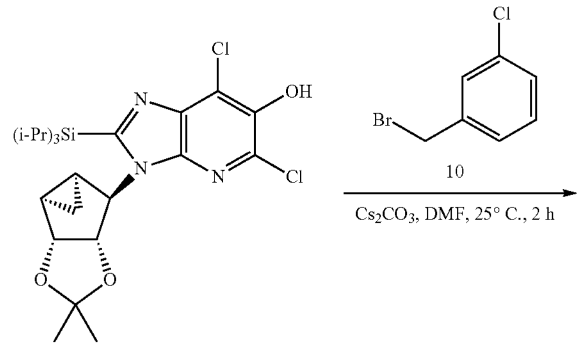

111

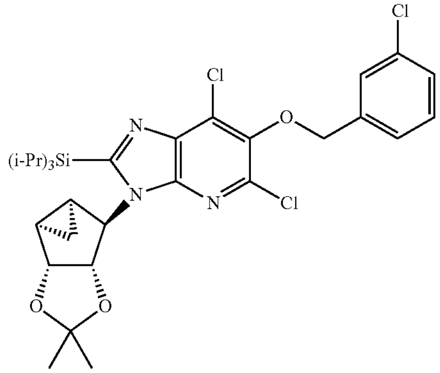

112

To a solution of compound 111 (170 mg, 331.68 umol, 1.0 eq) in DMF (3 mL) was added compound 10 (75.0 mg, 364.85 umol, 1.1 eq) and $Cs_2CO_3$ (216.1 mg, 663.4 umol, 2.0 eq). The mixture was stirred at 25° C. for 2 hrs. TLC (petroleum ether:ethyl acetate=20:1) showed reaction completed. The reaction mixture was partitioned between ethyl acetate (10 mL×3) and water (20 mL). The combined organic layers were washed with brine (15 ml), dried over sodium sulfate, filtered, concentrated and then purified by Pre-TLC (petroleum ether:ethyl acetate=20:1) to give compound 112 (170 mg, 266.83 umol, 80.4% yield) as white solid. LCMS: 638.1 $(M+H)^+$. $^1H$ NMR: 400 MHz $CDCl_3$δ (ppm) 7.63 (s, 1H), 7.54-7.48 (m, 1H), 7.40-7.35 (m, 2H), 5.68-5.59 (m, 1H), 5.04 (s, 2H), 4.90-4.79 (m, 2H), 2.17-2.14 (m, 1H), 1.68-1.61 (m, 3H), 1.55 (s, 3H), 1.53-1.49 (m, 1H), 1.25-1.88 (m, 21H), 0.96-0.82 (m, 2H).

Example 20. Preparation of 5-chloro-6-((3-chlorobenzyl)oxy)-3-((3aR,3bR,4aS,5R,5aS)-2,2-dimethylhexahydrocyclopropa[3,4]cyclopenta[1,2-d][1,3]dioxol-5-yl)-3H-imidazo[4,5-b]pyridin-7-amine (113)

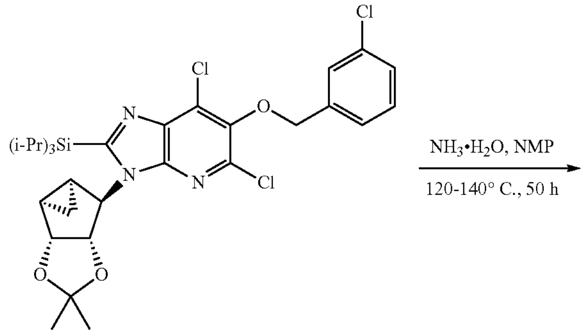

112

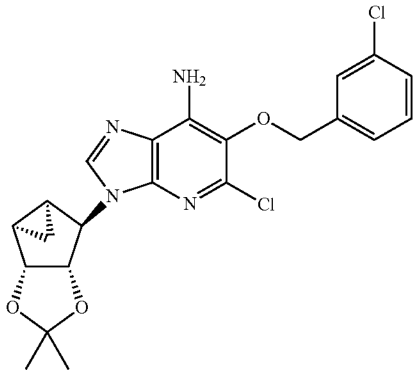

113

To a solution of compound 112 (170 mg, 266.83 umol, 1.0 eq) in NMP (1 mL) was added $NH_3 \cdot H_2O$ (342.58 uL, 2.67 mmol, 30% purity, 10 eq). The mixture was stirred at 140° C. for 50 hrs. LCMS showed reaction completed. The reaction mixture was partitioned between ethyl acetate (10 mL×3). The combined organic layers were washed with brine (20 mL×3), dried over $Na_2SO_4$, filtered, concentrated and then purified by Pre-TLC (petroleum ether:ethyl acetate=1:1) to give compound 113 (30 mg, 65.03 umol, 24.3% yield) as yellow oil. LCMS: 461.1 $(M+H)^+$.

Example 21. Preparation of (1R,2R,3S,4R,5S)-4-(7-amino-5-chloro-6-((3-chlorobenzyl)oxy)-3H-imidazo[4,5-b]pyridin-3-yl)bicyclo[3.1.0]hexane-2,3-diol (92)

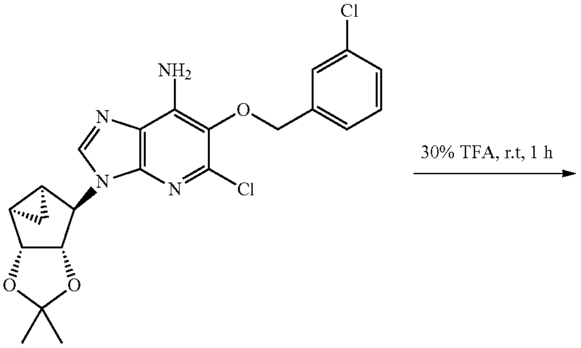

113

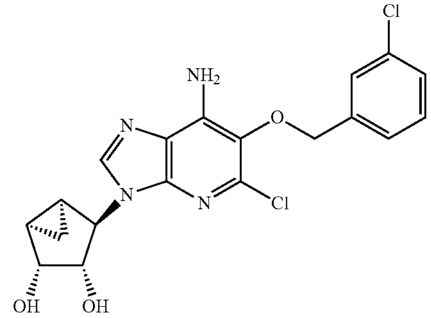

92

Compound 113 (30 mg, 65.03 umol, 1.0 eq) was dissolved in TFA (1 mL, 30% purity) and stirred at 25° C. for 3 hrs. The mixture was concentrated under reduced pressure and purified by Prep-HPLC (column: Phenomenex C18 75×30 mm×3 um; mobile phase: [water ($NH_3H_2O$+$NH_4HCO_3$)-ACN]; B %: 10%-65%, 8 min) to give 92 (4 mg, 9.49 umol, 14.6% yield) as white solid. LCMS: 421.1 $(M+H)^+$. $^1H$ NMR: 400 MHz DMSO-$d_6$ δ (ppm) 8.17 (s, 1H), 7.72 (s, 1H), 7.58-7.51 (m, 1H), 7.49-7.38 (m, 2H), 6.68 (s, 2H), 5.09 (d, J=4.4 Hz, 1H), 4.88 (s, 2H), 4.68 (s, 1H), 4.66-4.57 (m, 1H), 4.51 (d, J=7.2 Hz, 1H), 3.76 (t, J=5.2 Hz, 1H), 1.84-1.81 (m, 1H), 1.53-1.45 (m, 1H), 1.13-1.10 (m, 1H), 0.63-0.60 (m, 1H).

Example 22. Preparation of 5,7-dichloro-3-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-3H-imidazo[4,5-b]pyridine (3)

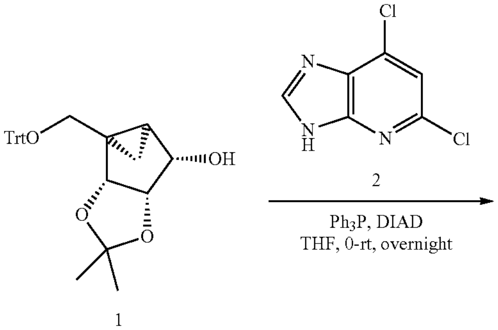

1

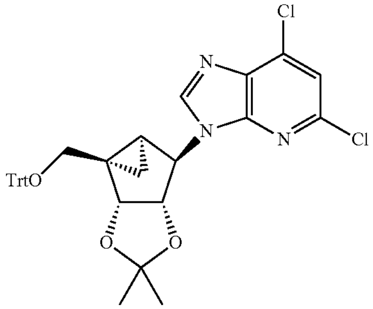

3

To a solution of compound 1 (35.0 g, 79.09 mmol, 1.2 eq) in THF (440 mL) was added $PPh_3$ (34.6 g, 131.91 mmol, 2.0 eq) and DIAD (26.67 g, 131.91 mmol, 25.65 mL, 2.0 eq) under $N_2$. The mixture was stirred at 20° C. for 15 min. Then compound 2 (12.4 g, 65.96 mmol, 1.0 eq) was added into the mixture and stirred at 20° C. for 16 hrs. TLC (Petroleum ether/Ethyl acetate=3/1) showed the reaction completed and LCMS. The reaction mixture was concentrated under reduced pressure to give a residue. The residue was purified by column chromatography ($SiO_2$, Petroleum ether/Ethyl acetate=20/1 to 0/1) to obtain compound 3 (61.0 g, crude) as yellow solid. LCMS: 612.1 $(M+H)^+$. $^1H$ NMR: 400 MHz DMSO-$d_6$ δ (ppm) 8.68 (s, 1H), 7.62 (s, 1H), 7.38-7.24 (m, 15H), 5.24 (d, J=7.2 Hz, 1H), 5.05 (s, 1H), 4.79 (d, J=7.2 Hz, 1H), 3.38-3.28 (m, 2H), 1.75-1.72 (m, 1H), 1.46 (s, 3H), 1.19 (s, 3H), 1.03 (t, J=4.8 Hz, 1H), 0.95-0.93 (m, 1H).

Example 23. Preparation of ((3aR,3bR,4aS,5R,5aS)-5-(5,7-dichloro-3H-imidazo[4,5-b]pyridin-3-yl)-2,2-dimethyltetrahydrocyclopropa[3,4]cyclopenta[1,2-d][1,3]dioxol-3b(3aH)-yl)methanol (4)

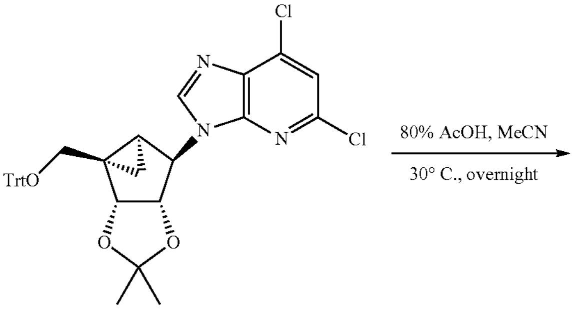

3

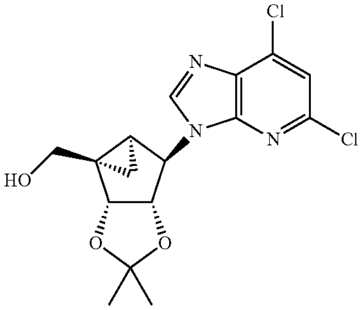

4

To a solution of compound 3 (61.0 g, crude) in ACN (160 mL) was added AcOH (8.53 mol, 610 mL, 80% purity, 85.7 eq) at 30° C. The mixture was stirred at 30° C. for 16 hrs. TLC (petroleum ether:ethyl acetate=1:1) showed reaction completed. The reaction mixture was basified with $NH_3 \cdot H_2O$, adjusted pH=8, then extracted with Ethyl acetate (400 mLx3). The combined organic layers were washed with brine (500 mL), dried over $Na_2SO_4$, filtered and concentrated under reduced pressure to give a residue. The residue was purified by silica gel chromatography ($SiO_2$, petroleum ether:ethyl acetate=5:1 to 1:3) to obtain compound 4 (13.3 g, 35.9 mmol, 36.0% yield) as yellow solid. LCMS: 370.1 $(M+H)^+$. $^1H$ NMR: 400 MHz DMSO-$d_6$ δ (ppm) 8.75 (s, 1H), 7.67 (s, 1H), 5.20 (d, J=7.2 Hz, 1H), 5.01 (s, 1H), 4.95 (t, J=5.2 Hz, $1H_4$), 4.66-4.65 (m, 2H), 3.47-3.43 (m, 1H), 1.72-1.69 (m, 1H), 1.45 (s, 3H), 1.16 (s, 3H), 1.00-0.92 (m, 2H).

Example 24. Preparation of (3aR,3bS,4aS,5R,5aS)-5-(5,7-dichloro-3H-imidazo[4,5-b]pyridin-3-yl)-2,2-dimethyltetrahydrocyclopropa[3,4]cyclopenta[1,2-d][1,3]dioxole-3b(3aH)-carbaldehyde (5)

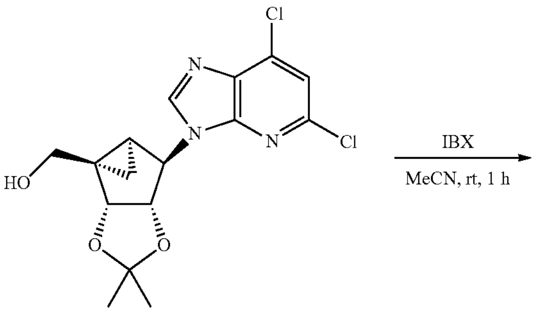

4

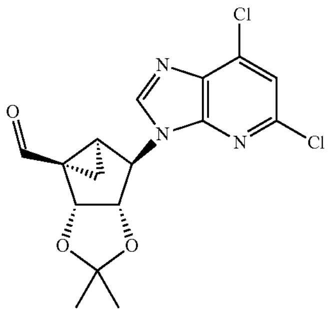

5

To a solution of compound 4 (11.3 g, 30.52 mmol, 1.0 eq) in ACN (115 mL) was added IBX (11.1 g, 39.68 mmol, 1.3 eq) at 20° C. The mixture was stirred at 80° C. for 1 hr. TLC (petroleum ether:ethyl acetate=1:1) showed reaction completed. Solid was removed by filtration and the filtrates were used directly for the next step.

Example 25. Preparation of (3aR,3bS,4aS,5R,5aS)-5-(5,7-dichloro-3H-imidazo[4,5-b]pyridin-3-yl)-2,2-dimethyltetrahydrocyclopropa[3,4]cyclopenta[1,2-d][1,3]dioxole-3b(3aH)-carboxylic acid (6)

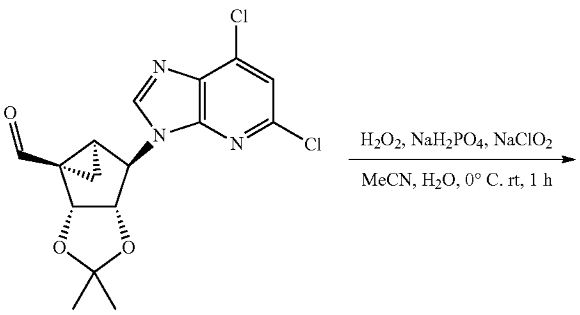

5

-continued

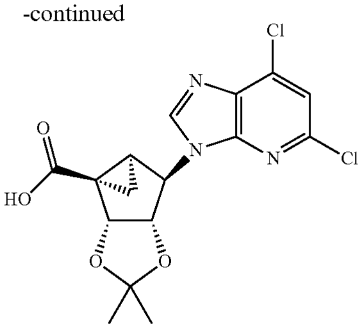

6

To a solution of compound 5 (11.24 mg, 20.53 mmol, 1.0 eq) in MeCN (above step) was added $NaH_2PO_4$ (7.32 g, 61.05 mmol, 2.0 eq) in $H_2O$ (23 mL) and $H_2O_2$ (3.46 g, 30.53 mmol, 30% purity, 1.0 eq) at 20° C. Then added a solution of $NaClO_2$ (3.31 g, 36.63 mmol, 80% purity, 1.2 eq) in $H_2O$ (30 mL) at 0° C. The mixture was stirred at 20° C. for 1 hr. TLC (petroleum ether:ethyl acetate=1:1) showed reaction completed. The reaction mixture was quenched by addition saturated aqueous $Na_2S_2O_3$ (500 mL) at 0° C., and extracted with ethyl acetate (150 mL×3). The combined organic layers were washed with brine (200 mL), dried over $Na_2SO_4$, filtered and concentrated under reduced pressure to obtain compound 6 (11.3 g, crude) as yellow solid. LCMS: 384.0 $(M+H)^+$. $^1H$ NMR: 400 MHz DMSO-$d_6$ δ (ppm) 8.58 (s, 1H), 7.63 (s, 1H), 5.68 (d, J=7.2 Hz, 1H), 5.09 (s, 1H), 4.83 (d, J=6.8 Hz, 1H), 2.24-2.22 (m, 1H), 1.56-1.54 (m, 1H), 1.46 (s, 3H), 1.35-1.32 (m, 1H), 1.19 (s, 3H).

Example 26. Preparation of (3aR,3bS,4aS,5R,5aS)-5-(5,7-dichloro-3H-imidazo[4,5-b]pyridin-3-yl)-N,2,2-trimethyltetrahydrocyclopropa[3,4]cyclopenta[1,2-d][1,3]dioxole-3b(3aH)-carboxamide (7)

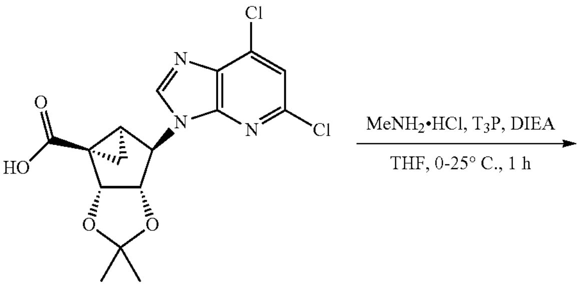

6

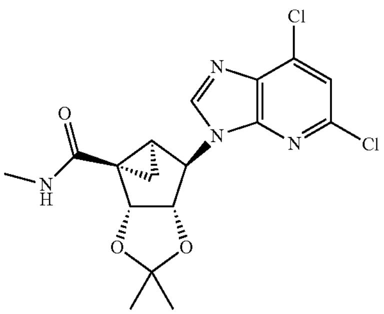

7

To a solution of compound 6 (13.3 g, 34.62 mmol, 1.0 eq) and $MeNH_2$·HCl (2.34 g, 34.62 mmol, 1.0 eq) in THF (240 mL) was added DIEA (20.13 g, 155.77 mmol, 4.5 eq) and $T_3P$ (33.04 g, 51.92 mmol, 50% purity, 1.5 eq) at 0° C. The mixture was stirred at 25° C. for 1 hr. TLC (Dichloromethane:Methanol=10:1) showed reaction completed and desired detected. The reaction mixture was partitioned between ethyl acetate (80 mL×3) and water (300 mL). The organic phase was separated, washed with sat. NaCl (100 mL), dried over $Na_2SO_4$, filtered and concentrated under reduced pressure to give a residue which was purified by silica gel chromatography ($SiO_2$, petroleum ether:ethyl acetate=50:1 to 0:2) to obtain compound 7 (11.7 g, 29.45 mmol, 85.08% yield) as yellow solid. LCMS: 397.0 $(M+H)^+$. $^1$H NMR: 400 MHz DMSO-$d_6$ δ (ppm) 8.57 (s, 1H), 7.78 (d, J=4.4 Hz, 1H), 7.64 (s, 1H), 6.64 (s, 1H), 5.64 (d, J=6.8 Hz, 1H), 5.08 (s, 1H), 4.83 (d, J=6.0 Hz, 1H), 3.16 (d, J=5.2 Hz, 1H), 2.64 (d, J=4.4 Hz, 3H), 1.47 (s, 3H), 1.25-1.20 (m, 4H).

Example 27. Preparation of (3aR,3bS,4aS,5R,5aS)-5-(5-chloro-7-(ethylamino)-3H-imidazo[4,5-b]pyridin-3-yl)-N,2,2-trimethyltetrahydrocyclopropa[3,4]cyclopenta[1,2-d][1,3]dioxole-3b(3aH)-carboxamide (209.1)

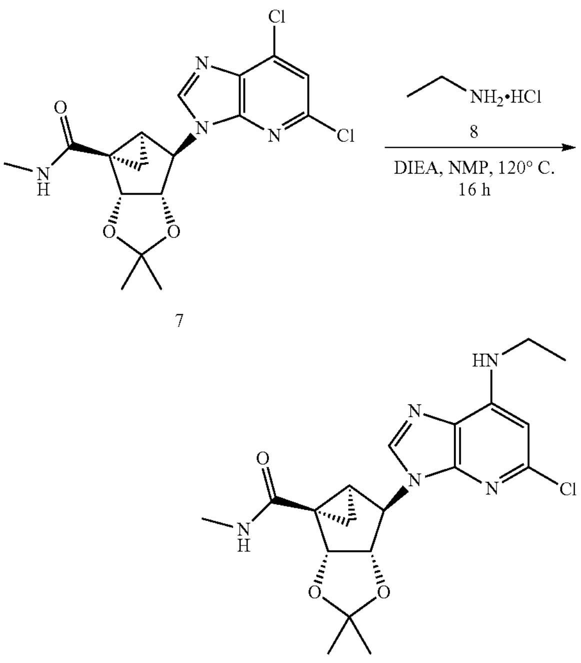

7

209.1

To a solution of compound 7 (11 g, 27.69 mmol, 1.0 eq) in NMP (110 mL) was added DIEA (21.47 g, 166.14 mmol, 6.0 eq) and compound 8 (11.29 g, 138.45 mmol, 5.0 eq) at 20° C. The mixture was stirred at 120° C. for 16 hrs. TLC (ethyl acetate) showed reaction almost completed. The mixture was diluted with $H_2O$ (400 mL) and extracted with ethyl acetate (100 mL×3). The combined organic layers were washed with brine (150 mL×3), dried over $Na_2SO_4$, filtered and concentrated under reduced pressure to give a residue. The residue was purified by column chromatography ($SiO_2$, Petroleum ether:Ethyl acetate=50:1 to 0:1) to obtain compound 209.1 (4.5 g, 11.09 mmol, 40.04% yield) as yellow solid. LCMS: 406.1 $(M+H)^+$. $^1$H NMR: 400 MHz DMSO-$d_6$ δ (ppm) 8.06 (s, 1H), 7.73-7.70 (m, 1H), 7.21 (t, J=6.0 Hz, 1H), 6.35 (s, 1H), 5.62 (d, J=7.2 Hz, 1H), 4.94 (s, 1H), 4.71 (d, J=6.4 Hz, 1H), 3.40 (s, 2H), 2.64 (d, J=4.4 Hz, 3H), 2.07-2.03 (m, 1H), 1.47-1.44 (m, 4H), 1.23-1.15 (m, 7H).

Similarly prepared by the method of example 27 by substituting 8 with (5-chloro-2-((3-methylisoxazol-5-yl)methoxy)phenyl)methanamine to form (3aR,3bS,4aS,5R,5aS)-5-(5-chloro-7-((5-chloro-2-((3-methylisoxazol-5-yl)methoxy)benzyl)amino)-3H-imidazo[4,5-b]pyridin-3-yl)-N,2,2-trimethyltetrahydrocyclopropa[3,4]cyclopenta[1,2-d][1,3]dioxole-3b(3aH)-carboxamide (201.1). LCMS: 613.2 $(M+H)^+$.

Similarly prepared by the method of example 27 by substituting 8 with diethylamino-HCl to form (3aR,3bS,4aS,5R,5aS)-5-(5-chloro-7-(ethylamino)-3H-imidazo[4,5-b]pyridin-3-yl)-N-ethyl-2,2-dimethyltetrahydrocyclopropa[3,4]cyclopenta[1,2-d][1,3]dioxole-3b(3aH)-carboxamide (202.1). LCMS: 420.2 $(M+H)^+$.

Similarly prepared by the method of example 27 by substituting 8 with diethylamino-HCl to form (3aR,3bS,4aS,5R,5aS)-5-(5-chloro-7-((2-hydroxyethyl)amino)-3H-imidazo[4,5-b]pyridin-3-yl)-N,2,2-trimethyltetrahydrocyclopropa[3,4]cyclopenta[1,2-d][1,3]dioxole-3b(3aH)-carboxamide (203.1). LCMS: 422.1 $(M+H)^+$.

Similarly prepared by the method of example 27 by substituting 8 with $NH_3$—$H_2O$ to form (3aR,3bS,4aS,5R,5aS)-5-(7-amino-5-chloro-3H-imidazo[4,5-b]pyridin-3-yl)-N,2,2-trimethyltetrahydrocyclopropa[3,4]cyclopenta[1,2-d][1,3]dioxole-3b(3aH)-carboxamide (204.1). LCMS: 378.1 $(M+H)^+$.

Similarly prepared by the method of example 27 by substituting 8 with cyclobutylmethanamine to form (3aR,3bS,4aS,5R,5aS)-5-(5-chloro-7-((cyclobutylmethyl)amino)-3H-imidazo[4,5-b]pyridin-3-yl)-N,2,2-trimethyltetrahydrocyclopropa[3,4]cyclopenta[1,2-d][1,3]dioxole-3b(3aH)-carboxamide (205.1). LCMS: 446.1 $(M+H)^+$.

Similarly prepared by the method of example 27 by substituting 8 with 2-methylpropan-1-amine to form (3aR,3bS,4aS,5R,5aS)-5-(5-chloro-7-(isobutylamino)-3H-imidazo[4,5-b]pyridin-3-yl)-N,2,2-trimethyltetrahydrocyclopropa[3,4]cyclopenta[1,2-d][1,3]dioxole-3b(3aH)-carboxamide (206.1). LCMS 434.2 $(M+H)^+$.

Similarly prepared by the method of example 27 by substituting 8 with propan-1-amine to form (3aR,3bS,4aS,5R,5aS)-5-(5-chloro-7-(propylamino)-3H-imidazo[4,5-b]pyridin-3-yl)-N,2,2-trimethyltetrahydrocyclopropa[3,4]cyclopenta[1,2-d][1,3]dioxole-3b(3aH)-carboxamide (207.1). LCMS: 420.2 $(M+H)^+$ Similarly prepared by the method of example 27 by substituting 8 with cyclopropylmethanamine to form (3aR,3bS,4aS,5R,5aS)-5-(5-chloro-7-((cyclopropylmethyl)amino)-3H-imidazo[4,5-b]pyridin-3-yl)-N,2,2-trimethyltetrahydrocyclopropa[3,4]cyclopenta[1,2-d][1,3]dioxole-3b(3aH)-carboxamide (208.1). LCMS: 432.2 $(M+H)^+$.

-continued
201.1
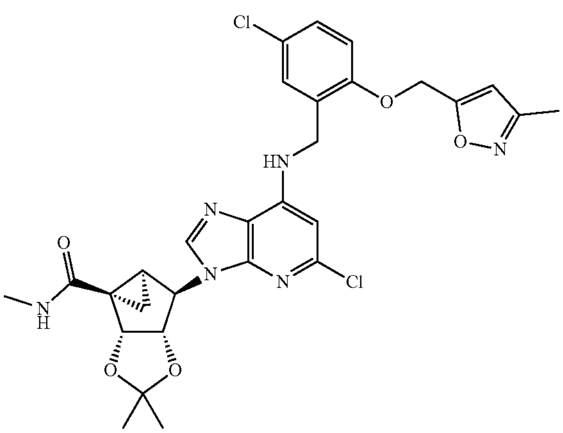
202.1
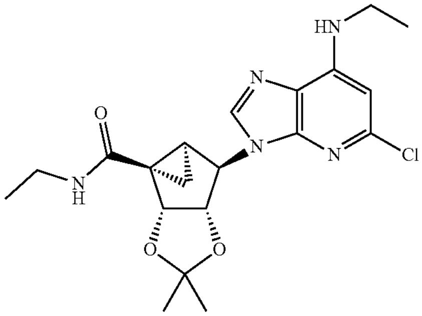
203.1
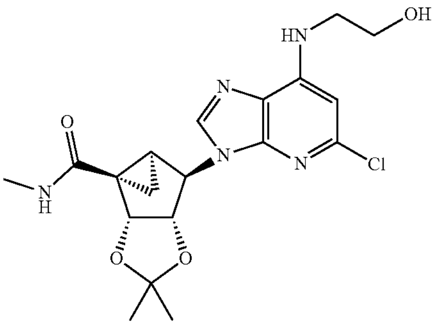
204.1
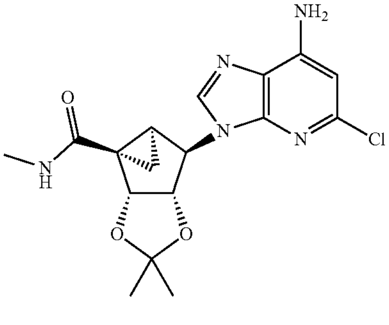
205.1
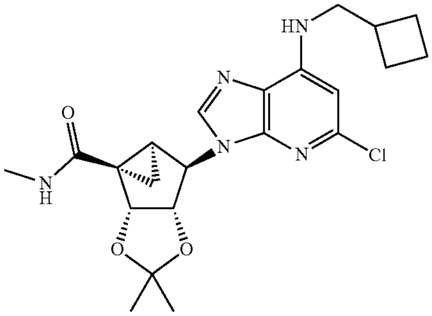
206.1
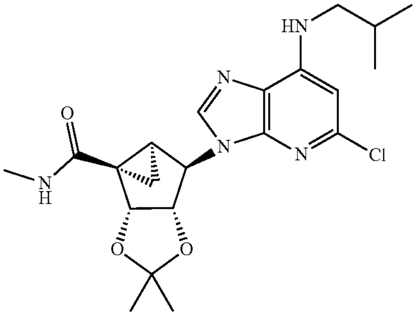
207.1
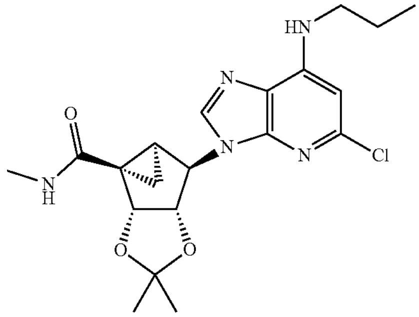
208.1
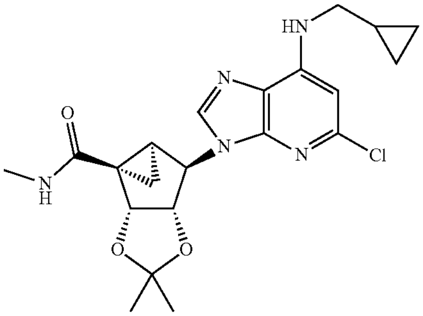
209.1
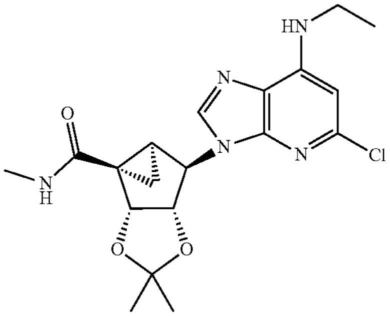

Example 28. Preparation of (3aR,3bS,4aS,5R,5aS)-5-(5-cyano-7-(ethylamino)-3H-imidazo[4,5-b]pyridin-3-yl)-N,2,2-trimethyltetrahydrocyclopropa[3,4]cyclopenta[1,2-d][1,3]dioxole-3b(3aH)-carboxamide (11)

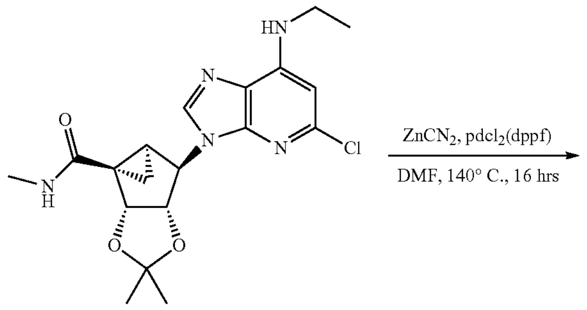

209.1

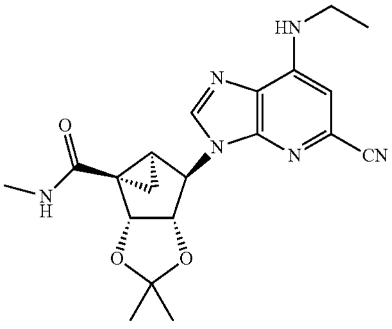

11

A mixture of compound 209.1 (0.1 g, 246.38 umol, 1 eq), $Zn(CN)_2$ (20.3 mg, 172.47 umol, 0.7 eq) and $PdCl_2$ (dppf) (18.0 mg, 24.64 umol, 0.1 eq) in DMF (2 mL) was degassed and purged with $N_2$ for 3 times, and then the mixture was stirred at 130° C. for 16 hrs under $N_2$ atmosphere. Several new peaks were shown on LC-MS and ~19% of desired compound was detected. The reaction mixture was quenched by addition water (10 mL), and extracted with EtOAc (5 mL×3). The combined organic layers were washed with brine (5 mL×3), dried over $Na_2SO_4$, filtered and concentrated under reduced pressure to give a residue. The residue was purified by column chromatography ($SiO_2$, Petroleum ether/Ethyl acetate=5/1, 1/1 to 0/1) to obtain compound 11 (0.162 g) as yellow solid. LCMS: 397.2 $(M+H)^+$. $^1$H NMR: 400 MHz DMSO-$d_6$ δ (ppm) 8.27 (s, 1H), 7.77-7.76 (m, 1H), 7.42 (t, J=6.0 Hz, 1H), 6.91 (s, 1H), 5.62 (d, J=6.8 Hz, 1H), 5.00 (s, 1H), 4.72 (d, J=6.4 Hz, 1H), 3.45-3.44 (m, 2H), 2.65-2.64 (m, 3H), 2.08-2.06 (m, 1H), 1.48-1.46 (m, 4H), 1.24-1.18 (m, 7H).

Example 29. Preparation of (1S,2R,3S,4R,5S)-4-(5-cyano-7-(ethylamino)-3H-imidazo[4,5-b]pyridin-3-yl)-2,3-dihydroxy-N-methylbicyclo[3.1.0]hexane-1-carboxamide (11)

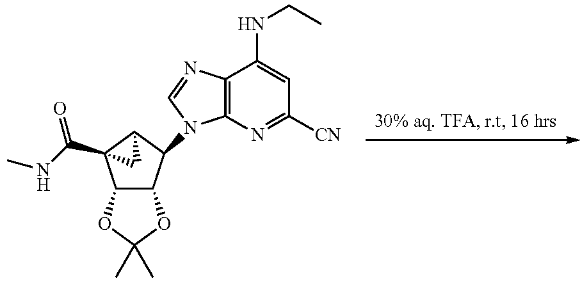

11

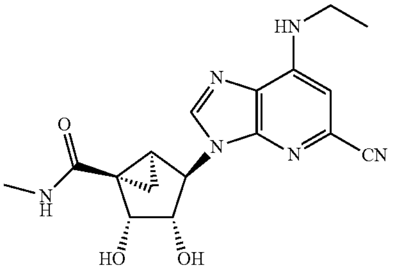

70

A mixture of compound 11 (0.162 g, 408.63 umol, 1 eq) in TFA (81.04 mmol, 20 mL, 30% purity, 198.3 eq) was stirred at 25° C. for 16 hrs. LC-MS showed ~0% of compound 11 remained. Several new peaks were shown on LC-MS and ~58% of desired compound was detected. The mixture was concentrated under reduced pressure to give a residue. The residue was purified by Pre-HPLC (column: Phenomenex C18 75*30 mm*3 um; mobile phase: [water ($NH_3H_2O+NH_4HCO_3$)-CAN]; B %: 5%-35%, 8 min) to obtain 70 (63.77 mg, 178.94 umol, 43.7% yield, 100% purity) as white solid. LCMS: 357.0 $(M+H)^+$. $^1$H NMR: 400 MHz $CDCl_3$ δ (ppm) 8.03 (s, 1H), 6.75-6.74 (m, 1H), 6.71 (s, 1H), 5.63-5.61 (m, 1H), 4.95-4.91 (m, 2H), 4.58-4.56 (m, 1H), 4.14-4.12 (m, 1H), 3.44-3.34 (m, 2H), 3.12-3.10 (m, 1H), 2.95 (d, J=4.8 Hz, 3H), 2.33-2.29 (m, 1H), 1.82-1.79 (m, 1H), 1.40-1.36 (m, 4H).

Similarly prepared by the method of example 29 by substituting 11 with 201.1 to form (1S,2R,3S,4R,5S)-4-(5-chloro-7-((5-chloro-2-((3-methylisoxazol-5-yl)methoxy)benzyl)amino)-3H-imidazo[4,5-b]pyridin-3-yl)-2,3-dihydroxy-N-methylbicyclo[3.1.0]hexane-1-carboxamide. (62). LCMS: 573.1 $(M+H)^+$. $^1$H NMR: 400 MHz DMSO-$d_6$ δ (ppm) 8.05 (s, 1H), 7.69-7.72 (m, 1H), 7.60-7.57 (m, 1H), 7.32-7.29 (m, 1H), 7.22-7.18 (m, 2H), 6.51 (s, 1H), 6.26 (s, 1H), 5.40 (d, J=4.4 Hz, 1H), 5.35 (s, 2H), 4.92 (t, J=6.4 Hz, 1H), 4.80 (d, J=8.0 Hz, 1H), 4.71 (s, 1H), 4.61 (s, 2H), 3.87-3.85 (m, 1H), 2.67 (d, J=4.4 Hz, 3H), 2.34 (s, 3H), 1.81-1.79 (m, 1H), 1.63-1.60 (m, 1H), 1.31-1.29 (m, 1H).

Similarly prepared by the method of example 29 by substituting 11 with 202.1 to form (1S,2R,3S,4R,5S)-4-(5-chloro-7-(ethylamino)-3H-imidazo[4,5-b]pyridin-3-yl)-N-ethyl-2,3-dihydroxybicyclo[3.1.0]hexane-1-carboxamide (69). LCMS: 380.2 $(M+H)^+$. $^1$H NMR: 400 MHz DMSO-$d_6$ δ (ppm) 7.98 (s, 1H), 7.57 (t, J=5.6 Hz, 1H), 7.14 (t, J=6.0 Hz, 1H), 6.34 (s, 1H), 4.93 (d, J=6.0 Hz, 1H), 4.69 (s, 1H), 3.84 (d, J=6.0 Hz, 1H), 3.50-3.48 (m, 2H), 3.38 (s, 2H), 3.18-3.16 (m, 2H), 1.82-1.79 (m, 1H), 1.62-1.61 (m, 1H), 1.31-1.29 (m, 1H), 1.16 (t, J=7.2 Hz, 3H), 1.05 (t, J=7.2 Hz, 3H).

Similarly prepared by the method of example 29 by substituting 11 with 203.1 to form (1S,2R,3S,4R,5S)-4-(5-chloro-7-((2-hydroxyethyl)amino)-3H-imidazo[4,5-b]pyridin-3-yl)-2,3-dihydroxy-N-methylbicyclo[3.1.0]hexane-1-carboxamide (91). LCMS: 382.1 $(M+H)^+$. $^1H$ NMR: 400 MHz DMSO-$d_6$ δ (ppm) 8.02 (s, 1H), 7.60-7.59 (m, 1H), 7.07 (s, 1H), 6.42 (s, 1H), 5.43 (t, J=4.8 Hz, 1H), 4.93 (d, J=6.8 Hz, 1H), 4.84-4.80 (m, 2H), 4.72 (s, 1H), 3.85 (d, J=4.8 Hz, 1H), 3.60-3.56 (m, 2H), 3.42 (s, 2H), 2.67 (d, J=4.4 Hz, 3H), 1.80-1.78 (m, 1H), 1.64-1.61 (m, 1H), 1.32-1.30 (m, 1H).

Similarly prepared by the method of example 29 by substituting 11 with 204.1 to form (1S,2R,3S,4R,5S)-4-(7-amino-5-chloro-3H-imidazo[4,5-b]pyridin-3-yl)-2,3-dihydroxy-N-methylbicyclo[3.1.0]hexane-1-carboxamide (90). LCMS: 338.1 $(M+H)^+$. $^1H$ NMR: 400 MHz DMSO-$d_6$ δ (ppm) 8.00 (s, 1H), 7.58-7.57 (m, 1H), 6.78 (s, 2H), 6.37 (s, 1H), 5.41 (d, J=4.8 Hz, 1H), 4.94 (t, J=7.2 Hz, 1H), 4.80 (d, J=8.0 Hz, 1H), 4.70 (s, 1H), 3.86-3.83 (m, 11H), 2.66 (d, J=4.8 Hz, 3H), 1.79-1.77 (m, 1H), 1.61 (t, J=4.4 Hz, 1H), 1.30-1.29 (m, 1H).

Similarly prepared by the method of example 29 by substituting 11 with 205.1 to form (1S,2R,3S,4R,5S)-4-(5-chloro-7-((cyclobutylmethyl)amino)-3H-imidazo[4,5-b]pyridin-3-yl)-2,3-dihydroxy-N-methylbicyclo[3.1.0]hexane-1-carboxamide (65). LCMS: 406.1 $(M+H)^+$. $^1H$ NMR: 400 MHz DMSO-$d_6$ δ (ppm) 7.99 (s, 1H), 7.58-7.57 (m, 1H), 7.21 (t, J=6.0 Hz, 1H), 6.36 (s, 1H), 5.41 (d, J=4.8 Hz, 1H), 4.92 (t, J=7.2 Hz, 1H), 4.80 (d, J=8.4 Hz, 1H), 4.70 (s, 1H), 3.86-3.83 (m, 1H), 3.45 (s, 2H), 2.66 (d, J=4.4 Hz, 3H), 2.52-2.50 (m, 1H), 2.05-1.97 (m, 2H), 1.85-1.71 (m, 5H), 1.04 (t, J=4.8 Hz, 1H), 1.30-1.29 (m, 1H).

Similarly prepared by the method of example 29 by substituting 11 with 206.1 to form (1S,2R,3S,4R,5S)-4-(5-chloro-7-(isobutylamino)-3H-imidazo[4,5-b]pyridin-3-yl)-2,3-dihydroxy-N-methylbicyclo[3.1.0]hexane-1-carboxamide (83). LCMS: 394.1 $(M+H)^+$. $^1H$ NMR: 400 MHz DMSO-$d_6$ δ (ppm) 8.01 (s, 1H), 7.59-7.57 (m, 1H), 7.28 (t, J=6.4 Hz, 1H), 6.37 (s, 1H), 5.42 (t, J=4.8 Hz, 1H), 4.95 (t, J=6.8 Hz, 1H), 4.82 (d, J=8.4 Hz, 1H), 4.71 (s, 1H), 3.86 (t, J=4.8 Hz, 1H), 3.21 (s, 2H), 2.68 (d, J=4.8 Hz, 3H), 1.91-1.93 (m, 1H), 1.80-1.78 (m, 1H), 1.64-1.61 (m, 1H), 1.30-1.29 (m, 1H), 0.91 (d, J=6.4 Hz, 6H).

Similarly prepared by the method of example 29 by substituting 11 with 208.1 to form (1S,2R,3S,4R,5S)-4-(5-chloro-7-((cyclopropylmethyl)amino)-3H-imidazo[4,5-b]pyridin-3-yl)-2,3-dihydroxy-N-methylbicyclo[3.1.0]hexane-1-carboxamide (63). LCMS: 392.1 $(M+H)^+$. $^1H$ NMR: 400 MHz CDCl3 δ (ppm) 7.85 (s, 1H), 6.98-6.96 (m, 1H), 6.31 (s, 1H), 5.71 (t, J=6.0 Hz, 11H), 5.17 (s, 1H), 4.94 (d, J=6.8 Hz, 1H), 4.89 (s, 1H), 4.13 (d, J=6.4 Hz, 1H), 3.59 (s, 1H), 3.15 (t, J=5.2 Hz, 2H), 2.92 (d, J=4.8 Hz, 3H), 2.28-2.24 (m, 1H), 1.77 (t, J=4.8 Hz, 1H), 1.38-1.36 (m, 1H), 1.18-1.15 (m, 11H), 0.64-0.62 (m, 2H), 0.33-0.31 (m, 2H).

Similarly prepared by the method of example 29 by substituting 11 with 207.1 to form (1S,2R,3S,4R,5S)-4-(5-chloro-7-(propylamino) 3H-imidazo[4,5-b]pyridin-3-yl)-2,3-dihydroxy-N-methylbicyclo[3.1.0]hexane-1-carboxamide (64). LCMS: 380.1 $(M+H)^+$. $^1H$ NMR: 400 MHz CDCl3 δ (ppm) 7.83 (s, 1H), 6.97-6.94 (m, 1H), 6.32 (s, 1H), 5.60 (t, J=5.2 Hz, 11H), 5.17 (s, 1H), 4.93 (d, J=6.8 Hz, 1H), 4.88 (s, 1H), 4.13 (d, J=6.4 Hz, 1H), 3.58 (s, 11H), 3.30-3.25 (m, 2H), 2.92 (d, J=4.8 Hz, 3H), 2.27-2.25 (m, 1H), 1.78-1.71 (m, 3H), 1.36-1.35 (m, 1H), 1.06-1.02 (m, 3H).

Similarly prepared by method of example 29 by substituting 11 with 209.1 to form (1S,2R,3S,4R,5S)-4-(5-chloro-7-(ethylamino)-3H-imidazo[4,5-b]pyridin-3-yl)-2,3-dihydroxy-N-methylbicyclo[3.1.0]hexane-1-carboxamide (59). (39.6% yield) as white solid. LCMS: 366.1 $(M+H)^+$. $^1H$ NMR: 400 MHz DMSO-$d_6$ δ (ppm) 8.00 (s, 1H), 7.55 (d, J=4.8 Hz, 1H), 7.17 (t, J=5.6 Hz, 1H), 6.34 (s, 1H), 5.39 (d, J=4.4 Hz, 1H), 4.94-4.92 (m, 1H), 4.79 (d, J=8.4 Hz, 1H), 4.71 (s, 1H), 3.85 (t, J=5.2 Hz, 1H), 3.40 (s, 2H), 2.67 (d, J=4.4 Hz, 3H), 1.80-1.77 (m, 1H), 1.61 (t, J=4.8 Hz, 1H), 1.31-1.29 (m, 1H), 1.17 (t, J=6.8 Hz, 3H).

TABLE 10

Compounds prepared by the Examples above with Assay Data

| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| 36 | 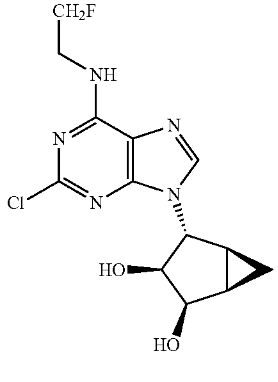 | | | | 9.2 | 44.9 |

TABLE 10-continued
| Compounds prepared by the Examples above with Assay Data | | | | | | |
|---|---|---|---|---|---|---|
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
| 37 | 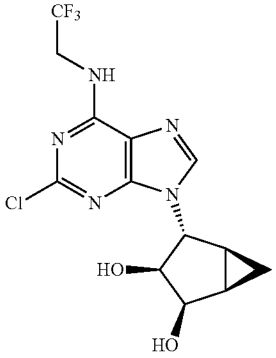 [SMILES: O[C@@H]1[C@H](O)[C@@H]2C[C@@H]2[C@H]1n1cnc2c(NCC(F)(F)F)nc(Cl)nc21] | | | | 12.8 | 49.4 |
| 38 | 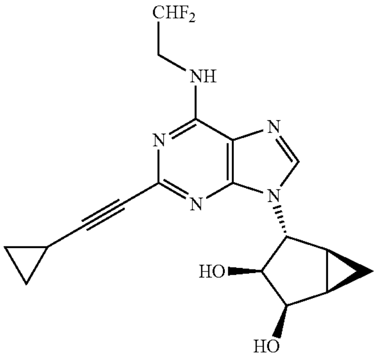 [SMILES: O[C@@H]1[C@H](O)[C@@H]2C[C@@H]2[C@H]1n1cnc2c(NCC(F)F)nc(C#CC3CC3)nc21] | | 1.8 | 65.1 | 14.5 | 24.7 |
| 39 | 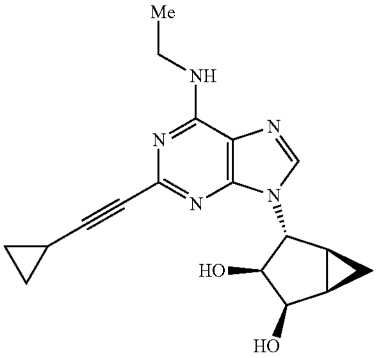 [SMILES: CCNc1nc(C#CC2CC2)nc2c1ncn2[C@H]1[C@H](O)[C@H](O)[C@@H]2C[C@@H]21] | | 0.2 | 54.4 | 9.8 | 15.4 |
| 40 | 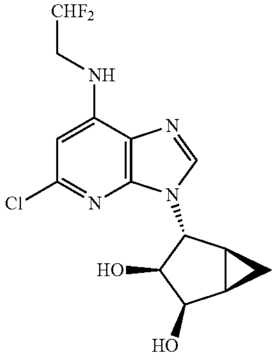 [SMILES: O[C@@H]1[C@H](O)[C@@H]2C[C@@H]2[C@H]1n1cnc2c(NCC(F)F)cc(Cl)nc21] | 2 | 8.6 | 77.6 | 6.1 | 55.9 |

TABLE 10-continued
| Compounds prepared by the Examples above with Assay Data | | | | | | |
|---|---|---|---|---|---|---|
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
| 41 | 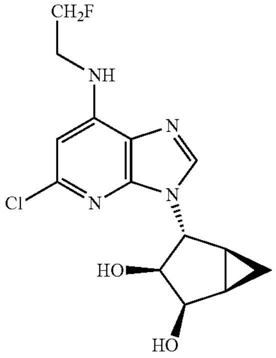 | | | | 36.7 | 31.3 |
| 42 | 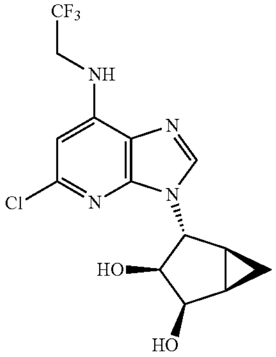 [SMILES: O[C@@H]1[C@H](O)[C@@H]2C[C@@H]2[C@H]1n1cnc2c(NCC(F)(F)F)cc(Cl)nc21] | | | | 43.4 | 45.8 |
| 43 | 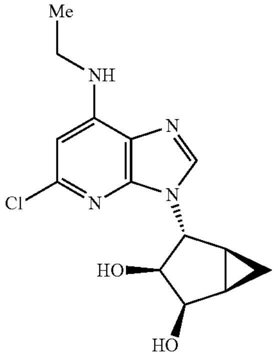 [SMILES: CCNc1cc(Cl)nc2c1ncn2[C@H]1[C@H](O)[C@H](O)[C@@H]2C[C@@H]21] | | | | 5.1 | 50.3 |
| 44 | 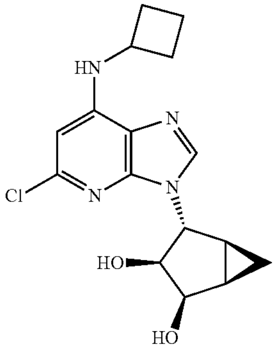 [SMILES: O[C@@H]1[C@H](O)[C@@H]2C[C@@H]2[C@H]1n1cnc2c(NC3CCC3)cc(Cl)nc21] | 28.4 | | | 23.1 | 52 |

TABLE 10-continued
| Compounds prepared by the Examples above with Assay Data | | | | | | |
|---|---|---|---|---|---|---|
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
| 45 | 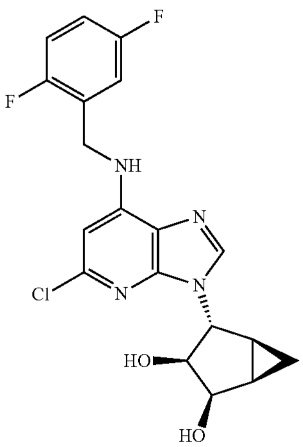 [SMILES: O[C@@H]1[C@H](O)[C@@H]2C[C@@H]2[C@H]1n1cnc2c(NCc3cc(F)ccc3F)cc(Cl)nc21] | 1.3 | | | 29.5 | 22.5 |
| 46 | 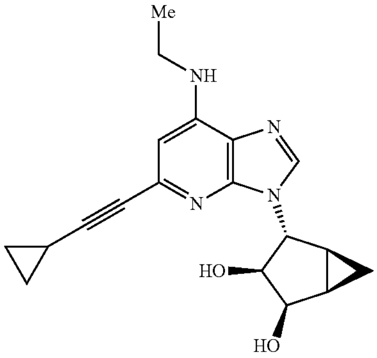 [SMILES: CCNc1cc(C#CC2CC2)nc2c1ncn2[C@H]1[C@H](O)[C@H](O)[C@@H]2C[C@@H]21] | 21.3 | >10000 | 1 | 10000 | 4.8 |
| 47 | 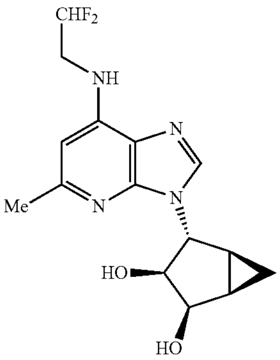 [SMILES: Cc1cc(NCC(F)F)c2ncn([C@H]3[C@H](O)[C@H](O)[C@@H]4C[C@@H]43)c2n1] | | | | 51.2 | 33.1 |

TABLE 10-continued
Compounds prepared by the Examples above with Assay Data
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| 48 | 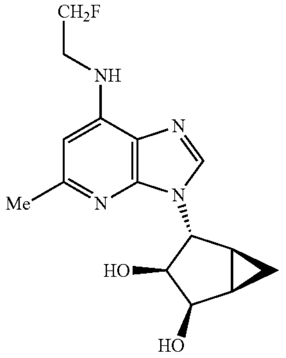 | | | | 37.6 | 13.1 |
| 49 | 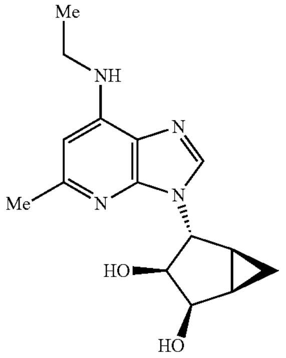 [SMILES: CCNc1cc(C)nc2c1ncn2[C@H]1[C@H](O)[C@H](O)[C@@H]2C[C@@H]21] | | | | 17.1 | 6.8 |
| 50 | 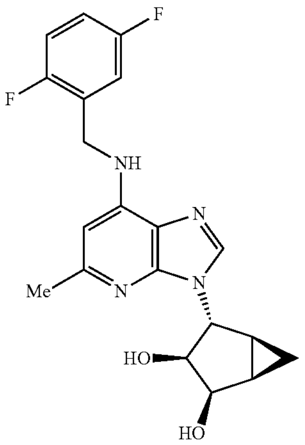 [SMILES: Cc1cc(NCc2cc(F)ccc2F)c2ncn([C@H]3[C@H](O)[C@H](O)[C@@H]4C[C@@H]43)c2n1] | | | | 54 | 12.3 |

TABLE 10-continued
Compounds prepared by the Examples above with Assay Data
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| 51 | 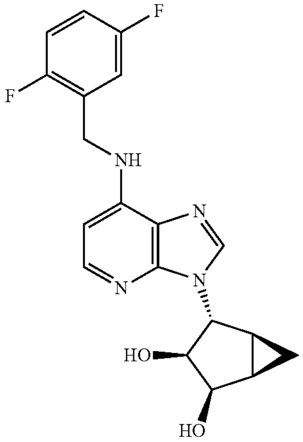 [SMILES: O[C@@H]1[C@H](O)[C@@H]2C[C@@H]2[C@H]1n1cnc2c(NCc3cc(F)ccc3F)ccnc21] | | + | | | |
| 52 | 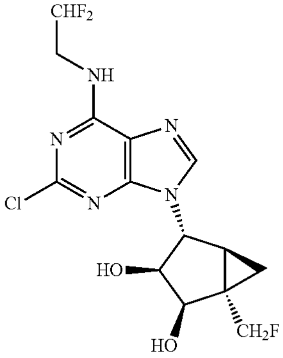 | | + | | | |
| 53 | 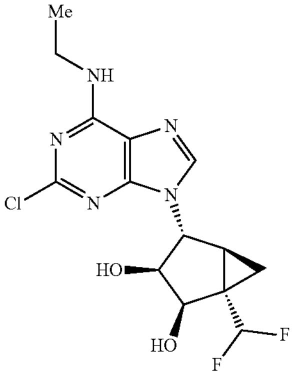 [SMILES: CCNc1nc(Cl)nc2c1ncn2[C@H]1[C@H](O)[C@H](O)[C@]2(C(F)F)C[C@H]12] | | | | 10000 | 0.6 |

TABLE 10-continued
Compounds prepared by the Examples above with Assay Data
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| 54 | 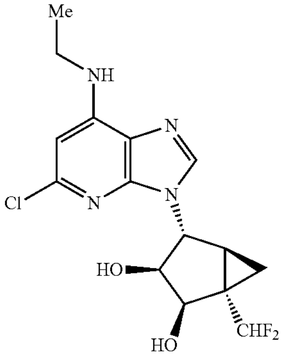 [SMILES: CCNc1cc(Cl)nc2c1ncn2[C@H]1[C@H](O)[C@H](O)[C@]2(C(F)F)C[C@H]12] | | | | | |
| 55 | 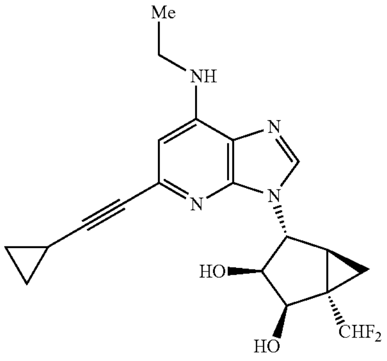 [SMILES: CCNc1cc(C#CC2CC2)nc2c1ncn2[C@H]1[C@H](O)[C@H](O)[C@]2(C(F)F)C[C@H]12] | | | | | |
| 35 | 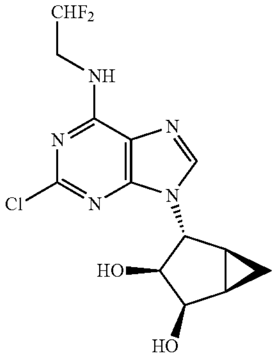 [SMILES: O[C@@H]1[C@H](O)[C@@H]2C[C@@H]2[C@H]1n1cnc2c(NCC(F)F)nc(Cl)nc21] | 1.7 | 1.33 | 80.97 | 4.7 | 46.8 |
| 56 | 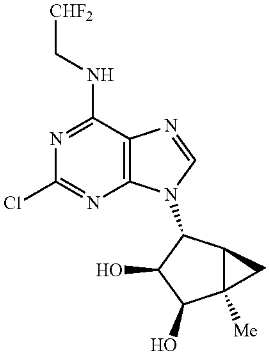 [SMILES: C[C@@]12C[C@@H]1[C@@H](n1cnc3c(NCC(F)F)nc(Cl)nc31)[C@H](O)[C@@H]2O] | | | | | |

TABLE 10-continued
Compounds prepared by the Examples above with Assay Data
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| 57 | 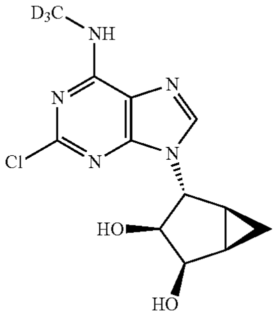 [SMILES: [2H]C([2H])([2H])Nc1nc(Cl)nc2c1ncn2[C@H]1[C@H](O)[C@H](O)[C@@H]2C[C@@H]21] | | | | | |
| 58 | 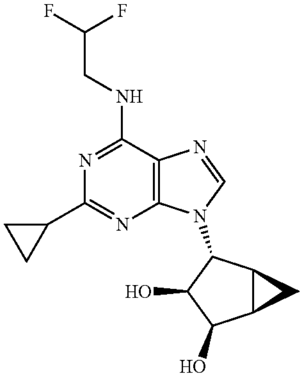 [SMILES: O[C@@H]1[C@H](O)[C@@H]2C[C@@H]2[C@H]1n1cnc2c(NCC(F)F)nc(C3CC3)nc21] | | | | 25.4 | 14.2 |
| 59 | 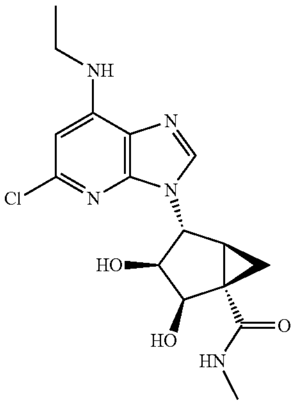 [SMILES: CCNc1cc(Cl)nc2c1ncn2[C@H]1[C@H](O)[C@H](O)[C@]2(C(=O)NC)C[C@H]12] | 0.23 | 0.11 | 106.95 | 1.2 | 103.9 |
| 60 | 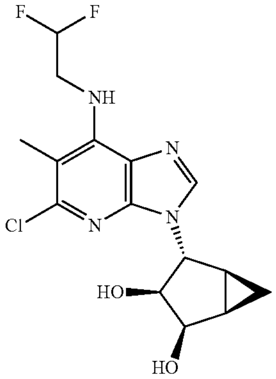 [SMILES: Cc1c(Cl)nc2c(ncn2[C@H]2[C@H](O)[C@H](O)[C@@H]3C[C@@H]32)c1NCC(F)F] | >9400 | >10000 | 1 | >10000 | 10 |

TABLE 10-continued
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| Compounds prepared by the Examples above with Assay Data | | | | | | |
| 61 | 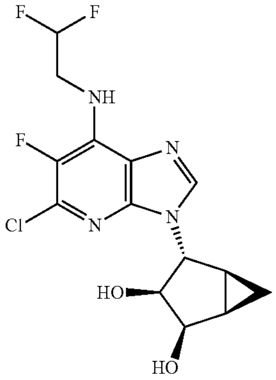 [SMILES: O[C@@H]1[C@H](O)[C@@H]2C[C@@H]2[C@H]1n1cnc2c(NCC(F)F)c(F)c(Cl)nc21] | 7.15 | | | 60 | 67.3 |
| 62 | 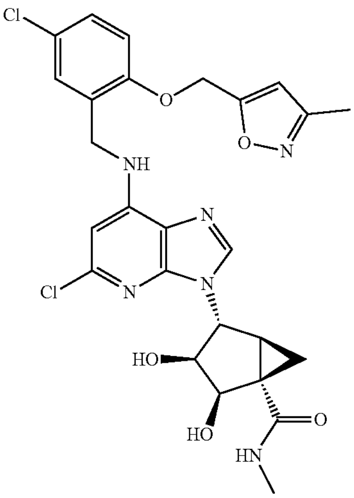 [SMILES: CNC(=O)[C@@]12C[C@@H]1[C@@H](n1cnc3c(NCc4cc(Cl)ccc4OCc4cc(C)no4)cc(Cl)nc31)[C@H](O)[C@@H]2O] | 0.33 | 0.31 | 103.26 | | |
| 63 | 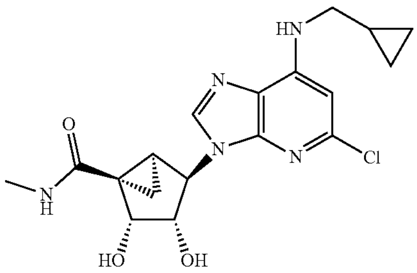 [SMILES: CNC(=O)[C@]12C[C@@H]1[C@@H](n1cnc3c(NCC4CC4)cc(Cl)nc31)[C@H](O)[C@@H]2O] | 0.72 | 0.22 | 105.1 | | |
| 64 | 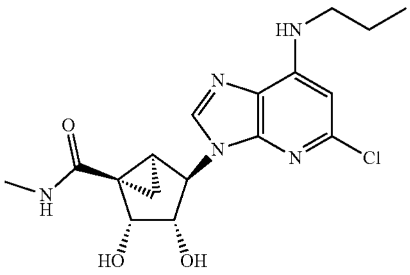 [SMILES: CCCNc1cc(Cl)nc2c1ncn2[C@H]1[C@H](O)[C@H](O)[C@@]2(C(=O)NC)C[C@H]12] | 0.64 | | | | |

TABLE 10-continued
| Compounds prepared by the Examples above with Assay Data | | | | | | |
|---|---|---|---|---|---|---|
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
| 65 | 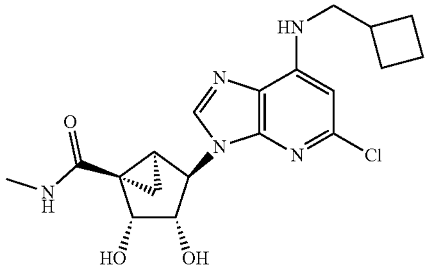 [SMILES: CNC(=O)[C@]12C[C@@H]1[C@@H](n1cnc3c(NCC4CCC4)cc(Cl)nc31)[C@H](O)[C@@H]2O] | 3.49 | | | | |
| 66 | 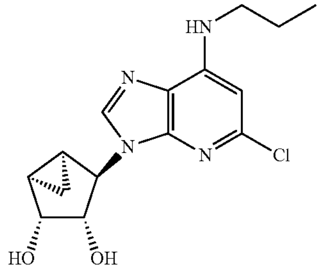 [SMILES: CCCNc1cc(Cl)nc2c1ncn2[C@H]1[C@H](O)[C@H](O)[C@@H]2C[C@@H]21] | 126 | | | | |
| 67 | 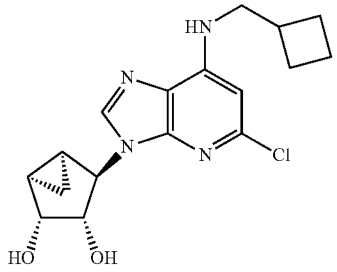 [SMILES: O[C@@H]1[C@H](O)[C@@H]2C[C@@H]2[C@H]1n1cnc2c(NCC3CCC3)cc(Cl)nc21] | 94.4 | | | | |
| 68 | 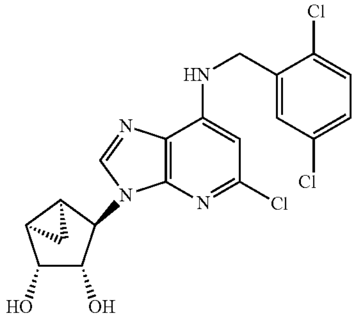 [SMILES: O[C@@H]1[C@H](O)[C@@H]2C[C@@H]2[C@H]1n1cnc2c(NCc3cc(Cl)ccc3Cl)cc(Cl)nc21] | 4.75 | 1.33 | 38.22 | | |
| 69 | 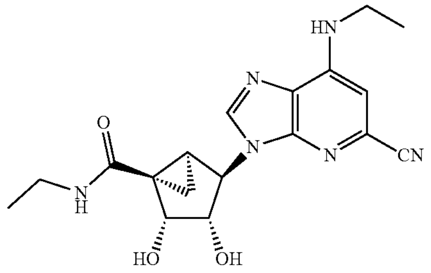 [SMILES: CCNC(=O)[C@@]12C[C@@H]1[C@@H](n1cnc3c(NCC)cc(C#N)nc31)[C@H](O)[C@@H]2O] | 1.68 | | | | |

TABLE 10-continued
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| Compounds prepared by the Examples above with Assay Data | | | | | | |
| 70 | 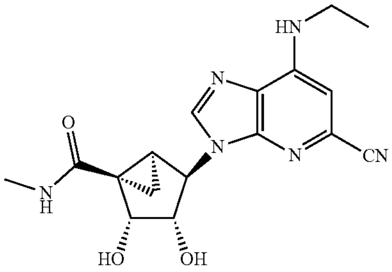 [SMILES: CCNc1cc(C#N)nc2c1ncn2[C@H]1[C@H](O)[C@H](O)[C@]2(C(=O)NC)C[C@H]12] | 0.133 | 0.1 | 104.76 | | |
| 71 | 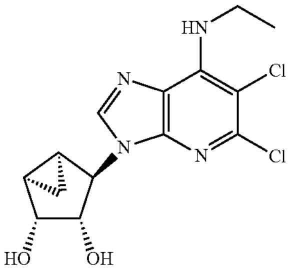 [SMILES: CCNc1c(Cl)c(Cl)nc2c1ncn2[C@H]1[C@H](O)[C@H](O)[C@@H]2C[C@@H]21] | 456 | | | | |
| 73 | 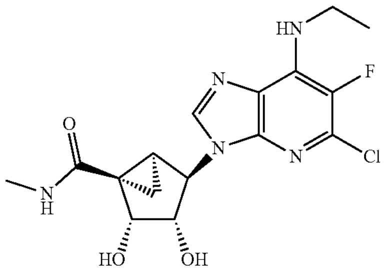 [SMILES: CCNc1c(F)c(Cl)nc2c1ncn2[C@H]1[C@H](O)[C@H](O)[C@]2(C(=O)NC)C[C@H]12] | | | | | |
| 74 | 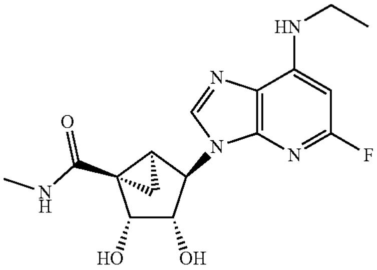 [SMILES: CCNc1cc(F)nc2c1ncn2[C@H]1[C@H](O)[C@H](O)[C@]2(C(=O)NC)C[C@H]12] | | | | | |

TABLE 10-continued
Compounds prepared by the Examples above with Assay Data
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| 75 | 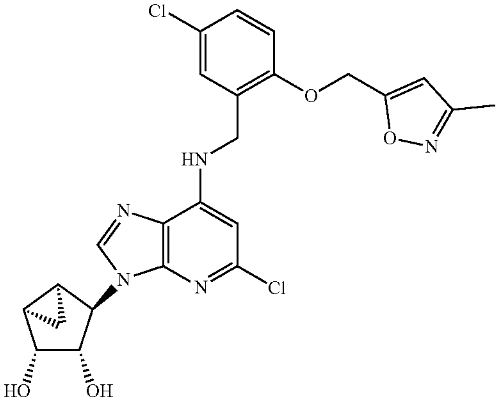 [SMILES: Cc1cc(COc2ccc(Cl)cc2CNc2cc(Cl)nc3c2ncn3[C@H]2[C@H](O)[C@H](O)[C@@H]3C[C@@H]32)on1] | | | | 10000 | 1.7 |
| 77 | 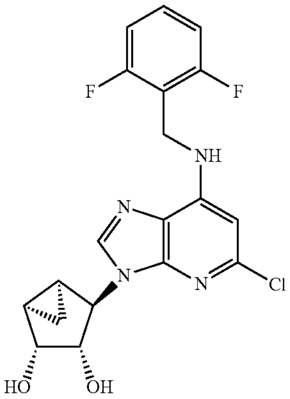 [SMILES: O[C@@H]1[C@H](O)[C@@H]2C[C@@H]2[C@H]1n1cnc2c(NCc3c(F)cccc3F)cc(Cl)nc21] | | | | | |
| 78 | 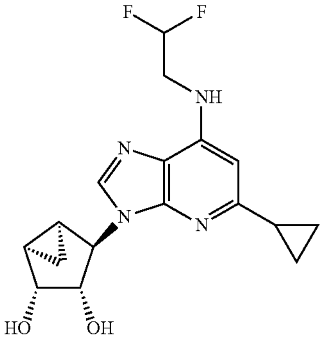 [SMILES: O[C@@H]1[C@H](O)[C@@H]2C[C@@H]2[C@H]1n1cnc2c(NCC(F)F)cc(C3CC3)nc21] | | | | 110.2 | 7.2 |
| 79 | 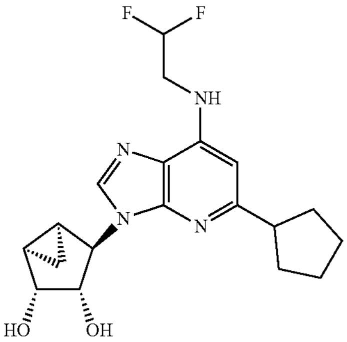 [SMILES: O[C@@H]1[C@H](O)[C@@H]2C[C@@H]2[C@H]1n1cnc2c(NCC(F)F)cc(C3CCCC3)nc21] | | | | | |

TABLE 10-continued
Compounds prepared by the Examples above with Assay Data
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
|---|---|---|---|---|---|---|
| 80 | 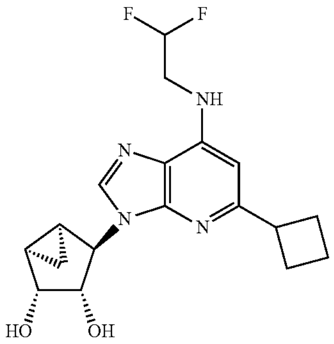 [SMILES: O[C@@H]1[C@H](O)[C@@H]2C[C@@H]2[C@H]1n1cnc2c(NCC(F)F)cc(C3CCC3)nc21] | | | | | |
| 81 | 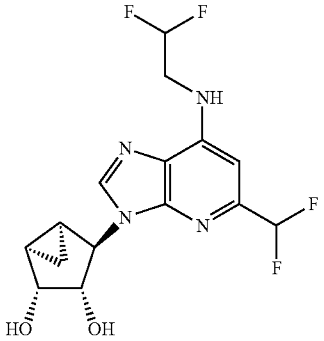 [SMILES: O[C@@H]1[C@H](O)[C@@H]2C[C@@H]2[C@H]1n1cnc2c(NCC(F)F)cc(C(F)F)nc21] | | | | | |
| 82 | 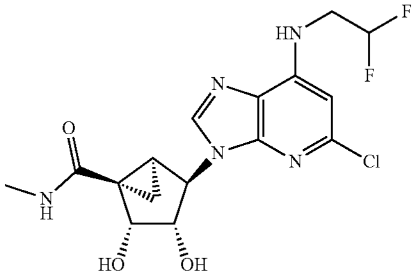 [SMILES: CNC(=O)[C@@]12C[C@@H]1[C@@H](n1cnc3c(NCC(F)F)cc(Cl)nc31)[C@H](O)[C@@H]2O] | 4.77 | | | 1.9 | 106 |
| 83 | 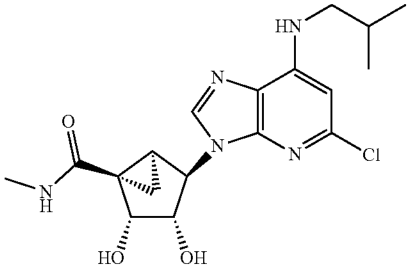 [SMILES: CNC(=O)[C@@]12C[C@@H]1[C@@H](n1cnc3c(NCC(C)C)cc(Cl)nc31)[C@H](O)[C@@H]2O] | 1.62 | | | | |

TABLE 10-continued
| Compounds prepared by the Examples above with Assay Data | | | | | | |
|---|---|---|---|---|---|---|
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
| 84 | 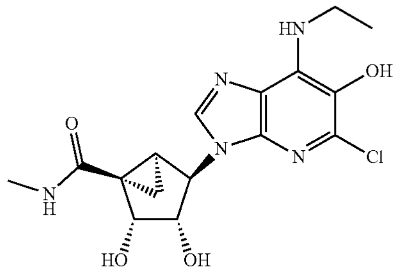 [SMILES: CCNc1c(O)c(Cl)nc2c1ncn2[C@H]1[C@H](O)[C@H](O)[C@]2(C(=O)NC)C[C@H]12] | | | | | |
| 85 | 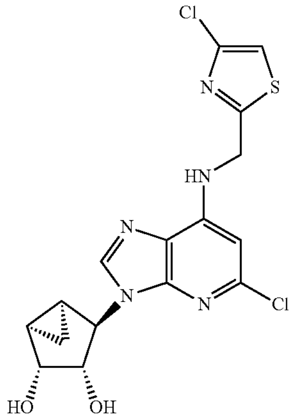 [SMILES: O[C@@H]1[C@H](O)[C@@H]2C[C@@H]2[C@H]1n1cnc2c(NCc3nc(Cl)cs3)cc(Cl)nc21] | | | | | |
| 86 | 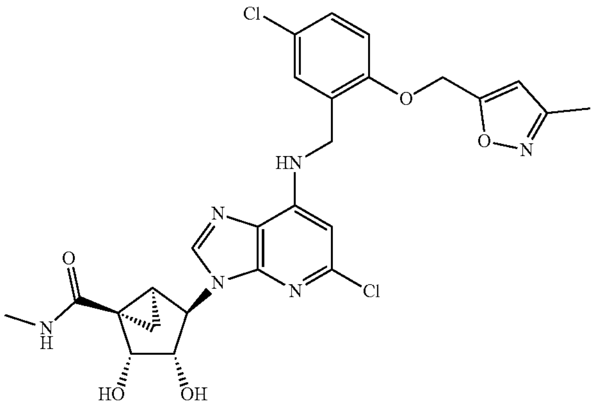 | | | | | |

TABLE 10-continued
| Compounds prepared by the Examples above with Assay Data | | | | | | |
|---|---|---|---|---|---|---|
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
| 88 | 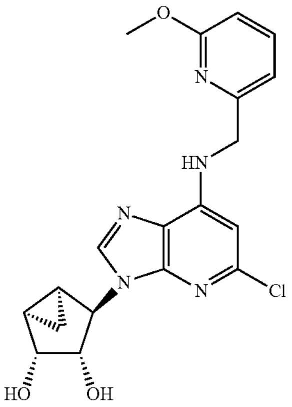 [SMILES: COc1cccc(CNc2cc(Cl)nc3c2ncn3[C@H]2[C@H](O)[C@H](O)[C@@H]3C[C@@H]32)n1] | | | | | |
| 89 | 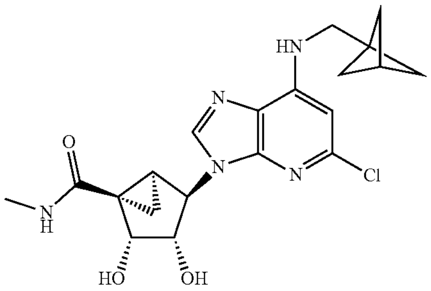 [SMILES: CNC(=O)[C@@]12C[C@@H]1[C@@H](n1cnc3c(NCC45CC(C4)C5)cc(Cl)nc31)[C@H](O)[C@@H]2O] | | | | | |
| 90 | 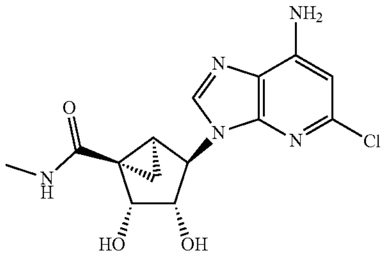 [SMILES: CNC(=O)[C@@]12C[C@@H]1[C@@H](n1cnc3c(N)cc(Cl)nc31)[C@H](O)[C@@H]2O] | 2.42 | | | | |
| 91 | 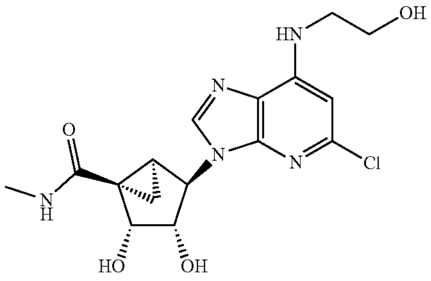 [SMILES: CNC(=O)[C@@]12C[C@@H]1[C@@H](n1cnc3c(NCCO)cc(Cl)nc31)[C@H](O)[C@@H]2O] | 5.1 | | | | |

TABLE 10-continued

| Compounds prepared by the Examples above with Assay Data | | | | | | | |
|---|---|---|---|---|---|---|---|
| Compound ID # | Structure | hA3 Ki: Ki (nM) | CAMP EC50 (nM) | CAMP Efficacy (%) | Cell Calcium Assay EC50 (nM) | Cell Calcium Efficacy (%) |
| 92 | 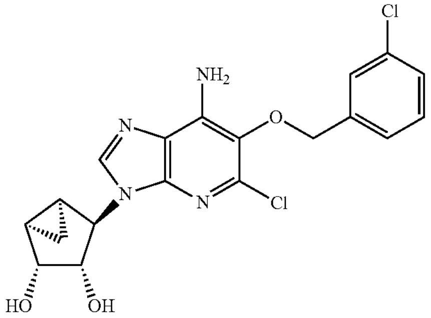 [SMILES: Nc1c(OCc2cccc(Cl)c2)c(Cl)nc2c1ncn2[C@H]1[C@H](O)[C@H](O)[C@@H]2C[C@@H]21] | 26.8 | | | | |
| 93 | 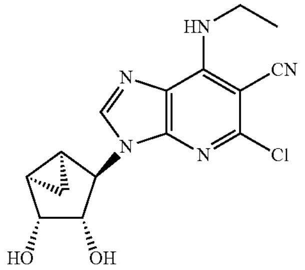 [SMILES: CCNc1c(C#N)c(Cl)nc2c1ncn2[C@H]1[C@H](O)[C@H](O)[C@@H]2C[C@@H]21] | 2.59 | 15.25 | 52 | | |

Example 30: Adenosine Receptor Binding Assay

Materials and Reference Compounds: [$^{125}$I]-AB-MECA and [$^{3}$H]CCPA are both obtained from Amersham Biosciences (Little Chalfont, UK). IB-MECA are obtained from Tocris (Bristol, UK) and N6-cyclopentyl adenosine (CPA) is obtained from Sigma-Alrich (Poole, UK). Cell culture media, G418 and hygromycin are obtained from Invitrogen (Paisley, UK). Fetal calf serum is obtained from Perbio Science (Cheshire, UK). All other reagents are obtained from Fisher Chemicals (Loughborough, UK).

Cell Culture and Membrane Preparation: This example demonstrates the binding affinity to human A3 or A1 receptors stably expressed in either Chinese hamster ovary (CHO-K1) cells (for the A1 receptor) or BEK-293 cells (for the A3 receptor) exhibited by compounds in accordance with an embodiment of the invention. The method followed is that of Yates L, Clark J H, Martin T J, James S, Broadley K J, Kidd E J. Radioligand binding and functional responses of ligands for human recombinant adenosine $A_3$ receptors. Auton Autacoid Pharmacol. 2006; 26(2):191-200. Cells stably transfected with the human adenosine $A_3$ or $A_1$ receptor are grown in Dulbecco's modified Eagles medium with nutrient mixture F12 containing $NaHCO_3$ and Glutamax. Media is supplemented with 10% fetal calf serum, geneticin (G418; 0.67 mg/mL), hygromycin (500 μg/mL) and adenosine deaminase (1 U/mL). Cells are maintained at 37° C. with 5% $CO_2$ in air. Cells are harvested and homogenized in ice-cold Tris buffer [50 mM Tris, 150 mM NaCl, 1 mM ethylenediaminetetraacetic acid (EDTA), pH 7.4] supplemented with the peptidase inhibitors, 4-(2-aminoethyl)benzenesulfonylfluoride (1 mM) and bacitracin (0.1 mg/mL), using a Polytron homogenizer (3×10 s bursts). The homogenate was spun for 10 min (4° C.) at 500 g. The supernatant is retained and the pellet is re-suspended in the buffer, homogenized and spun as above. The combined supernatants are centrifuged for 15 min (4° C.) at 48,000 g. The resultant pellet is re-suspended in the buffer and centrifuged for a second time at 48,000 g. The membrane pellet is then suspended in Tris buffer containing no peptidase inhibitors or adenosine deaminase and stored at −80° C. at a protein concentration of 1 mg/mL.

Binding Assays: Radioligand-binding assays were performed using the adenosine $A_3$ receptor agonist [$^{125}$I]-AB-MECA and the $A_1$ receptor agonist [$^{3}$H]CCPA. Binding assays were conducted in a total volume of 100 μL containing a 50 mM Tris, pH 7.4 buffer with or without 10 mM $MgCl_2$, 20 μg membranes and either 0.15 nM [$^{125}$I]-AB-MECA (for the $A_3$ receptor) or 1 nM [$^{3}$H]CCPA (for the $A_1$ receptor). Assays were conducted at room temperature for 60 min ($A_1$ receptor) or 120 min ($A_3$ receptor) and terminated by the addition of 2 ml of ice-cold wash buffer (50 mM Tris, pH 7.4 with or without 10 mM $MgCl_2$) and rapid filtration over 0.03% polyethylenimine-treated Whatman GF/C filters using a Brandel cell harvester (Semat International Ltd., St Albans, UK). Filters were then washed three times with 2 ml of ice-cold buffer. The filter-bound radioactivity were counted using a Compugamma counter (LKB Wallac, Turku, Finland). Competition experiments were performed to investigate the ability of reference compounds and embodiments of the invention to inhibit [$^{125}$I]-AB-MECA binding. Non-specific binding were determined using the respective compound at its highest concentration.

Data Analysis: The $K_d$ and $B_{max}$ values for binding data were calculated based upon the molar amounts of bound and free [$^{125}$I]-AB-MECA. A one-site binding curve was then fitted to these data by Prism (GraphPad) and used to derive the $K_d$ and $B_{max}$ values. $IC_{50}$ and $K_i$ values and Hill slopes for inhibition of the radioligand binding by the compounds of the invention were calculated from the ligand competition curves using the Excel spreadsheet and the $K_d$ value calculated for either [$^{125}$I]-AB-MECA or [$^3$H]CCPA. The results were expressed as a percent of control specific binding and as a percent inhibition of control specific binding obtained in the presence of the compounds of the invention. The $IC_{50}$ values (concentration causing a half-maximal inhibition of control specific binding) and Hill coefficients (nH) were determined by non-linear regression analysis of the competition curves generated with mean replicate values using Hill equation curve fitting:

$$Y = D + \left[\frac{A - D}{1 + (C/C_{50})^{nH}}\right]$$

where Y=specific binding, A=left asymptote of the curve, D=right asymptote of the curve, C=compound concentration, C50=$IC_{50}$, and nH=slope factor. This analysis is performed using software developed at Cerep (Hill software) and validated by comparison with data generated by the commercial software SigmaPlot® 4.0 for Windows®. The inhibition constants ($K_i$ values) were calculated using the Cheng-Prusoff equation:

$$K_i = \frac{IC_{50}}{(1 + L/K_D)}$$

where L=concentration of radioligand in the assay, and $K_D$=affinity of the radioligand for the receptor. A Scatchard plot is used to determine the $K_D$. For [$^{125}$I]-AB-MECA, L=0.15 nM and $K_D$=0.22 nM. Table 10 includes $K_i$ values for the compounds described herein.

Example 31: Intracellular cAMP Levels

This example demonstrates the effect on intracellular cAMP levels in Chinese hamster ovary (CHO-K1) cells exhibited by compounds in accordance with an embodiment of the invention. The method followed is that published in Yates L, Clark J H, Martin T J, James S, Broadley K J, Kidd E J. Radioligand binding and functional responses of ligands for human recombinant adenosine $A_3$ receptors. Auton Autacoid Pharmacol. 2006 April; 26(2):191-200.

Materials and Cell Culture: Adenosine deaminase was obtained from Roche (Lewes, UK). Forskolin was obtained from Sigma-Aldrich (Poole, UK). The sources of other materials are provided above in Example 1. CHO-K1 cells stably transfected with the human adenosine A3 receptor were grown in Dulbecco's modified Eagles medium with nutrient mixture F12 containing $NaHCO_3$ and Glutamax. Media was supplemented with 10% fetal calf serum, geneticin (G418; 0.67 mg/mL), hygromycin (500 µg/mL) and adenosine deaminase (1 U/mL). Cells were maintained at 37° C. with 5% CO2 in air.

cAMP Measurements: Intracellular cAMP production was measured directly using a non-acetylation cAMP enzyme immunoassay (Amersham Biosciences, Little Chalfont, UK). Cultured CHO cells expressing human adenosine $A_3$ receptors were allowed to plate overnight in 96-well plates in culture medium containing adenosine deaminase. Twenty-four hours later, they were incubated with adenosine analogues or compounds of the invention (0.1 nM-1 µM) for 5 min at 37° C., followed by incubation with forskolin (10 µM) for 10 min. The cells were then lysed with 200 µL of lysis reagent 1 provided with the kit for 10 min to release intracellular cAMP. Aliquots of the supernatants were then transferred to a 96-well microtitre plate coated with donkey anti-rabbit IgG; 100-µL cAMP standards (12.5-3200 fmol/well) were also added to the microtitre plate; 100 µL of rabbit anti-cAMP antibody was added to all wells and incubated at 2-5° C. for 2 h. The antiserum was made up in lysis reagent 2, which sequesters the key component in lysis reagent 1 and ensures that cAMP is free for subsequent analysis. Then 50 µL of cAMP peroxidase conjugate was added to all wells and left to incubate for 60 min at 2-5° C. to allow competition for the antibody between the un-labelled and horse radish peroxidase (HRP)-labelled cAMP. Wells were then washed with buffer and 150 µL of enzyme substrate containing 3,3',5,5'-tetramethylbenzidine/hydrogen peroxide in 20% (v/v) dimethylformamide was added to each well and left to incubate for 60 min on a Titramax 100 microtitre plate shaker (Heidolph Instruments, Schwabach, Germany) at room temperature for color development. The reaction was stopped by the addition of 100 µL of 1 M sulfuric acid and the optical density (OD) read at 450 nm on a spectrophotometric MRX microplate reader (Dynex Technologies, Chantilly, VA, USA).

Analyses: Each sample/standard was analyzed in duplicate and the resulting OD values averaged. The percent bound (B/Bo) for each standard and sample was calculated using the following relationship:

$$\% B/B_0 = \frac{\text{standard or sample } OD - \text{non-specific blank } OD}{\text{zero standard } OD - \text{non-specific blank}} \times 100$$

where B is the specific OD for standard/sample and Bo is the specific OD for the zero standard. A standard curve was generated by plotting % B/Bo as a function of the log fmol cAMP standard per well. The fmol per well value for cAMP in each sample was then read from the graph. The results are expressed as a percent of control agonist response: (measured response/control response)*100 in the presence of the compounds of the invention. Concentration-response curves for inhibition of cAMP production were constructed for all compounds of the invention and reference compounds. The $EC_{50}$ values (concentration producing a half-maximal response) were determined by non-linear regression analysis of the concentration-response curves generated with mean replicate values using Hill equation curve fitting, according to the equation:

$$Y = D + \left[\frac{A - D}{1 + (C/C_{50})^{nH}}\right]$$

where Y=response, A=left asymptote of the curve, D=right asymptote of the curve, C=compound concentration, and $C_{50}$=$EC_{50}$, and nH=slope factor. This analysis was performed using software developed at Cerep (Hill software) and validated by comparison with data generated by the commercial software SigmaPlot© 4.0 for Windows®. Table 10 includes $EC_{50}$ values for compounds described herein.

The maximal response is reported as a percentage of the response produced by 100 nM IB-MECA.

Example 32: Intracellular Calcium Release Assay

This example demonstrates the effect on intracellular calcium levels in either CHO-K1 or HEK293 cells stably expressing the four subtypes of adenosine receptors that were induced by test compounds, in accordance with an embodiment of the invention.

Cell Culture: The table below lists the cell lines used that stably express the 4 subtypes of adenosine receptors, along with the growth medium used for each:

| Target | Host Cell | Growth Medium |
|---|---|---|
| ADORA1 | HEK293 | DMEM + 10% FBS; G418 300 μg/mL; Blasticidin: 2 μg/mL |
| ADORA2A | CHO-K1 | F12 + 10% FBS; G418 300 μg/mL; Blasticidin: 2 μg/mL |
| ADORA2B | HEK293 | DMEM + 10% FBS; G418 300 μg/mL; Blasticidin: 2 μg/mL |
| ADORA3 | CHO-K1 | F12 + 10% FBS; G418 300 μg/mL; Blasticidin: 2 μg/mL |

For experiments with the ADORA1- and ADORA3-expressing cells, the medium was aspirated and the cells washed twice with 10 mL DPBS. Two mL of trypsin was added and incubated at 37° C. for 1 minute. Then 10 mL of platting media was added to terminate the digestion and 1 mL of the solution was taken out for cell counting. ADORA2A- and ADORA2B-expressing cells were thawed rapidly in a 37° C. water bath. Cell suspensions were transferred to 50 mL conical tubes. Plating media was added to the 10 mL mark and then 1 mL taken out for cell counting. The 50 mL tubes containing the various types of cells were centrifuged at 1000 g. Then the supernatants were aspirated, being careful not to aspirate the cells. The cell pellets were resuspended in 3-5 mL platting media, then 0.5 mL was taken out for cell counting. Then the cell suspension was diluted to $1\times10^6$ cells/mL (20,000 cells per 20 μL per well) in platting medium, and cells were seeded into 384-well cell plates (Greiner-781946). The 384-well cell plate was placed in a 37° C./5% $CO_2$ incubator (Thermo-371, Thermo Scientific) for 16-20 hours.

Preparation of the intracellular calcium imaging agent (Fluo-4 Direct™ Calcium Assay Kit, Invitrogen-F10471, Thermo Scientific): One mL of FLIPR Assay Buffer was added to 77 mg probenecid to make a 250 mM solution, which was used fresh for each day. One vial of Fluo-4 Direct™ crystals was thawed and 10 mL of FLIPR Assay Buffer was added to the vial. 0.2 mL of probenecid was added to each 10 mL vial of Fluo-Direct™ solution, such that the final assay concentration was 2.5 mM. It was vortexed, left to stand >5 min and protected from light. The dye was prepared fresh each day.

Compound Preparation: Compound plates were prepared as follows. First, the test compound was diluted to prepare a 2 mM solution and then 10-point 3-fold serial dilutions were made using ECHO (ECHO 555, LabCyte), then 900 nL was transferred to the compound plate. For all targets, the final top concentration of the test compound was 10 PM. For agonist reference compounds, 10-point and 3-fold serial dilutions were made, then 900 nL was transferred to the assay plate. Then 30 μL of assay buffer was added to the compound plate and then the plate was centrifuged at 1000 rpm for 1 min.

FLIPR Assay: Cell plates were removed from the incubator, to which were added 20 μL 2×Fluo-4 Direct™ solution, then the plates were reincubated in a 5% $CO_2$, 37° C. incubator for 50 min and at RT for 10 min. To run the protocol on the Fluorescent Imaging Plate Reader (FLIPR) TETRA (MD-FT0249, Molecular Devices, Inc.), 10 μL of assay buffer was transferred from the 384-well plate (Greiner-781280) to the cell plates and then the fluorescence signal was read. Then 10 μL of compound solution was transferred from the compound plate to the cell plates and the fluorescence signal was read. The "Max-Min" was calculated, starting from Read 91 to the maximum allowed. For agonists, activation %=(RLU−LC)/(HC−LC)*100, based on the following: RLU=relative light unit, 91 to maximum allowed signal; HC=average signal of the high concentration of agonist; LC=average signal of DMSO well. The data were fitted using GraphPad Prism 5, using the model "log(agonist) vs. response—Variable slope" to determine the $EC_{50}$ value. The receptor efficacy of the test compound relative to the agonist NECA was calculated as a percentage (%) of the response to 1 FM NECA. Table 10 includes $EC_{50}$ values for compounds described herein.

Example 33: Neuropathic Pain Animal Model

This example evaluates the performance of compounds that embody the invention in an in vivo model of neuropathic pain. The assay was performed as described in Little J W, Chen Z, Doyle T, Porreca F, Ghaffari M, Bryant L, Neumann W L, Salvemini D. Supraspinal peroxynitrite modulates pain signaling by suppressing the endogenous opioid pathway. J Neurosci. 2012; 32(32):10797-808. Animals and Neuropathic Injury: Male Sprague Dawley rats (225-270 g) (Harlan Laboratories) are used for all studies. Rats were housed in a climate-controlled room on a 12 h light/dark cycle with food and water provided ad libitum. All experiments are performed in accordance with the International Association for the Study of Pain (Seattle, MD) and the National Institutes of Health (NIH; Bethesda, MD) guidelines on laboratory animal welfare. All observers are blinded to treatment conditions. Rats were anesthetized and received a chronic constriction injury (CCI) of the sciatic nerve using modifications of a commonly used method (Bennett and Xie, 1988).

The posterolateral thigh was shaved, scrubbed with Nolvasan®, and a 2-cm incision was made through the skin. The left common sciatic nerve was exposed at mid-thigh by blunt dissection. Proximal to the sciatic nerve trifurcation, about 7 mm of the nerve was freed of adhering tissue and then three 4-0 silk sutures were tied loosely around the nerve, causing slight constriction with about 1-mm spacing. The incision is then closed using 5-0 silk sutures. Mechanical allodynia is determined using von Frey filaments to measure mechanical paw withdrawal thresholds (PWTs) in grams. Rats are acclimated to a Plexiglas chamber with a wire mesh floor for 15 min. The PWT is assessed three times at each time point and reported as the mean mechanical PWT (in grams) for both the ipsilateral and contralateral paws. On Day 0 (D0), PWTs re assessed before surgery and subsequently on the desired day post-surgery. Mechanical allodynia was defined as a significant ($p<0.05$) reduction in mean PWT compared to D0. Seven days (D7) provided the maximal PWT reduction ipsilaterally and was used as the target time point for compound evaluations.

Compound Administration: Compounds were administered orally to rats by dissolving it in 0.5% methylcellulose and 0.1% DMSO in distilled water. The solution was sonicated until all materials were dissolved. The administered dose volume was 2 mL/kg. Oral dose levels of 0.3 to 30 mg/kg were evaluated in the CCI rats. There were 5 rats at 0.3 to 3 mg/kg dose levels and 4 rats at the 10 mg/kg dose level.

Data Analysis: Compounds of the invention reduced average mechanical allodynia in the limb with the CCI as evidenced by a statistically significant increase in paw withdrawal threshhold at 1 and 2 hours after oral administration. Compounds of the disclosure did not affect paw withdrawal thresholds in the limb without the CCI surgery. Treatment with the vehicle alone produces no effects on mechano-allodynia in this animal model.

Example 34: GTPγ[$^{35}$S] Scintillation Proximity Assay (SPA)

The assay is used to monitor activation of A3 adenosine receptors (A3AR) by test compounds using protocols similar to published methods for A1AR (Langemeijer et al., Purinergic Signalling 9:91 (2013)). Membrane homogenates of CHO-K1 cells expressing recombinant human A3AR membrane extracts are equilibrated in assay buffer (20 mM HEPES pH 7.4; 100-200 mM NaCl, 10 μg/ml saponin, MgCl2, 0-0.1% BSA). Membranes are mixed with GDP. In parallel, GTPg[$^{35}$S] is mixed with the SPA imaging beads with polyvinyltoluene and wheat germ agglutinin (PVT-WGA (Perkin Elmer, RPNQ001) and then diluted in assay buffer at 50 mg/ml (0.5 mg/10 μl)). The following reagents are successively added in the wells of an Optiplate (Perkin Elmer): 50 μl of test or reference ligand, 10 μl of assay buffer, 20 μl of the membranes: GDP mix, and 20 μl of the GTPg[$^{35}$S]: beads mix. The plates are covered with a top seal, mixed on an orbital shaker for 2 min, and then incubated for 1 hour at room temperature. Then the plates are centrifuged for 10 min at 2000 rpm, incubated at room temperature 1 hour and counted for 1 min/well with a PerkinElmer TopCount reader.

Measurements are made in duplicate, test compounds were evaluated at 10 concentrations varying by half log dilutions from 10 mM to 0.3 nM. Percent activation was fit to a model for a ligand binding reaction with 4 free parameters using Prism software (Graphpad)

Example 35: Inhibition of Pro-Inflammatory Cytokine Release from Human Peripheral Blood Mononuclear Cells (PBMC's)

The anti-inflammatory activity of test compounds was assessed by quantifying the secretion of TNFa and IL-1b from human PBMCs.

Cell Preparation

Cryopreserved human PBMCs (StemCell Technologies 70025.1) are typically purchased from defined donors. Vials are thawed in a 37° C. water bath until only a small ice crystal remains. Cells are gently transferred to a 50 ml Falcon tube and the vial is rinsed with 1 ml of pre-warmed assay medium (DMEM [Sigma 6456]+10% FCS ([Sigma F9665]+1× Glutamax [Invitrogen 350500380]) which is then pooled with the cells with gentle mixing. The cells are then diluted in 20 ml of warm medium by dropwise addition with gentle mixing before centrifugation (300×g for 10 minutes). After pouring off the supernatant, the pellet is resuspended in the remaining volume by gentle flicking. 20 ml of fresh medium is added as before and gently mixed with the pellet. DNAse (Sigma 10104159001) is added to 0.1 mg/ml final concentration (from a 1 mg/ml stock made in PBS and filter sterilised), mixed and incubated for 10 minutes at room temperature. Cells are then centrifuged (300×g for 10 minutes) and supernatant poured off before resuspending the pellet in the remaining liquid by gentle flicking. Cells are then diluted in 1 ml medium and counted using Luna II cell counter with 1:2 dilution in trypan blue. Cells are then diluted in medium to target density; typically seeded at 15,000 or 25,000 cells/well in 40 l/well in a black clear-bottomed 384 well plate (Greiner 781091). Cells are recovered in an incubator (37° C., 5% $CO_2$) overnight before experiment.

Cytokine Assay

All cell treatments are typically added as 5 μl of a 11-fold concentrated stock made in assay medium and incubated in a 37° C., 5% $CO_2$ incubator. Typically, cells are pre-treated with test compound in the presence of adenosine deaminase (Sigma A5043-250UN) for 1 hour before priming with LPS (1 ng/ml of Sigma L3129) for a subsequent 4 hours. The NLRP3 inflammasome is then activated by addition of 6.7 μM nigericin (Invivogen tiri-nig) with incubation for 3 hours. Supernatants are sampled for cytokine quantification and 4 μl added to white low volume 384 well assay plates (Greiner 784075); for IL-1β this is after nigericin stimulation, for TNFα this is before nigericin stimulation. Supernatants are diluted in medium so as to be within AlphaLISA detection range (typically this is 1:50 for IL-1β and 1:10 for TNFα). A mix of AlphaLISA acceptor beads and biotinylated antibody is prepared in AlphaLISA immunoassay buffer, 4 μl added to the supernatant and incubated at 4° C. overnight. 2 μl of streptavidin donor bead mix is then added and incubated for 30-60 minutes at room temperature with shaking. Plates are then read using a Pherestar and AlphaLISA signal interpolated from a standard curve of known concentrations of each cytokine (prepared separately for each assay plate). AlphaLISA kits are from Perkin Elmer (IL-1β; AL220C, TNFα; AL208C).

Data analysis is conducted using Prism software (Graphpad). The concentration-response curve is fit to a 4 parameter non-linear function describing inhibition.

What is claimed is:

1. A compound represented by Formula (II'):

(II')

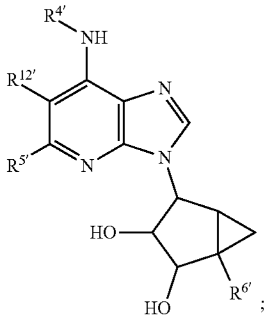

or a pharmaceutically acceptable salt thereof, wherein:

$R^{4'}$ is selected from hydrogen, optionally substituted $C_1$-$C_6$ alkyl, optionally substituted $C_3$-$C_8$ carbocycle, and optionally substituted 3 to 8-membered heterocycle, wherein optional substituents on $C_1$-$C_6$ alkyl are independently selected at each occurrence from $R^7$ and optional substituents on $C_3$-$C_8$ carbocycle and 3 to 8-membered heterocycle are independently selected from $R^8$, $R^{5'}$ is selected from hydrogen, $C_1$-$C_6$ alkyl, $C_3$-$C_6$ cycloalkyl, —$NO_2$, —CN, —$NH_2$, and halogen;

$R^{6'}$ is selected from hydrogen, —C(O)($NR^{50}{}_2$), and optionally substituted $C_1$-$C_3$ alkyl, wherein optional substituents on $C_1$-$C_3$ alkyl are independently selected from $R^{10}$, each $R^7$, and $R^{10}$ is independently selected at each occurrence from:

fluorine, —$OR^{30}$, —$N(R^{30})_2$, —$C(O)R^{30}$, —C(O) $OR^{30}$, —OC(O) $R^{30}$, —$NO_2$, and —CN; and $C_{3-6}$ carbocycle and 3- to 6-membered heterocycle each of which is optionally substituted with one or more substituents independently selected from halogen, —$OR^{31}$, —$N(R^{31})_2$, —$NO_2$, —CN, and $C_{1-3}$ alkyl;

each $R^8$ is independently selected at each occurrence from:

halogen, —$OR^{30}$, —$N(R^{30})_2$, C(O) $R^{30}$, —C(O) $OR^{30}$, —OC (O) $R^{30}$, —$NO_2$, and —CN;

and $C_{1-3}$ alkyl optionally substituted with one or more substituents independently selected from halogen, —$OR^{30}$, —$N(R^{30})_2$, —$NO_2$, —CN, $C_{3-6}$ carbocycle and 3- to 6-membered heterocycle;

each $R^{30}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, and 3- to 6-membered heterocycle;

each $R^{31}$ is independently selected at each occurrence from hydrogen, and $C_{1-6}$ alkyl optionally substituted with one or more substituents independently selected from halogen, —OH, —CN, —$NO_2$, —$NH_2$, —O—$C_{1-6}$ alkyl, $C_{3-6}$ carbocycle, and 3- to 6-membered heterocycle, wherein the $C_{3-6}$ carbocycle and 3- to 6-membered heterocycle are optionally substituted with one or more substituents independently selected from halogen, —OH, —CN, —$NO_2$, —$NH_2$, —O—$C_{1-6}$ alkyl, and —$C_{1-6}$ alkyl;

each $R^{50}$ is independently selected at each occurrence from hydrogen, and $C_{1-6}$ alkyl; and $R^{12'}$ is selected from hydrogen, halogen, hydroxy, —$NO_2$, —CN, —$NH_2$, —O—$C_{1-6}$ alkyl, and $C_{1-6}$ alkyl, wherein the alkyl portion of —O—$C_{1-6}$ alkyl, and $C_{1-6}$ alkyl are optionally substituted with one or more substituents selected from halogen, —OH, —$NH_2$, —$NO_2$, —CN, —O—$C_{1-6}$ alkyl, $C_{3-6}$ carbocycle, and 3- to 6-membered heterocycle; wherein the $C_{3-6}$ carbocycle and 3—to 6-membered heterocycle are each optionally substituted with one or more substituents selected from halogen, hydroxy, —$NO_2$, —CN, —$NH_2$, —O—$C_{1-6}$ alkyl, and $C_{1-6}$ alkyl.

2. The compound or salt of claim 1, wherein the compound of Formula (II') is represented by Formula (IIA'):

(IIA')

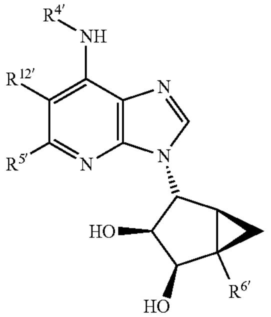

or a pharmaceutically acceptable salt thereof.

3. The compound or salt of claim 1, wherein $R^{4'}$ is selected from optionally substituted $C_{1-2}$ alkyl and optionally substituted $C_3$-$C_6$ carbocycle.

4. The compound or salt of claim 1, wherein $R^{4'}$ is selected from $C_3$-$C_6$ carbocycle and optionally substituted $C_1$-$C_6$ alkyl, wherein optional substituents on $C_1$-$C_6$ alkyl of $R^{4'}$ are independently selected at each occurrence from $R^7$, wherein $R^7$ is selected from fluorine, —$NO_2$, and —CN; and $C_{3-6}$ carbocycle, wherein the $C_{3-6}$ carbocycle is optionally substituted with one or more substituents independently selected from halogen, —$NO_2$, —CN, and $C_{1-3}$ alkyl.

5. The compound or salt of claim 4, wherein $R^{4'}$ is selected from $CH_2CH_3$, $CH_2CFH_2$, $CH_2CF_2H$, $CH_2CF_3$

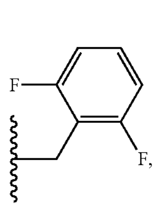 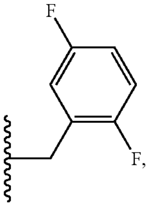 and 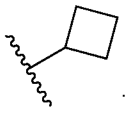 .

6. The compound or salt of claim 1, wherein $R^{5'}$ is selected from hydrogen, $CH_3$, $CH_2CH_3$, —CN, Cl, and

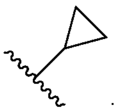 [SMILES: *C1CC1] .

7. The compound or salt of claim 6, wherein $R^{5'}$ is Cl.

8. The compound or salt of claim 1, wherein $R^{6'}$ is selected from hydrogen, $CH_3$, $CH_2F$, $CHF_2$, and $CF_3$.

9. The compound or salt of claim 8, wherein $R^{6'}$ is hydrogen.

10. The compound or salt of claim 1, wherein $R^{6'}$ is —$C(O)(NR^{50}{}_2)$.

11. The compound or salt of claim 10, wherein $R^{6'}$ is —C(O)(NHMe).

12. The compound or salt of claim 1, wherein $R^{12'}$ is selected from hydrogen, halogen, and unsubstituted $C_{1-6}$ alkyl.

13. The compound or salt of claim 12, wherein $R^{12'}$ is hydrogen.

14. The compound or salt of claim 1, wherein the compound is selected from

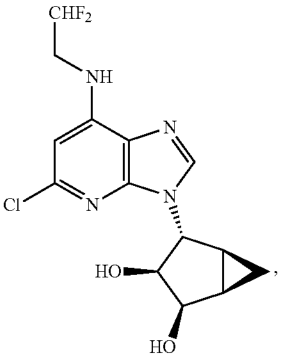 , 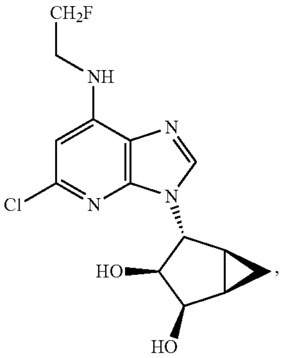 ,

-continued
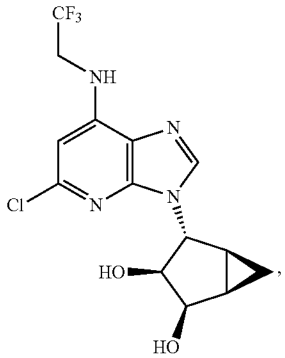
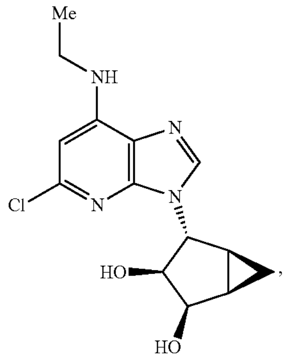
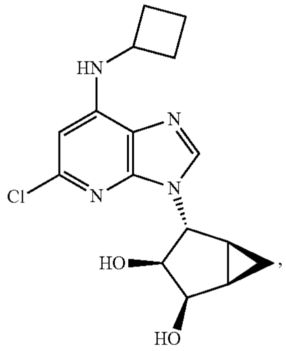
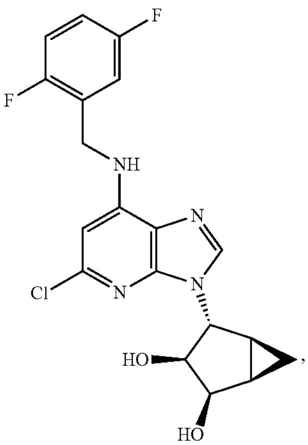
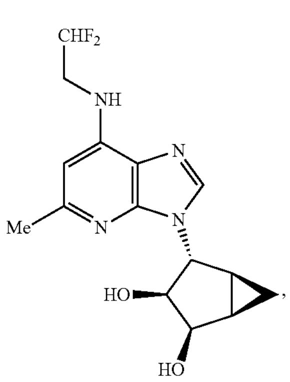
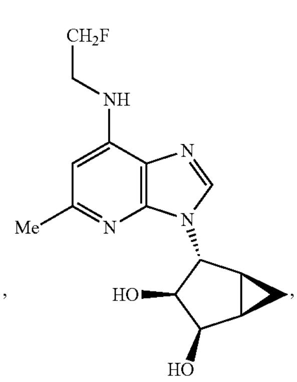
-continued
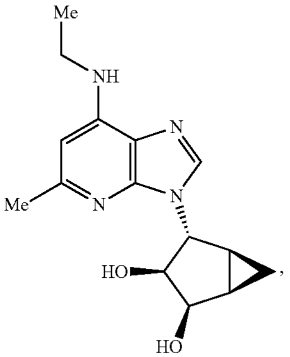
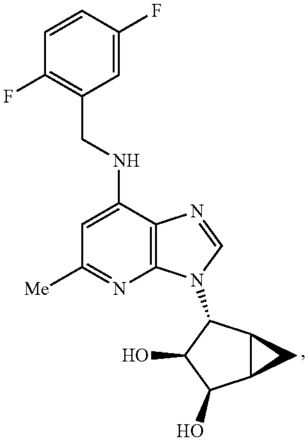
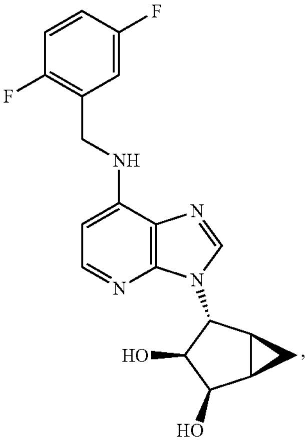
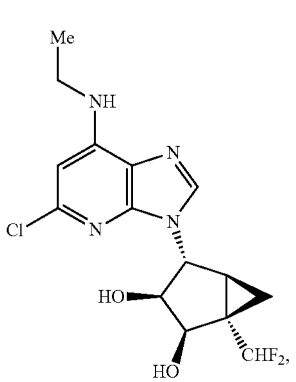
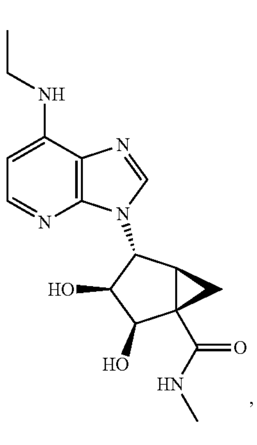

-continued
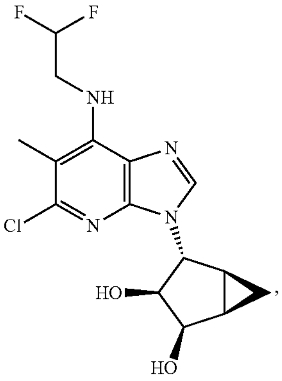
,
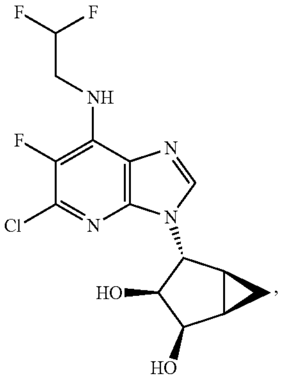
,
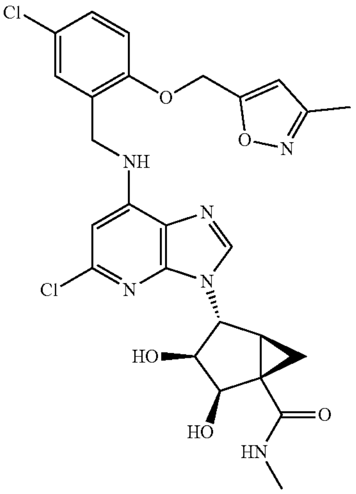
,
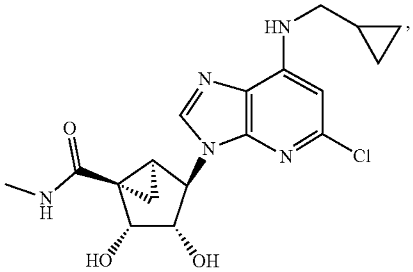
,
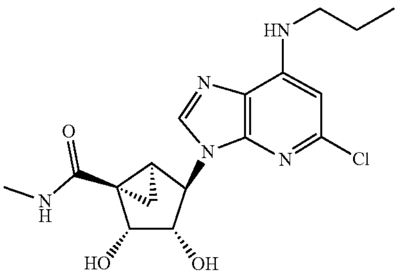
,
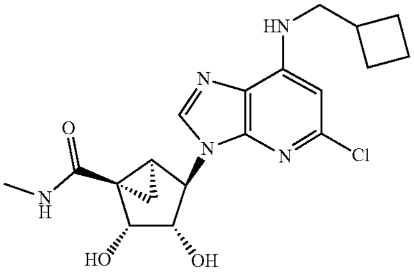
,
-continued
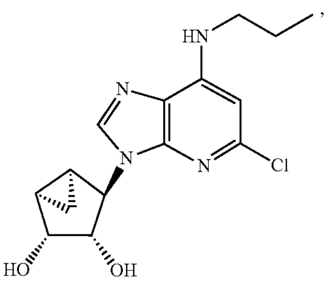
,
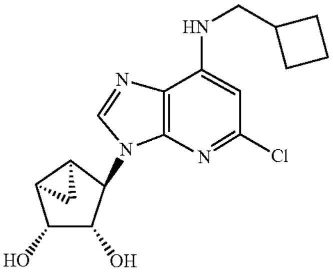
,
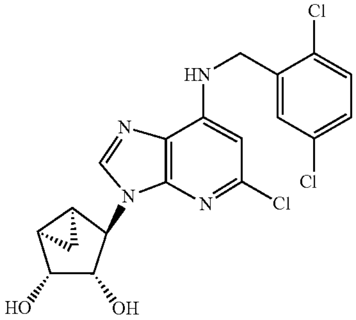
,
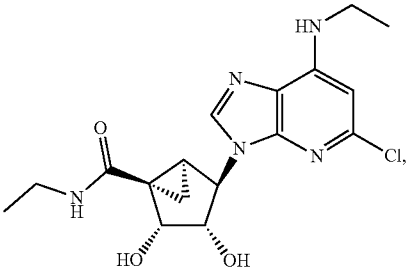
,
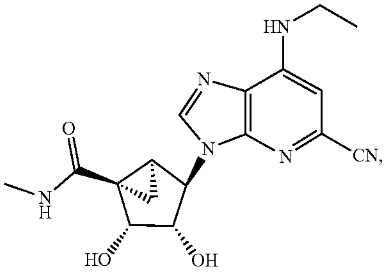
,
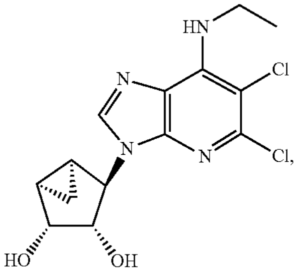
, -continued
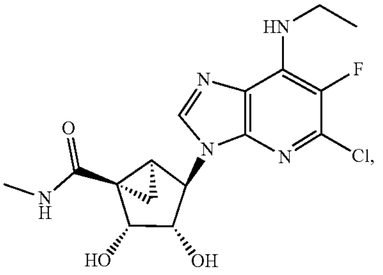
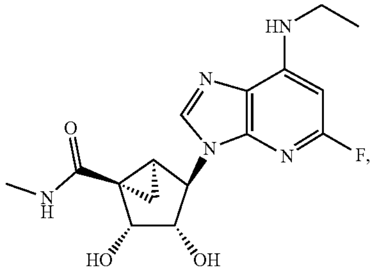
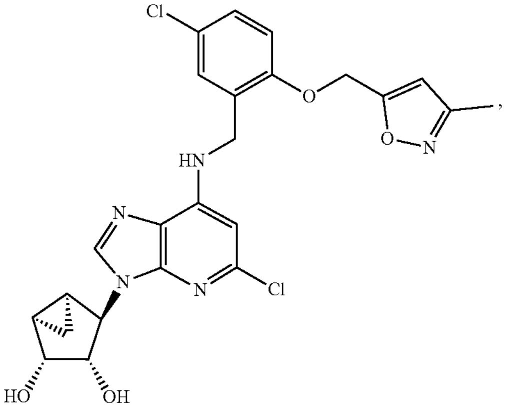
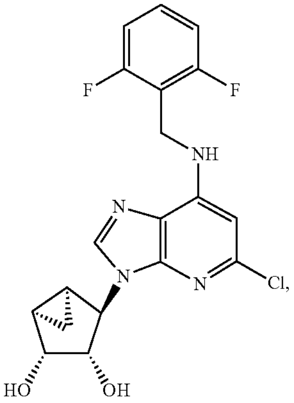
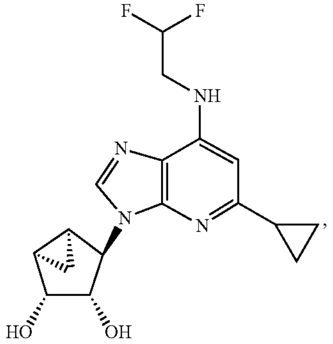
-continued
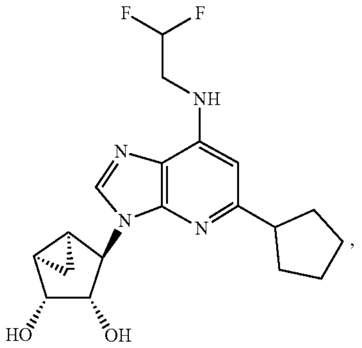
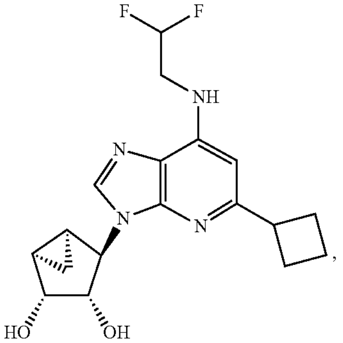
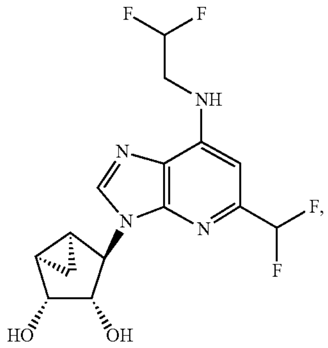
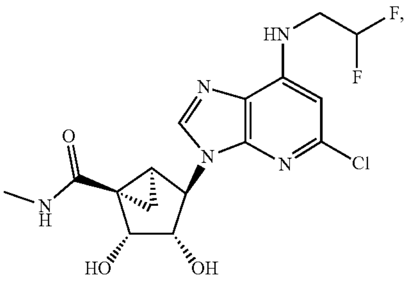
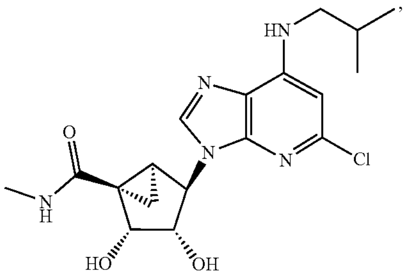

-continued
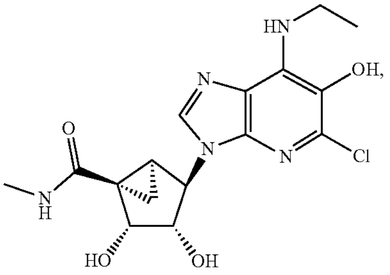
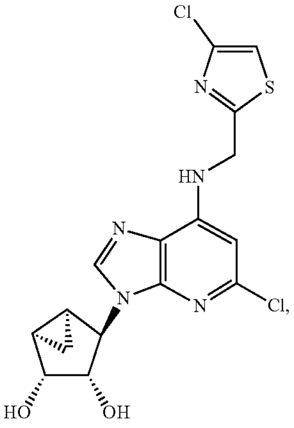
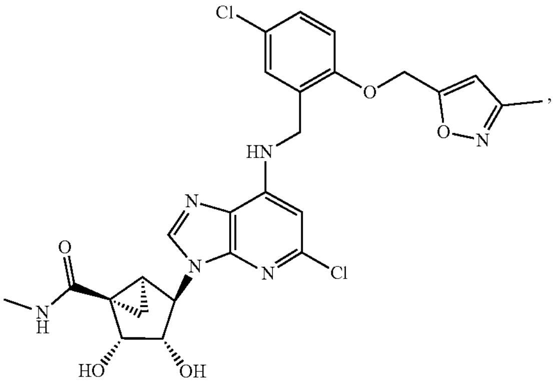
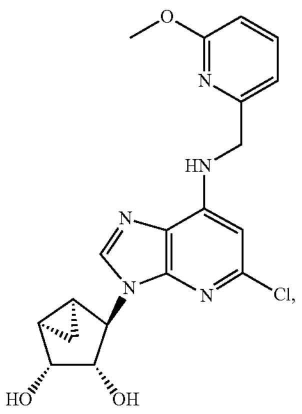
-continued
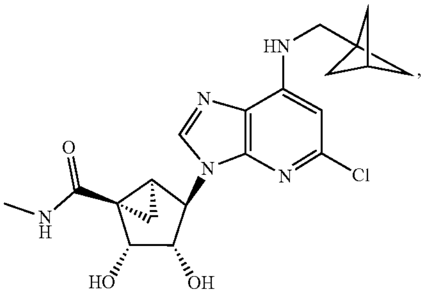
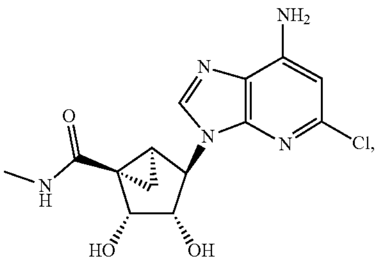
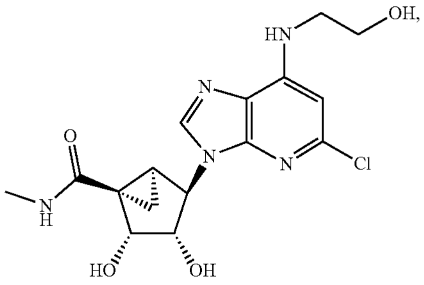
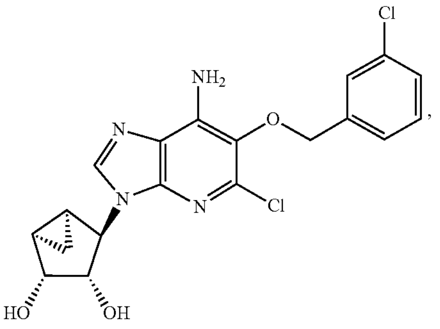
and
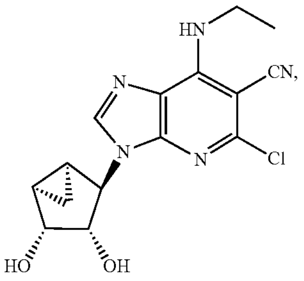
or a pharmaceutically acceptable salt of any one thereof.

15. The compound or salt of claim 1, wherein the compound is selected from
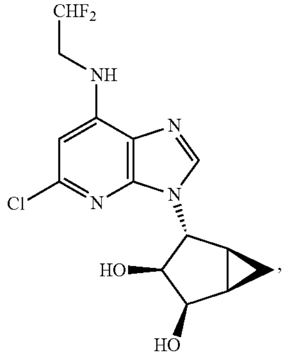
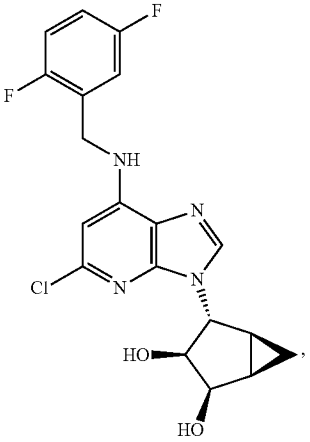
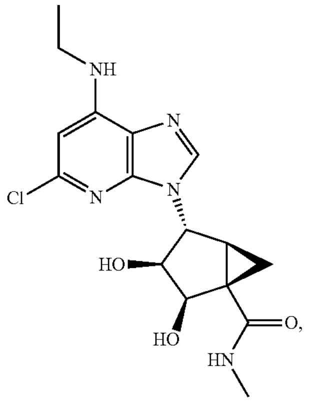
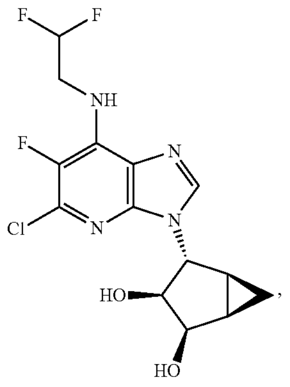
-continued
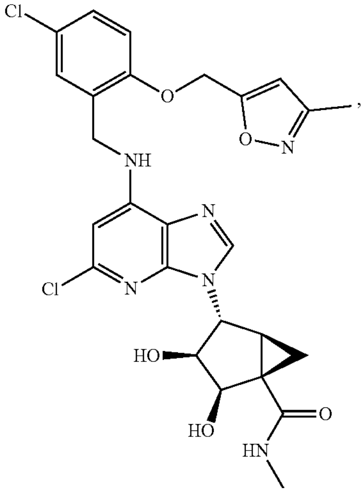
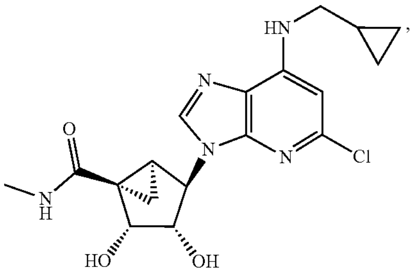
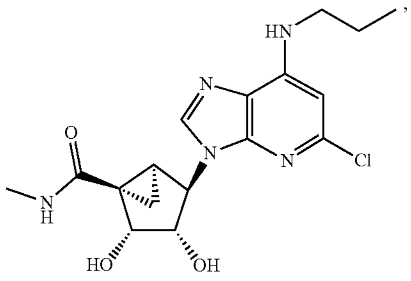
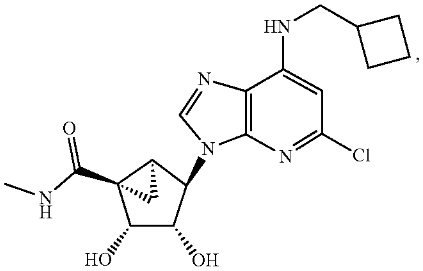
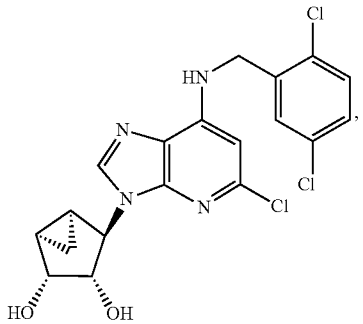

-continued
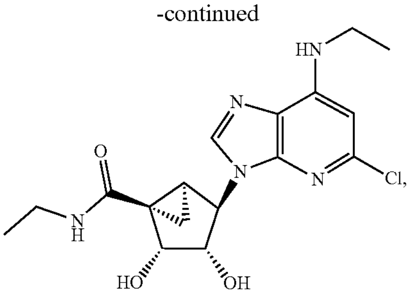
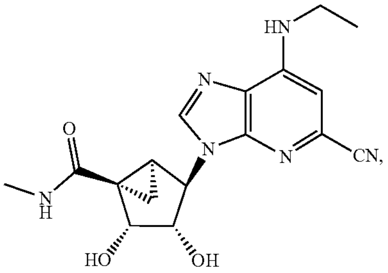
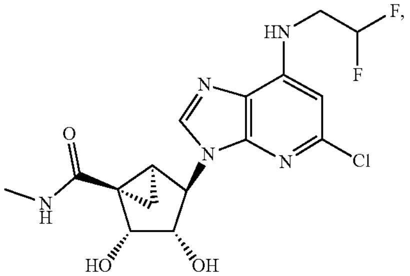
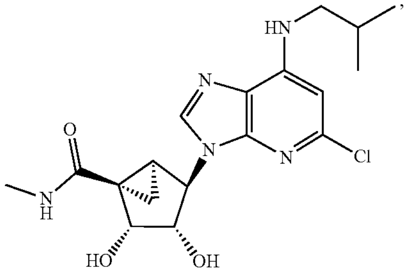
-continued
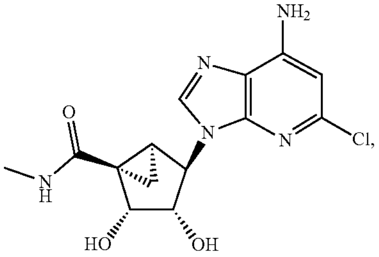
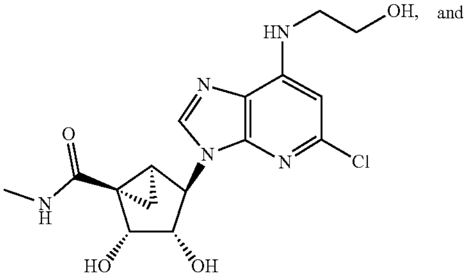
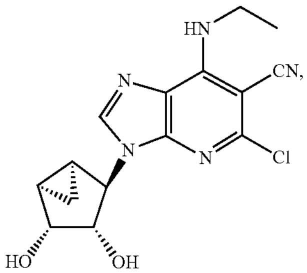
or a pharmaceutically acceptable salt of any one thereof.
16. A pharmaceutical composition comprising a compound or salt of claim 1 and a pharmaceutically acceptable excipient.
* * * * *